(12) United States Patent
Zankel et al.

(10) Patent No.: US 12,128,014 B2
(45) Date of Patent: Oct. 29, 2024

(54) USE OF THIOL COMPOUNDS TO TREAT NEUROLOGICAL DISEASE

(71) Applicant: MERCAPTOR DISCOVERIES, INC., Novato, CA (US)

(72) Inventors: Todd C. Zankel, Novato, CA (US); Sara Louise Isbell, Novato, CA (US)

(73) Assignee: MERCAPTOR DISCOVERIES, INC., Novato, CA (US)

( * ) Notice: Subject to any disclaimer, the term of this patent is extended or adjusted under 35 U.S.C. 154(b) by 0 days.

(21) Appl. No.: 17/711,572

(22) Filed: Apr. 1, 2022

(65) Prior Publication Data

US 2023/0115413 A1   Apr. 13, 2023

Related U.S. Application Data

(63) Continuation of application No. 16/909,463, filed on Jun. 23, 2020, now abandoned, which is a continuation of application No. 15/961,523, filed on Apr. 24, 2018, now abandoned.

(60) Provisional application No. 62/489,132, filed on Apr. 24, 2017.

(51) Int. Cl.

| | |
|---|---|
| *A61K 31/145* | (2006.01) |
| *A61K 31/095* | (2006.01) |
| *A61K 31/198* | (2006.01) |
| *A61K 31/397* | (2006.01) |
| *A61K 31/40* | (2006.01) |
| *A61K 31/4035* | (2006.01) |
| *A61K 31/404* | (2006.01) |
| *A61K 31/407* | (2006.01) |
| *A61K 31/415* | (2006.01) |
| *A61K 31/44* | (2006.01) |
| *A61K 31/445* | (2006.01) |
| *A61K 31/506* | (2006.01) |
| *A61P 25/08* | (2006.01) |

(52) U.S. Cl.
CPC .......... *A61K 31/145* (2013.01); *A61K 31/095* (2013.01); *A61K 31/198* (2013.01); *A61K 31/397* (2013.01); *A61K 31/40* (2013.01); *A61K 31/4035* (2013.01); *A61K 31/404* (2013.01); *A61K 31/407* (2013.01); *A61K 31/415* (2013.01); *A61K 31/44* (2013.01); *A61K 31/445* (2013.01); *A61K 31/506* (2013.01); *A61P 25/08* (2018.01)

(58) Field of Classification Search
CPC .. A61K 31/095; A61K 31/145; A61K 31/198; A61K 31/397; A61K 31/40; A61K 31/4035; A61K 31/404; A61K 31/407; A61K 31/415; A61K 31/44; A61K 31/445; A61K 31/506; C07C 323/30; A61P 25/08
See application file for complete search history.

(56) References Cited

U.S. PATENT DOCUMENTS

| | | |
|---|---|---|
| 5,554,655 A | 9/1996 | Thoene |
| 6,291,425 B1 | 9/2001 | Li et al. |
| 2006/0211748 A1 | 9/2006 | Bain et al. |
| 2011/0124721 A1 | 5/2011 | Wang et al. |
| 2015/0266947 A1 | 9/2015 | Sierks et al. |
| 2015/0337375 A1 | 11/2015 | Crary et al. |
| 2019/0029977 A1 | 1/2019 | Zankel et al. |
| 2021/0069129 A1 | 3/2021 | Zankel et al. |

FOREIGN PATENT DOCUMENTS

| | | | |
|---|---|---|---|
| DE | 4021139 A1 | 1/1992 | |
| WO | WO-2014059442 A2 * | 4/2014 | ............. A61P 25/28 |
| WO | WO-2017004485 A1 * | 1/2017 | ........... A61K 31/145 |

OTHER PUBLICATIONS

Albano et al., Regulation of System xc(−) by Pharmacological Manipulation of Cellular Thiols, Oxid. Med. Cell Longev., 9 pp., 2015: Article ID: 269371 (2015).
Albrecht et al., Mechanisms of oxidative glutamate toxicity: the glutamate/cystine antiporter system xc− as a neuroprotective drug target, CNS Neurol. Disord. Drug Targets, 9(3):373-82 (2010).
Allan et al., Cyclobutane analogs of GABA, Neurochem. Res., 5(4):393-400 (1980).
Alvarez-Zaldiernas et al., Cellular Redox Systems Impact the Aggregation of Cu, Zn Superoxide Dismutase Linked to Familial Amyotrophic Lateral Sclerosis, J. Biol. Chem., 291(33):17197-208 (2016).
Andrew et al., The relationship between trinucleotide (CAG) repeat length and clinical features of Huntington's disease, Nat. Genet., 4(4):398-403 (1993).
Angoa-Pérez et al., Animal models of sports-related head injury: bridging the gap between pre-clinical research and clinical reality, J. Neurochem., 129(6): 916-31 (2014).
Ashby et al., On the kinetics and mechanism of the reaction of cysteine and hydrogen peroxide in aqueous solution, J. Pharm. Sci., 95(1):15-8 (2006).
Asimakopoulou et al., Selectivity of commonly used pharmacological inhibitors for cystathionine β synthase (CBS) and cystathionine ? lyase (CSE), Br. J. Pharmacol., 169(4):922-32 (2013).
Bading, Therapeutic targeting of the pathological triad of extrasynaptic NMDA receptor signaling in neurodegenerations, J. Exp. Med., 214(3):569-78 (2017).
Bak et al., Cysteine-mediated redox signalling in the mitochondria, Mol Biosyst., 11(3):678-97 (2015).
Bardy et al., Neuronal medium that supports basic synaptic functions and activity of human neurons in vitro, Proc. Natl. Acad. Sci. USA, 112(20):E2725-34 (2015).
Baumgartner et al., Calcium elevation in mitochondria is the main Ca2+ requirement for mitochondrial permeability transition pore (mPTP) opening, J. Biol. Chem., 284(31):20796-803 (2009).

(Continued)

*Primary Examiner* — Sarah Pihonak
(74) *Attorney, Agent, or Firm* — MARSHALL, GERSTEIN & BORUN LLP

(57) ABSTRACT

The present disclosure relates, in general, to use of small diffusible thiols in the treatment of neurodegenerative diseases associated with glutamate excitotoxicity, protein aggregation and oxidative stress in the central nervous system, particularly in the brain.

3 Claims, 9 Drawing Sheets

(56) References Cited

OTHER PUBLICATIONS

Ben-Shachar et al., Intranigral iron injection induces behavioral and biochemical "parkinsonism" in rats, J. Neurochem., 57(6):2133-5 (1991).
Bharath et al., Glutathione, iron and Parkinson's disease, Biochem. Pharmacol., 64(5-6):1037-48 (2002).
Biaglow et al., Factors influencing the oxidation of cysteamine and other thiols: implications for hyperthermic sensitization and radiation protection, Radiat. Res., 100(2):298-312 (1984).
Blaylock et al., Immunoexcitotoxicity as a central mechanism in chronic traumatic encephalopathy—A unifying hypothesis, Surg. Neurol. Int., 2:107 (2011).
Blennow et al., The neuropathology and neurobiology of traumatic brain injury, Neuron, 76(5):886-99 (2012).
Bosco et al., Wild-type and mutant SOD1 share an aberrant conformation and a common pathogenic pathway in ALS, Nat. Neurosci., 13(11):1396-403 (2010).
Bridges et al., System xc? cystine/glutamate antiporter: an update on molecular pharmacology and roles within the CNS, Br. J. Pharmacol., 165(1):20-34 (2012).
Bridges et al., Thinking outside the cleft to understand synaptic activity: contribution of the cystine-glutamate antiporter (System xc–) to normal and pathological glutamatergic signaling, Pharmacol. Rev., 64(3):780-802 (2012).
Cacciatore et al., Prodrug approach for increasing cellular glutathione levels, Molecules, 15(3):1242-64 (2010).
Caddick et al., 2-Hydroxy-saclofen causes a phaclofen-reversible reduction in population spike amplitude in the rat hippocampal slice, Eur. J. Pharmacol., 27491):41-6 (1995).
Chang et al., Influence of drug transporters and stereoselectivity on the brain penetration of pioglitazone as a potential medicine against Alzheimer's disease, Sci. Rep., 5:9000 (2015).
Chen et al., Oxidative modification of cysteine 111 promotes disulfide bond-independent aggregation of SOD1, Neurochem. Res., 37(4):835-45 (2012).
Chen et al., Production of the neuromodulator H2S by cystathionine beta-synthase via the condensation of cysteine and homocysteine, J. Biol. Chem., 279(50):52082-6 (2004).
Choi et al., Oxidative modifications and aggregation of Cu,Zn-superoxide dismutase associated with Alzheimer and Parkinson diseases, J. Biol. CHem., 280(12):11648-55 (2005).
Chung et al., Advances in drug design based on the amino Acid approach: taurine analogues for the treatment of CNS diseases, Pharmaceuticals (Basel), 5(10):1128-46 (2012).
Cleret de Langavant et al., Awareness of memory deficits in early stage Huntington's disease, PLoS One, 8(4):e61676 (2013).
Cohen et al., Redox signalling directly regulates TDP-43 via cysteine oxidation and disulphide cross-linking, EMBO J., 31(5):1241-52 (2012).
Cramer et al., Systemic depletion of L-cyst(e)ine with cyst(e)inase increases reactive oxygen species and suppresses tumor growth, Nat. Med., 23(1):120-7 (2017).
Cummings et al., Alzheimer's disease drug-developent pipeline: few candidates, frequent failures, Alzheimer's Res & Ther., vol. 6, pp. 1-7 (2014).
Danysz et al., Alzheimer's disease, β-amyloid, glutamate, NMDA receptors and memantine—searching for the connections, Br. J. Pharmacol., 167(2):324-52 (2012).
Davies, Protein oxidation and peroxidation, Biochem. J., 473(7):805-25 (2016).
Della Corte et al., The use of taurine analogues to investigate taurine functions and their potential therapeutic applications, Amino Acids, 23(4):367-79 (2002).
Ebert et al., Bioisosteric determinants for subtype selectivity of ligands for heteromeric GABA(A) receptors, Bioorg. Med. Chem. Lett., 11(12):1573-7 (2001).
Fehily et al., Repeated Mild Traumatic Brain Injury: Potential Mechanisms of Damage, Cell Transplant, 26(7):1131-55 (2017).
Ferrer-Sueta et al., Factors affecting protein thiol reactivity and specificity in peroxide reduction, Chem. Res. Toxicol., 24(4):434-50 (2011).
Fine et al., Intranasally-administered deferoxamine mitigates toxicity of 6-OHDA in a rat model of Parkinson?s disease, Brain Res., 1574:96-104 (2014).
Fink et al., Inhibition of neuronal Ca(2+) influx by gabapentin and subsequent reduction of neurotransmitter release from rat neocortical slices, Br. J. Pharmacol., 130(4):900-6 (2000).
Foerster et al., An imbalance between excitatory and inhibitory neurotransmitters in amyotrophic lateral sclerosis revealed by use of 3-T proton magnetic resonance spectroscopy, JAMA Neurol., 70(8):1009-16 (2013).
Francelle et al., Possible involvement of self-defense mechanisms in the preferential vulnerability of the striatum in Huntington's disease, Front Cell Neurosci., 8:295 (2014).
Frederick et al., Dysregulation of system xc(–) expression induced by mutant huntingtin in a striatal neuronal cell line and in R6/2 mice, Neurochem. Int., 76:59-69 (2014).
Freedman et al., Treatment optimization in multiple sclerosis, Can. J. Neurol. Sci., 31(2):157-68 (2004).
Freinbichler et al., Highly reactive oxygen species: detection, formation, and possible functions, Cell Mol. Life Sci., 68(12):2067-79 (2011).
Froestl, Chemistry and pharmacology of GABAB receptor ligands, Adv. Pharmacol., 58:19-62 (2010).
Frosini et al., Interactions of taurine and structurally related analogues with the GABAergic system and taurine binding sites of rabbit brain, Br. J. Pharmacol., 138(6):1163-71 (2003).
Galgano et al., Chronic Traumatic Encephalopathy: The Impact on Athletes, Cureus, 8(3):e532 (2016).
Giacomelli et al., Potential biomarkers and novel pharmacological targets in protein aggregation-related neurodegenerative diseases, Biochem. Pharmacol., 131:1-15 (2017).
Golko-Perez et al., A Novel Iron Chelator-Radical Scavenger Ameliorates Motor Dysfunction and Improves Life Span and Mitochondrial Biogenesis in SOD1$^{G93A}$ ALS Mice, Neurotox. Res., 31(2):230-44 (2017).
Guerriero et al., Glutamate and GABA imbalance following traumatic brain injury, Curr. Neurol. Neurosci. Rep., 15(5):27 (2015).
Gupta et al., Taurine analogues; a new class of therapeutics: retrospect and prospects, Curr. Med. Chem., 12(17):2021-39 (2005).
Gupta, Taurine analogues and taurine transport: therapeutic advantages, Adv. Exp. Med. Biol., 583:449-67 (2006).
Güngör et al., Comparative evaluation of antioxidant capacities of thiol-based antioxidants measured by different in vitro methods, Talanta, 83(5):1650-8 (2011).
Ha et al., Huntington's disease, Curr. Opin. Neurol., 25(4):491-8 (2012).
Hackett et al., Imaging Taurine in the Central Nervous System Using Chemically Specific X-ray Fluorescence Imaging at the Sulfur K-Edge, Anal. Chem., 88(22):10946-24 (2016).
Hackett et al., Novel bio-spectroscopic imaging reveals disturbed protein homeostasis and thiol redox with protein aggregation prior to hippocampal CA1 pyramidal neuron death induced by global brain ischemia in the rat, Free Radic. Biol. Med., 89:806-18 (2015).
Hackett et al., X-ray absorption spectroscopy at the sulfur K-edge: a new tool to investigate the biochemical mechanisms of neurodegeneration, ACS Chem. Neurosci., 3(3):178-85 (2012).
Heppner et al., The role of sulfenic acids in cellular redox signaling: Reconciling chemical kinetics and molecular detection strategies, Arch. Biochem. Biophys., 616:40-6 (2017).
Ho et al., Impact of Huntington's across the entire disease spectrum: the phases and stages of disease from the patient perspective, Clin. Genet., 80(3):235-9 (2011).
Hoehn et al., Parkinsonism: onset, progression and mortality, Neurology, 17(5):427-42 (1967).
International Application No. PCT/US2018/029145, International Search Report and Written Opinion, mailed Jul. 17, 2018.
Irie et al., Influence of the Radiation Protective Agents on the Therapeutical Effects of Radiations for Malignant Tissues, Chemotherapia, 3:176-188 (1961).

(56) References Cited

OTHER PUBLICATIONS

Issels et al., Promotion of cystine uptake and its utilization for glutathione biosynthesis induced by cysteamine and N-acetylcysteine, Biochem. Pharmacol., 37(5):881-8 (1988).
Johnson et al., Beta-proline analogues as agonists at the strychnine-sensitive glycine receptor, J. Med. Chem., 35(2):233-41 (1992).
Jucker et al., Self-propagation of pathogenic protein aggregates in neurodegenerative diseases, Nature, 501(7465):45-51 (2013).
Jurkowska et al., Propargylglycine inhibits hypotaurine/taurine synthesis and elevates cystathionine and homocysteine concentrations in primary mouse hepatocytes, Amino Acids, 47(6):1215-23 (2015).
Karpuj et al., Transglutaminase aggregates huntingtin into nonamyloidogenic polymers, and its enzymatic activity increases in Huntington's disease brain nuclei, Proc. Natl. Acad. Sci. USA, 96(13):7388-93 (1999).
Kigerl et al., System x(c)(−) regulates microglia and macrophage glutamate excitotoxicity in vivo, Exp. Neurol., 233(1):333-41 (2012).
Kim et al., Identification of disulfide cross-linked tau dimer responsible for tau propagation, Sci. Rep., 5:15231 (2015).
Kim et al., ROSics: chemistry and proteomics of cysteine modifications in redox biology, Mass. Spectrom. Rev., 34(2):184-208 (2015).
Kosmidis et al., Ferritin overexpression in *Drosophila* glia leads to iron deposition in the optic lobes and late-onset behavioral defects, Neurobiol. Dis., 43(1):213-9 (2011).
Krall et al., GABAA receptor partial agonists and antagonists: structure, binding mode, and pharmacology, Adv. Pharmacol., 72:201-27 (2015).
Krogsgaard-Larsen et al., Dihydromuscimol, thiomuscimol and related heterocyclic compounds as GABA analogues, J. Neurochem., 32(6):1717-24 (1979).
Krogsgaard-Larsen et al., GABA uptake inhibitors. Design, molecular pharmacology and therapeutic aspects, Curr. Pharm. Des., 6(12):1193-209 (2000).
Krogsgaard-Larsen et al., Heterocyclic analogues of GABA: chemistry, molecular pharmacology and therapeutic aspects, Prog. Med. Chem., 22:67-120 (1985).
Krumova et al., "Overview of Reactive Oxygen Species", Chapter 1 IN: Nonell et al. (eds.), Singlet Oxygen: Applications in Biosciences and Nanosciences, vol. 1, Royal Society of Chemistry (2016).
Labbadia et al., Huntington's disease: underlying molecular mechanisms and emerging concepts, Trends Biochem. Sci., 38(8):378-85 (2013).
Lee et al., Prion-like Mechanism in Amyotrophic Lateral Sclerosis: are Protein Aggregates the Key?, Exp. Neurobiol., 24(1):1-7 (2015).
Levandovskiy et al., Conformationally restricted GABA analogs: from rigid carbocycles to cage hydrocarbons, Future Med. Chem., 3(2):223-41 (2011).
Lewerenz et al., Basal levels of eIF2alpha phosphorylation determine cellular antioxidant status by regulating ATF4 and xCT expression, J. Biol. Chem., 284(2):1106-15 (2009).
Lewerenz et al., Chronic Glutamate Toxicity in Neurodegenerative Diseases—What is the Evidence?, Front Neurosci., 9:469 (2015).
Lewerenz et al., Cooperative action of glutamate transporters and cystine/glutamate antiporter system Xc− protects from oxidative glutamate toxicity, J. Neurochem., 98(3):916-25 (2006).
Li et al., Soluble Aβ oligomers inhibit long-term potentiation through a mechanism involving excessive activation of extrasynaptic NR2B-containing NMDA receptors, J. Neurosci., 31(18):6627-38 (2011).
Liebowitz et al., Cyclic taurine analogs. Synthesis and effects on ATP-dependent Ca2+ uptake in rat retina, Biochem. Pharmacol., 36(13):2109-14 (1987).
Liebowitz et al., Effects of aminocycloalkanesulfonic acid analogs of taurine on ATP-dependent calcium ion uptake and protein phosphorylation, Biochem. Pharmacol., 37(7):1303-9 (1988).
Liebowitz et al., Sulfone analogues of taurine as modifiers of calcium uptake and protein phosphorylation in rat retina, Biochem. Pharmacol., 38(3):399-406 (1989).
Limón-Pacheco et al., The role of antioxidants and antioxidant-related enzymes in protective responses to environmentally induced oxidative stress, Mutat. Res., 674(1-2):137-47 (2009).
Lin, Coexistence of zinc and iron augmented oxidative injuries in the nigrostriatal dopaminergic system of SD rats, Free Radic. Biol. Med., 30(3):225-31 (2001).
Lombardini et al., Taurine analogues as modifiers of the accumulation of 45calcium ions in a rat retinal membrane preparation, Curr. Eye res., 9(12):1147-56 (1990).
Loy et al., Is a motor criterion essential for the diagnosis of clinical huntington disease?, Version 2, PLoS Curr., 5 (2013).
Luo et al., Kinetics and mechanism of the reaction of cysteine and hydrogen peroxide in aqueous solution, J. Pharm. Sci., 9492):304-16 (2005).
Maggioni et al., Neurobasal medium toxicity on mature cortical neurons, Neuroreport, 26(6):320-4 (2015).
Maher et al., A novel approach to enhancing cellular glutathione levels, J. Neurochem., 107(3):690-700 (2008).
Manevich et al., Peroxiredoxin VI oxidation in cerebrospinal fluid correlates with traumatic brain injury outcome, Free Radic. Biol. Med., 72:210-21 (2014).
Mansuy et al., Sulfenic acids as reactive intermediates in xenobiotic metabolism, Arch. Biochem. Biophys., 507(1):174-85 (2011).
Margulies et al., Combination therapies for traumatic brain injury: prospective considerations, J. Neurotrauma, 26(6):925-39 (2009).
Martineau et al., Investigation of the noncovalent interactions between anti-amyloid agents and amyloid beta peptides by ESI-MS, J. Am. Soc. Mass Spectrom., 21(9):1506-14 (2010).
Massie et al., Main path and byways: non-vesicular glutamate release by system xc(−) as an important modifier of glutamatergic neurotransmission, J. Neurochem., 135(6):1062-79 (2015).
Mattson et al., beta-Amyloid peptides destabilize calcium homeostasis and render human cortical neurons vulnerable to excitotoxicity, J. Neurosci., 1292):376-89 (1992).
McBean et al., Redox-based therapeutics in neurodegenerative disease, Br. J. Pharmacol., 174(12):1750-70 (2017).
McBean et al., Thiol redox homeostasis in neurodegenerative disease, Redox Biol., 5:186-94 (2015).
McKee et al., TDP-43 proteinopathy and motor neuron disease in chronic traumatic encephalopathy, J. Neuropathol. Exp. Neurol., 69(9):918-29 (2010).
Mironov et al., [Ca2+]i signaling between mitochondria and endoplasmic reticulum in neurons is regulated by microtubules. From mitochondrial permeability transition pore to Ca2+-induced Ca2+ release, J. Biol. Chem., 280(1):715-21 (2005).
Mishanina et al., Biogenesis of reactive sulfur species for signaling by hydrogen sulfide oxidation pathways, Nat. Chem. Biol., 11(7):457-64 (2015).
Nagano et al., A cysteine residue affects the conformational state and neuronal toxicity of mutant SOD1 in mice: relevance to the pathogenesis of ALS, Hum. Mol. Genet., 24(12):3427-39 (2015).
Nagy et al., Kinetics and mechanisms of thiol-disulfide exchange covering direct substitution and thiol oxidation-mediated pathways, Antioxid. Redox Signal., 18(13):1623-41 (2013).
Nicholls, Brain mitochondrial calcium transport: Origins of the set-point concept and its application to physiology and pathology, Neurochem. Int., 109:5-12 (2017).
Nielsen et al., GABA agonists and uptake inhibitors. Synthesis, absolute stereochemistry, and enantioselectivity of (R)-(−)- and (S)-(+)-homo-beta-proline, J. Med. Chem., 33(1):71-7 (1990).
Nonaka et al., TDP-43 Prions, Cold Spring Harb. Perspect. Med., 8:a024463 (Mar. 2018).
Novoselov et al., Molecular chaperone mediated late-stage neuroprotection in the SOD1(G93A) mouse model of amyotrophic lateral sclerosis, PLoS One, 8(8):e73944 (2013).
Offen et al., Prevention of dopamine-induced cell death by thiol antioxidants: possible implications for treatment of Parkinson's disease, Exp. Neurol., 141(1):32-9 (1996).
Omalu, Chronic traumatic encephalopathy, Prog. Neurol. Surg., 28:38-49 (2014).
Parone et al., Enhancing mitochondrial calcium buffering capacity reduces aggregation of misfolded SOD1 and motor neuron cell

(56) References Cited

OTHER PUBLICATIONS death without extending survival in mouse models of inherited amyotrophic lateral sclerosis, J. Neurosci., 33(11):4657-71 (2013).

Patel et al., Differentiation of substrate and non-substrate inhibitors of transport system xc(−): an obligate exchanger of L-glutamate and L-cystine, Neuropharmacology, 46(2):273-84 (2004).

Patel, Targeting Oxidative Stress in Central Nervous System Disorders, Trends Pharm. Sci., 37(9):768-78 (2016).

Patterson et al., Depolarization-induced calcium responses in sympathetic neurons: relative contributions from Ca2+ entry, extrusion, ER/mitochondrial Ca2+ uptake and release, and Ca2+ buffering, J. Gen. Physiol., 129(1):29-56 (2007).

Peters et al., The relationship between iron dyshomeostasis and amyloidogenesis in Alzheimer's disease: Two sides of the same coin, Neurobiol. Dis., 81:49-65 (2015).

Poole, The basics of thiols and cysteines in redox biology and chemistry, Free Radic. Biol. Med., 80:148-57 (2015).

Qiu et al., Inhibition and substrate activity of conformationally rigid vigabatrin analogues with gamma-aminobutyric acid aminotransferase, J. Med. Chem., 42(22):4725-8 (1999).

Ricci et al., Inhibition of rabbit brain 4-aminobutyrate transaminase by some taurine analogues: a kinetic analysis, Biochem. Pharmacol., 71(10):1510-9 (2006).

Ricci et al., Taurine-like GABA aminotransferase inhibitors prevent rabbit brain slices against oxygen-glucose deprivation-induced damage, Amino Acids, 42(6):2139-47 (2012).

Ross et al., Huntington's disease: from molecular pathogenesis to clinical treatment, Lancet Neurol., 10(1):83-98 (2011).

Salat et al., GABA transporters as targets for new drugs, Future Med. Chem., 3(2):211-22 (2011).

Schieber et al., ROS function in redox signaling and oxidative stress, Curr. Biol., 24(10):R453-62 (2014).

Schwarz et al., Novel cyclopropyl beta-amino acid analogues of pregabalin and gabapentin that target the alpha2-delta protein, J. Med. Chem., 48(8):3026-35 (2005).

Shen et al., A continuous spectrophotometric assay for human cystathionine beta-synthase, Anal. Biochem., 342(1):103-10 (2005).

Shih et al., Cystine/glutamate exchange modulates glutathione supply for neuroprotection from oxidative stress and cell proliferation, J. Neurosci., 26(41):10514-23 (2006).

Sies, Hydrogen peroxide as a central redox signaling molecule in physiological oxidative stress: Oxidative eustress, Redox Biology, 11:613-9 (2017).

Silverman, The 2011 E. B. Hershberg award for important discoveries in medicinally active substances: (1S,3S)-3-amino-4-difluoromethylenyl-1-cyclopentanoic acid (CPP-115), a GABA aminotransferase inactivator and new treatment for drug addiction and infantile spasms, J. Med. Chem., 55(2):567-75 (2012).

Smethurst et al., In vitro prion-like behaviour of TDP-43 in ALS, Neurobiol. Dis., 96:236-47 (2016).

Song et al., Molecular chaperone Hsp110 rescues a vesicle transport defect produced by an ALS-associated mutant SOD1 protein in squid axoplasm, Proc. Natl. Acad. Sci. USA, 110(14):5428-33 (2013).

Sriram et al., Thiol oxidation and loss of mitochondrial complex I precede excitatory amino acid-mediated neurodegeneration, J. Neurosci., 18(24):10287-96 (1998).

Stout et al., Glutamate-induced neuron death requires mitochondrial calcium uptake, Nat. Neurosci., 1(5):366-73 (1998).

The Huntington's Disease Collaborative Research Group, A novel gene containing a trinucleotide repeat that is expanded and unstable on Huntington's disease chromosomes, Cell, 72(6):971-83 (1993).

Thorson et al., Identification of cystathionine β-synthase inhibitors using a hydrogen sulfide selective probe, Angew. Chem. Int. Ed. Engl., 52(17):4641-4 (2013).

Tokuda et al., Copper Homeostasis as a Therapeutic Target in Amyotrophic Lateral Sclerosis with SOD1 Mutations, Int. J. Mol. Sci., 17(5): E636 (2016).

Trujillo et al., One- and two-electron oxidation of thiols: mechanisms, kinetics and biological fates, Free Radic. Res., 50(2):150-71 (2016).

Turner et al., Controversies and priorities in amyotrophic lateral sclerosis, Lancet Neurol., 12(3):310-22 (2013).

Van Bergen et al., From thiol to sulfonic acid: modeling the oxidation pathway of protein thiols by hydrogen peroxide, J. Phys. Chem. A, 118(31):6078-84 (2014).

Van Den Bosch et al., The role of excitotoxicity in the pathogenesis of amyotrophic lateral sclerosis, Biochim. Biophys. Acta, 1762(11-12):1068-82 (2006).

White et al., Mitochondria and Na+/Ca2+ exchange buffer glutamate-induced calcium loads in cultured cortical neurons, J. Neurosci., 15(2):1318-28 (1995).

Wilmer et al., Cysteamine restores glutathione redox status in cultured cystinotic proximal tubular epithelial cells, Biochim. Biophys. Acta, 1812(6):643-51 (2011).

Xie et al., New insights into the role of mitochondrial dysfunction and protein aggregation in Parkinson's disease, Biochim. Biophys. Acta, 1802(11):935-41 (2010).

Yin et al., L-Cysteine metabolism and its nutritional implications, Mol. Nutr. Food Res., 60(1):134-46 (2016).

Yogeeswari et al., An update on GABA analogs for CNS drug discovery, Recent Pat. CNS Drug Discov., 1(1):113-8 (2006).

Yudkoff et al., Effects of cysteamine therapy in nephropathic cystinosis, N. Engl. J. Med., 304(3):141-5 (1981).

Zarei et al., A comprehensive review of amyotrophic lateral sclerosis, Surg. Neurol. Int., 6:171 (2015).

Zeevalk et al., Excitotoxicity and oxidative stress during inhibition of energy metabolism, Dev. Neurosci., 20(4-5):444-53 (1998).

Zhao et al., Synthesis and biological evaluation of new GABA-uptake inhibitors derived from proline and from pyrrolidine-2-acetic acid, Eur. J. Med. Chem., 40(3):231-47 (2005).

Zheng et al., Regulation of brain iron and copper homeostasis by brain barrier systems: implication in neurodegenerative diseases, Pharmacol. Ther., 133(2):177-88 (2012).

Zuccato et al., Molecular mechanisms and potential therapeutical targets in Huntington's disease, Physiol. Rev., 90(3):905-81 (2010).

\* cited by examiner

Oxoanion                     Thiol                    Oxidized Thiol

Log P: -3.1                  Log P: 0.03                tPSA: 109.36
tPSA: 115.35                 tPSA: 52.16

Log P: 1.26                  Log P: 2.21                tPSA: 86.3
tPSA: 69.23                  tPSA: 29.1

Log P: 4.87                  Log P: 6.17                tPSA: 86.3
tPSA: 69.23                  tPSA: 29.1

Oxoanion                     Thiol                    Oxidized Thiol tPSA: 86.3                   Log P: -0.3              
                             tPSA: 29.1

Log P: -1.33                 tPSA: 27.64              tPSA: 84.84
tPSA: 67.77

Log P: -0.76                 Log P: 0.43              tPSA: 84.84
tPSA: 67.77                  tPSA: 27.64

| Oxoanion | Thiol | Oxidized Thiol |
|---|---|---|
|  Log P: -0.29<br>tPSA: 67.77 |  Log P: 0.69<br>tPSA: 27.64 |  tPSA: 84.84 |
|  Log P: -1.36<br>tPSA: 67.77 |  tPSA: 27.64 |  tPSA: 84.84 |
|  tPSA: 84.84 |  Log P: 2.4<br>tPSA: 27.64 |  tPSA: 84.84 |

USE OF THIOL COMPOUNDS TO TREAT NEUROLOGICAL DISEASE

FIELD OF THE DISCLOSURE

The present disclosure relates, in general, to use of small diffusible thiols in the treatment of neurodegenerative diseases associated with glutamate excitotoxicity, protein aggregation and oxidative stress in the central nervous system, particularly in the brain.

BACKGROUND

Endogenous thiols, primarily cysteine and its derivatives, act as electron sources and transfer mediators, ensuring the homeostatic maintenance of organellar redox states, especially in the mitochondria (25-34). As strong coordination ligands, they allow proteins to access metal ion chemistry, which are fundamental to the generation of energy and electron-rich cellular currencies but may be dangerous when not properly controlled (35-41). It has been shown that upon ingestion, cysteamine or cystamine can increase levels of cysteine in blood by cleaving cystine (9-11). This effect, in turn, increases brain and intracellular sulfur amino acid levels by increasing flux through underutilized pathways, overcoming the lack of cystine transport across the BBB, and easing reliance on cystine-glutamate exchange within the parenchyma (12-24).

Neurodegeneration is characterized by oxidative depletion of native thiols. Another feature of neurodegeneration is intracellular protein aggregation (42-59). Organelle-specific protein aggregates inhibit transcription, RNA processing, axonal transport and mitochondrial function (42,47,55,57, 60). Pathogenic aggregation is gated by cysteine oxidation in least three proteins, tau, SOD1 and TDP-43 (44-46,48, 56,61,62). Aggregates of these proteins are found in amyotrophic lateral sclerosis (ALS), chronic traumatic encephalopathy (CTE) and Alzheimer's disease (39,50,52,63,64). Thiols have been shown to reduce and, in the early stages, reverse, some protein aggregate formation (43-45,56,61).

SUMMARY OF THE DISCLOSURE

Low-molecular weight aminothiols, or captons as used herein, are selected for optimal reactivity, metabolic stability, pharmacokinetic persistence and oral bioavailability for use in treating neurodegenerative diseases. Captons are unique in their display of GABAergic or taurinergic activity after thiol oxidation upon crossing of the Blood Brain Barrier (BBB).

Provided herein is a method of treating a neurological disease or disorder comprising administering a small thiol compound (<500 daltons, log P >0.8, TPSA <90) that can be oxidized by reactive-oxygen species after crossing the blood-brain barrier to a sulfinic or sulfonic acid and wherein the oxidized compound possesses GABAergic, calcium channel inhibiting, glutamatergic or other neurologic activity.

Also provided is a method of treating an excitotoxicity disorder comprising administering a small thiol compound having a molecular weight<500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

Further contemplated is a method of treating a neurological disease or disorder characterized by aggregation of TDP-43 comprising administering a small thiol compound having a molecular weight<500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

The disclosure also provides a method of treating a neurological disease or disorder characterized by aggregation of superoxide dismutase 1 (SOD1) protein comprising administering a small thiol compound having a molecular weight <500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

In various embodiments, the disease is further characterized by aggregation of tau protein.

In various embodiments, the disease or disorder is amyotrophic lateral sclerosis (ALS), frontotemporal lobar degeneration, traumatic brain injury, chronic traumatic encephalopathy (CTE), Alzheimer's disease, ischemia or epilepsy. In various embodiments, the disease is familial or sporadic ALS.

The disclosure further contemplates a method of preventing or ameliorating brain injury caused by trauma comprising administering to a subject in need thereof a small thiol compound having a molecular weight <500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity. prior to the subject undertaking activity in which the brain may be injured.

In various embodiments, the disclosure provides a method for protecting neurons from trauma and injury comprising administering to a subject in need thereof a small thiol compound.

In various embodiments, the compound reduces protein aggregation, neuronal overexcitation or oxidative stress characteristic of neurodegenerative disorders.

Contemplated herein is a method for treating or ameliorating glutamate toxicity in a subject comprising administering an effective amount of a small thiol compound having a molecular weight <500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

In various embodiments, the administration reduces neuronal glutamate toxicity.

It is contemplated that the small diffusible thiol compound useful in any one of the methods is a capton as described herein. Exemplary captons are set out in FIGS. 1 and 2, in Formulas I, II and III, in Table A, and described further in the detailed description.

Further provided is a method for slowing the degeneration of neurons in a subject comprising administering an effective amount of a compound of Formula I, II or III, Table A, or a small thiol compound having a molecular weight <500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

Also contemplated is a method for treating or ameliorating glutamate toxicity in a subject comprising administering an effective amount of a compound of Formula I, II or III, Table A, or a small thiol compound having a molecular weight <500 daltons, a log P >0.8, and a TPSA <90 that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

In various embodiments, disclosed are methods of using compounds of Formula (I):

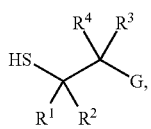

(I)

wherein:

$R^1$ and $R^2$ are independently selected from the group consisting of H and $C_{1-5}$alkyl; or $R^1$ and $R^2$, taken together with the carbon atom to which they are attached, form a 3-, 4-, 5-, 6-, 7-, or 8-membered carbocyclic ring;

$R^3$ and $R^4$ are independently selected from the group consisting of H and $C_{1-5}$alkyl; or $R^3$ and $R^4$, taken together with the carbon atom to which they are attached, form a 3-, 4-, 5-, 6-, 7-, or 8-membered carbocyclic ring;

G is selected from the group consisting of —$NR^5R^6$ and —$CR^7R^8NR^5R^6$-;

$R^5$ and $R^6$ are independently selected from the group consisting of H and $C_{1-5}$alkyl; or $R^5$ and $R^6$, taken together with the nitrogen atom to which they are attached, form a 3-, 4-, 5-, 6-, 7-, or 8-membered heterocyclic ring;

$R^7$ and $R^8$ are independently selected from the group consisting of H and $C_{1-5}$alkyl; or $R^7$ and $R^8$, taken together with the carbon atom to which they are attached, form a 3-, 4-, 5-, 6-, 7-, or 8-membered carbocyclic ring;

$R^2$ and $R^6$, taken together with the atoms to which they are attached, optionally form a 4-,5-, 6-, 7-, 8-, 9-, or 10-membered heterocyclic ring;

$R^4$ and $R^6$, taken together with the atoms to which they are attached, optionally form a 4-,5-, 6-, 7-, 8-, 9-, or 10-membered heterocyclic ring;

$R^4$ and $R^8$, taken together with the atoms to which they are attached, optionally form a 3-4-, 5-, 6-, 7-, or 8-membered carbocyclic ring;

$R^2$ and $R^8$, taken together with the atoms to which they are attached, optionally form a 3-4-, 5-, 6-, 7-, or 8-membered carbocyclic ring;

$R^2$ and $R^4$, taken together with the atoms to which they are attached, optionally form a 3-4-, 5-, 6-, 7-, or 8-membered carbocyclic ring;

wherein a $C_{1-5}$alkyl moiety, wherever it occurs, can optionally comprise a double bond; and wherein a $C_{1-5}$alkyl, 3-, 4-, 5-, 6-, 7-, or 8-membered carbocyclic or heterocyclic moiety, wherever it occurs, can optionally be substituted with from one to three substituents which are not further substituted and which are independently selected from the group consisting of —CN, thio, halo, hydroxy, $C_{6-10}$aryl, $C_{1-5}$alkyl, $C_{2-6}$ alkenyl, $C_{3-6}$cycloalkyl, 5- or 6-membered heterocycloalkyl containing 1-3 heteroatoms selected from O, N, and S, $CO_2H$, $CO_2C_{1-6}$alkyl, $C(O)C_{1-6}$alkyl, $CO_2NH_2$, $CO_2NHC_{1-6}$alkyl, and —$CO_2N(C_{1-6}$alkyl$)_2$.

In various embodiments, disclosed are methods of using a compound of Formula II:

(II), wherein:

L is a hydrocarbon linking group;

$R^9$ and $R^{10}$ are independently selected from the group consisting of H, $C_{1-5}$alkyl, and $CO(C_{1-5}$alkyl); or $R^9$ and $R^{10}$, taken together with the nitrogen atom to which they are attached, form a 3-, 4-, 5-, 6-, 7-, or 8-membered heterocyclic ring;

wherein a $C_{1-5}$alkyl moiety, wherever it occurs, can optionally comprise a double bond; and wherein a $C_{1-5}$alkyl, 3-, 4-, 5-, 6-, 7-, or 8-membered carbocyclic or heterocyclic moiety, wherever it occurs, can optionally be substituted with from one to three substituents which are not further substituted and which are independently selected from the group consisting of —CN, thio, halo, hydroxy, $C_{6-10}$aryl, $C_{1-5}$alkyl, $C_{2-6}$ alkenyl, $C_{3-6}$cycloalkyl, 5- or 6-membered heterocycloalkyl containing 1-3 heteroatoms selected from O, N, and S, $CO_2H$, $CO_2C_{1-6}$alkyl, $C(O)C_{1-6}$alkyl, $CO_2NH_2$, $CO_2NHC_{1-6}$alkyl, and —$CO_2N(C_{1-6}$alkyl$)_2$.

In various embodiments, disclosed are methods of using a compound of Formula (III):

(III)

wherein:

A is a 3 to 8 membered heterocyclic ring containing one N atom;

n is 0, 1, 2, or 3; and wherein a 3-, 4-, 5-, 6-, 7-, or 8-membered heterocyclic moiety, wherever it occurs, can optionally be substituted with from one to three substituents which are not further substituted and which are independently selected from the group consisting of —CN, thio, halo, hydroxy, $C_{6-10}$aryl, $C_{1-5}$alkyl, $C_{2-6}$ alkenyl, $C_{3-6}$cycloalkyl, 5- or 6-membered heterocycloalkyl containing 1-3 heteroatoms selected from O, N, and S, $CO_2H$, $CO_2C_{1-6}$alkyl, $C(O)C_{1-6}$alkyl, $CO_2NH_2$, $CO_2NHC_{1-6}$ alkyl, and —$CO_2N(C_{1-6}$alkyl$)_2$.

In various embodiments, disclosed are methods of using compounds of Formula I, II or III that have SeH instead of SH.

In various embodiments, the administration improves one or more symptoms of a neurodegenerative disorder or excitotoxicity disorder. In various embodiments, the one or more symptom is diminished motor function, mobility, cognitive ability, or other symptoms of an excitotoxicity disorder. In one embodiment, one or more symptoms include diminished motor function, mobility, cognitive ability, or other symptoms of an excitotoxicity disorder.

In various embodiments, the small thiol compound exhibits neuroprotective effects in a neuronal tissue-culture model of excitotoxicity, oxidative stress, glutamate overstimulation, elevated intracellular calcium, GABA receptor function, mitochondrial stress or the consequences of these phenomena.

In various embodiments, the small thiol compound or its oxidized equivalent improves cell-viability, reduces calcium transport, relieves mitochondrial stress, enhances mitophagy, modulates GABA activity, modulates glutamate activity or inhibits voltage-gated calcium channel activity in a subject.

In various embodiments, the thiol compound; i) reduces levels of ROS in the CNS; ii) increases intracellular cysteine and the sum of all intracellular low-molecular weight thiols; iii) reduces weak metal-protein interactions through binding of unchaperoned metal-ions; and/or iv) reduces intracellular protein aggregation that is dependent on oxidation of cysteine.

Also contemplated herein is a composition comprising a capton as described herein, (e.g., in FIG. 1 or 2, Formulas I, II or II, Table A, and as described in the Detailed Description), the composition optionally comprising a pharmaceutically acceptable carrier, excipient or diluent. A composition comprising a capton and optionally a pharmaceutically acceptable carrier is contemplated for use in any one of the methods herein.

DETAILED DESCRIPTION

Figure 1:
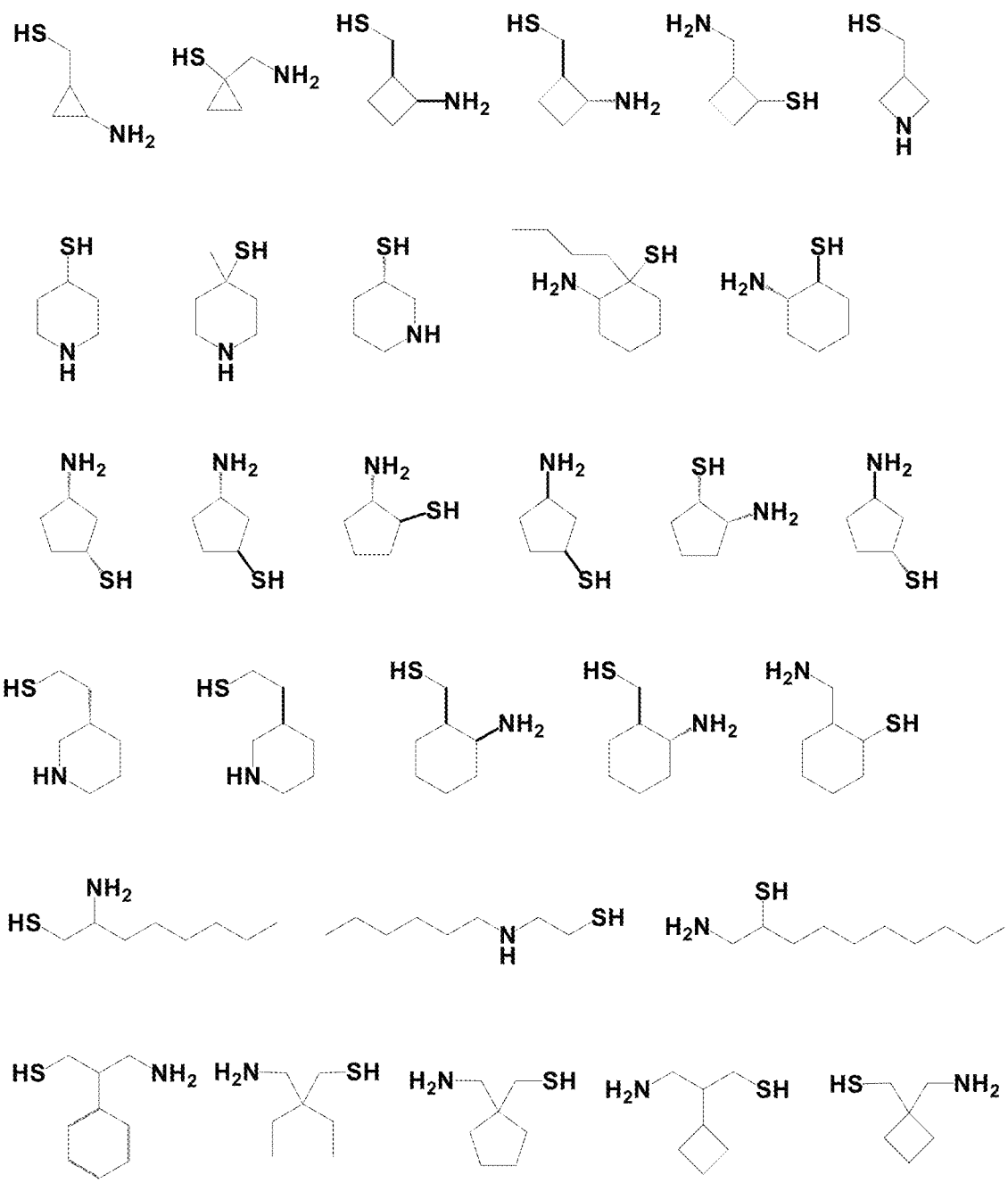
FIG. 1 depicts representative capton compounds.
Figure 1:
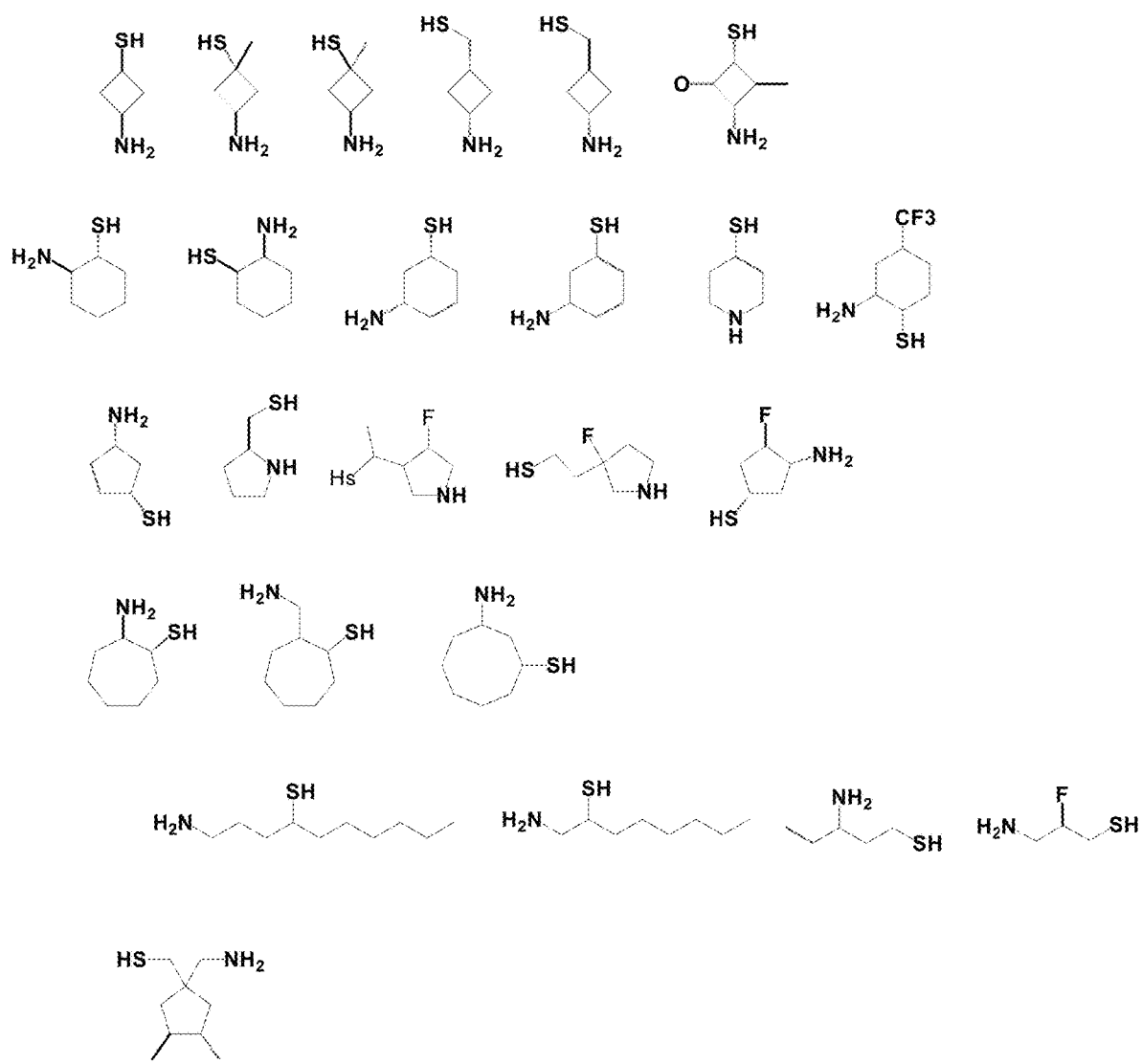

It is contemplated herein that intracellular capton thiols may mitigate oxidation-dependent protein aggregation through reductive mechanisms acting on disulfides and other oxidized sulfur species. Protein aggregation is a fundamental feature of neurodegeneration. Protein-specific assays have been developed to measure aggregation in neurons as a result of oxidative stress, a key driver of aggregation for at least three pathogenic proteins, SOD1, tau and TDP-43. Captons may reduce or reverse aggregation directly or indirectly. Stabilized by a proximate, positively-charged amine, the capton thiol is more acidic than endogenous, low-molecular weight thiols, resulting in elevated thiolate levels under physiological conditions. This feature may have consequences on the kinetics of intracellular disulfide exchange, increasing reduction rates. Paradoxically, a free capton thiolate is thermodynamically-favored. This combination of kinetic and thermodynamic effects will render the capton an effective catalyst of disulfide exchange, allowing disulfide networks to efficiently access lower energy configurations.

Oxidation of capton thiols by ROS is catalyzed by metal ions, including copper, iron and zinc (65-68). Loss of metal homeostasis is a hallmark of ALS (35,36), Alzheimer's and Parkinson's diseases (38,69,70). Thiols bind strongly to copper, iron and zinc. Aminothiols are good metal binders, a result of chelation effects when both sulfur and nitrogen heteroatoms participate in metal complex formation. One mechanism by which the present captons may work is through interaction of captons with free metal ions. Captons may act directly with free metal ions in the extracellular space of the brain through ligand-metal coordination or indirectly by catalyzing the oxidation of thiols.

Definitions

As used herein and in the appended claims, the singular forms "a," "and," and "the" include plural referents unless the context clearly dictates otherwise. Thus, for example, reference to "a derivative" includes a plurality of such derivatives and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

The following references provide one of skill with a general definition of many of the terms used in this disclosure: Singleton, et al., DICTIONARY OF MICROBIOL- OGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

As used herein a "capton", "small thiol", "small diffusible thiol" or "small diffusible aminothiol" refers generally to a low-molecular weight thiol selected for reactivity, metabolic stability, pharmacokinetic persistence and oral bioavailability. Captons are characterized by their similarity to analogs of the neurotransmitter GABA (γ-aminobutyric acid), the structurally-related amino acid taurine (2-aminoethane-1-sulfonate) or known glutamatergic agents. Captons differ from true GABA and taurine analogs by the presence of a thiol in place of the required oxoanion functionality, typically a carboxylate (as found in GABA itself) or a sulfonate (as found in taurine itself). Unique among aminothiols with molecular weight <500 daltons, or even 300 daltons, captons have taurinergic, GABAergic, calcium channel inhibiting, glutamatergic or other neurologic activity after thiol oxidation. Captons may have the following characteristics: small thiol compound, <500 daltons, log P >0.8, tPSA <90.

As used herein "tPSA" refers to total polar surface area (tPSA), which is significantly lower in a capton having a thiol substitution than without it (e.g., in a structurally similar GABA analog or target). tPSA >90 signifies an inability to cross the BBB, and, in general, the higher the tPSA number, the lower brain penetration. Oxidization of thiol-substituted compounds increases tPSA, and increases in tPSA that occur after BBB crossing (e.g., in the oxidized thiol form) are advantageous by delaying clearance of the compound from the subject.

As used herein, a "therapeutically effective amount" or "effective amount" refers to that amount of a small diffusible thiol composition that is oxidized to a sulfinic acid or sulfonic acid after crossing the blood brain barrier, sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In various embodiments, a therapeutically effective amount of the compound ameliorates one or more symptoms associated with various neurodegenerative diseases or excitotoxicity disorders, including but not limited to, bradykinesia, dystonia, psychiatric episodes, including depression, diminished motor function, mobility, cognitive ability, or other symptoms of an excitotoxicity disorder.

"Treatment" refers to prophylactic treatment or therapeutic treatment. In certain embodiments, "treatment" refers to administration of a compound or composition to a subject for therapeutic or prophylactic purposes.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

"Diagnostic" refers to identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in a subject animal, including humans and mammals. In various embodiments, a pharmaceutical composition comprises a therapeutically effective amount of diffusible small thiol compound, optionally another biologically active agent, and optionally a pharmaceutically acceptable excipient, carrier or diluent. In various embodiments, a pharmaceutical composition comprises a therapeutically effective amount of an agent that inhibits the glutamate/cystine transporter $x_c^-$, and optionally a pharmaceutically acceptable excipient, carrier or diluent.

Optionally, the two agents may be in the same pharmaceutical composition. In one embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

As used herein "pharmaceutically acceptable" or "pharmacologically acceptable" salt, ester or other derivative of an active agent comprise, for example, salts, esters or other derivatives refers to a material that is not biologically or otherwise undesirable, i.e., the material may be administered to an individual without causing any undesirable biological effects or without interacting in a deleterious manner with any of the components of the composition in which it is contained or with any components present on or in the body of the individual.

As used herein, the term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human.

Captons

Captons are small and hydrophobic, with low polar-surface areas, extended plasma residence and minimal protein binding. For example, a capton is <500 daltons, log P >0.8, and exhibits a TPSA <90. These characteristics allow the captons to cross the blood-brain barrier. Like many thiols, captons are sensitive to reactive-oxygen species (ROS). Electron transfer neutralizes ROS, simultaneously moving the capton sulfur into higher oxidation states (80-84). Capton sulfinate and sulfonate oxidation products are favored in the extracellular space, or wherever the ratio of ROS-to-thiol is high ((84,85). High ROS-to-thiol ratios are created and sustained by glutamate-driven excitotoxic stress, a cause of neurodegeneration (86-90). ROS-neutralizing agents, like captons, with the tolerability and pharmacokinetics necessary to be drugs, are of interest for the clinical management of neurodegenerative diseases.

Captons are also characterized by their similarity to analogs of the neurotransmitter GABA (γ-aminobutyric acid) and the structurally-related amino acid, taurine (2-aminoethane-1-sulfonate). Some of these analogs are known to those skilled in the art and some are novel (7-15). As stated above captons differ from true GABA and taurine analogs by the presence of a thiol in place of obligate oxoanion functionality, typically a carboxylate (as found in GABA) or a sulfonate (as found in taurine). This substitution will render captons inactive in GABAergic or taurinergic assays. However, oxidation of the capton thiol to a sulfonate uncovers GABAergic or taurinergic function, in some cases generating analogs with previously-demonstrated activity (see, for example, (3R)-piperidine-3-thiol to piperidine-3-sulfonate, piperidine-4-thiol to piperidine-4-sulfonate, (+/−)-trans-1-aminocyclohexane-2-thiol to trans-1-aminocyclohexane-2-sulfonate (TAHS), trans-2-aminocyclopentane-1-thiol to trans-2-aminocyclopentane-1-sulfonate (TAPS), 3-amino-2-(4-chlorophenyl)propane-1-thiol to saclophen (7,8), trans-1-aminocyclobutane-3-thiol to trans-1-aminocyclutane-3-sulfonate) (7-15). Unique among aminothiols with molecular weight <300 daltons, captons have GABAergic or taurinergic activity after thiol oxidation. These characteristics differentiate captons from other thiols that may have been described previously.

Thiols are often uncharged at physiological pH, giving them higher volumes of distribution ($V_d$) compared to anionic congeners, especially zwitterionic anions paired with positively-charged amines, common amongst known GABAergic (2, 20, 29 119) and calcium channel-blocking drugs (gabapentinoids (115)). The thiol or selenol will mobilize cysteine by cleaving blood-borne cystine. ROS generated at the site of neuropathology will then convert the thiol or selenol to a sulfinate, sulfonate or seleninate, neutralizing the ROS and generating a very close anionic analog of the original therapeutic molecule, if not an exact copy of the original therapeutic molecule (often sulfonates). Combining the effects of pre and post-oxidized captons, administration will lead to cysteine replenishment, ROS destruction and introduction of a therapeutic molecule acting on GABA, glutamate, calcium or other neurologic pathways only at the site of excess ROS production (pathogenic) and in amounts proportional to the actual level of the oxidative stressor. It is hypothesized herein that this effectively constitutes a method for in situ dose-metering by the disease-generated insult only in affected areas. It is contemplated that any therapeutic molecule with a functionally-important anionic moiety, from the group including carboxylate, sulfinate, sulfonate, seleninate, phosphate, or phosphonate, can be administered in the form of a distant analog in which a thiol or selenol is substituted for the anionic group.

As described, some oxidized captons, with sulfur oxidation numbers of 2 (sulfinate) and 4 (sulfonate), have the necessary functionality to be active in GABA, taurine, calcium transport and other pathways. These oxidized captons ("o-captons" or "ocaptons") can be analogs of GABA, taurine or the gabapentinoids (17,21,91-114). GABA is the primary inhibitory neurotransmitter in the CNS. GABA analogs are zwitterions and unable to cross the blood-brain barrier. Captons are not zwitterions and have been shown to cross the blood-brain barrier or can be reasonably expected to cross the blood-brain barrier, after which they can be oxidized to zwitterionic, GABAergic, aminosulfonates. ROS-mediated capton conversion is self-limiting, since ROS is consumed in the reaction and localized, and since high ROS levels primarily occur in tissues weakened by pathogenic stress. Not to be bound by theory, it is hypothesized that oxidized captons can potentiate GABA signaling in at least four ways: Direct activation of GABA receptors through orthosteric engagement of the GABA binding site; inhibition of GABA reuptake from the synapse by GABA transporters, extending receptor exposure to the agonist; inhibition of GABA metabolism by 4-aminobutyrate transaminase; and, finally, inhibition of the pre-synaptic voltage-gated calcium channel (VGCC), disfavoring release of excitatory neurotransmitters. The relative levels of glutamate and GABA impacts glutamate excitotoxicity (115, 116). GABA receptor activation lowers the sensitivity of neurons to glutamate post-synaptically, reducing excitotoxic stress.

The beneficial effects of oxidized captons are complementary to those of their cognate capton thiols. A cognate pair, deriving from a single drug molecule, offer access to a broad set of therapeutic activities. Some forms of neurodegeneration seem promising candidates for capton intervention, with fundamental contribution to the disease state from mitochondrial dysfunction (e.g., triggered by excess intracellular calcium), excessive ROS generation, redox-dependent protein aggregation and hyperactivation of glutamate signalling pathways (countered by GABAergic and taurinergic activity).

PCT/US2016/040637 discloses that certain of the compounds contemplated therein may be useful to treat excitotoxicity disorders that result from excess glutamate being secreted by various cells, including immune cells and neurons, in the brain. PCT/US2016/040637 describes that certain agents are capable of inhibiting glutamate-induced excitotoxicity in St-HdhQ$^{111/111}$ cells. The assay used in PCT/US2016/040637 measures cell survival after glutamate induced excitotoxicity. The assay cannot, however, measure the effect of the compounds on neurotransmission including GABAergic, glutamatergic or calcium channel modulating effects.

In various embodiments, the capton can be a compound having the structure of Formula (I) or a disulfide thereof:

Formula I $$\text{HS} \overset{R^4 \quad R^3}{\underset{R^1 \quad R^2}{\diagup\diagdown}} G, \quad (I)$$

wherein:
R$^1$ and R$^2$ are independently selected from the group consisting of H and C$_{1-5}$alkyl; or
R$^1$ and R$^2$, taken together with the carbon atom to which they are attached, form a 3-, 4-, 5-, 6-, 7-, or 8-membered carbocyclic ring;
R$^3$ and R$^4$ are independently selected from the group consisting of H and C$_{1-5}$alkyl; or
R$^3$ and R$^4$, taken together with the carbon atom to which they are attached, form a 3-, 4-, 5-, 6-, 7-, or 8-membered carbocyclic ring;
G is selected from the group consisting of —NR$^5$R$^6$ and —CR$^7$R$^8$NR$^5$R$^6$-
R$^5$ and R$^6$ are independently selected from the group consisting of H and C$_{1-5}$alkyl; or
R$^5$ and R$^6$, taken together with the nitrogen atom to which they are attached, form a 3-, 4-, 5-, 6-, 7-, or 8-membered heterocyclic ring;
R$^7$ and R$^8$ are independently selected from the group consisting of H and C$_{1-5}$alkyl; or
R$^7$ and R$^8$, taken together with the carbon atom to which they are attached, form a 3-, 4-, 5-, 6-, 7-, or 8-membered carbocyclic ring;
R$^2$ and R$^6$, taken together with the atoms to which they are attached, optionally form a 4-5-, 6-, 7-, 8-, 9-, or 10-membered heterocyclic ring;
R$^4$ and R$^6$, taken together with the atoms to which they are attached, optionally form a 4-, 5-, 6-, 7-, 8-, 9-, or 10-membered heterocyclic ring;
R$^4$ and R$^8$, taken together with the atoms to which they are attached, optionally form a 3-4-, 5-, 6-, 7-, or 8-membered carbocyclic ring;
R$^2$ and R$^8$, taken together with the atoms to which they are attached, optionally form a 3-4-, 5-, 6-, 7-, or 8-membered carbocyclic ring;
R$^2$ and R$^4$, taken together with the atoms to which they are attached, optionally form a 3-4-, 5-, 6-, 7-, or 8-membered carbocyclic ring;
wherein a C$_{1-5}$alkyl moiety, wherever it occurs, can optionally comprise a double bond; and
wherein a C$_{1-5}$alkyl, 3-, 4-, 5-, 6-, 7-, or 8-membered carbocyclic or heterocyclic moiety, wherever it occurs, can optionally be substituted with from one to three substituents which are not further substituted and which are independently selected from the group consisting of —CN, thio, halo, hydroxy, C$_{6-10}$ aryl, C$_{1-6}$alkyl, C$_{2-6}$alkenyl, C$_{3-6}$cycloalkyl, 5- or 6-membered heterocloalkyl containing 1-3 heteroatoms selected from O, N, and S, CO$_2$H, CO$_2$C$_{1-6}$alkyl, C(O)C$_{1-6}$alkyl, CO$_2$NH$_2$, CO$_2$NHC$_{1-6}$alkyl, and —CO$_2$N(C$_{1-6}$alkyl)$_2$.

In some cases, when G is —NH$_2$, at least one of R$^1$, R$^2$, R$^3$, and R$^4$ is other than H.

In some cases, R$^5$ and R$^6$ are independently selected from the group consisting of H, methyl, and ethyl. In some cases, R$^5$ and R$^6$, taken together with the nitrogen atom to which they are attached, form a 5-membered heterocyclic ring.

In some cases, wherein R$^4$ is methyl and/or R$^3$ is methyl. In some cases, R$^3$ and R$^4$, taken together with the carbon atom to which they are attached, form a 3-membered carbocyclic ring.

In some cases, R$^2$ is methyl and/or R$^1$ is methyl. In some cases, R$^1$ and R$^2$, taken together with the carbon atom to which they are attached, form a 3-membered carbocyclic ring.

In some cases, G is —CR$^7$R$^8$NR$^5$R$^6$, and R$^2$ and R$^6$, taken together with the atoms to which they are attached, form a 6-membered heterocyclic ring. In some cases, R$^5$ is methyl.

In some cases, G is —NR$^5$R$^6$, and R$^2$ and R$^6$, taken together with the atoms to which they are attached, form a 4- or 6-membered heterocyclic ring. In some cases, R$^5$ is H.

In some cases, R$^7$ and R$^8$ are both H.

In some cases, SH is replaced by SeH.

A compound of Formula I includes, but is not limited to, the following compounds:

-continued

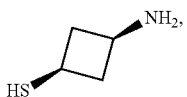

and disulfides thereof.

In some cases, the compound of Formula I has the structure of Formula Ia, Ib, Ic, Id, or Ie:

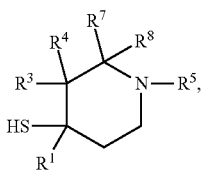
(Ia)

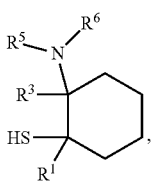
(Ib)

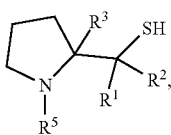
(Ic)

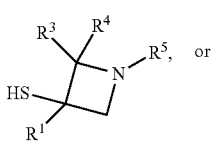
(Id)

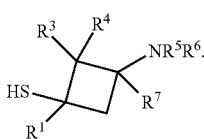
(Ie)

In some cases, $R^1$, $R^2$, $R^3$, $R^4$, $R^5$, $R^6$, $R^7$, and $R^8$ are independently selected from the group consisting of H and $C_{1-5}$alkyl. In some cases, $R^1$, $R^2$, $R^3$, $R^4$, $R^5$, $R^6$, $R^7$, and $R^8$ are independently selected from the group consisting of H and methyl.

In some cases, the capton can be a compound having the structure of Formula II, or a disulfide thereof:

HS-L-NR$^9$R$^{10}$ (II), wherein:

L is a hydrocarbon linking group;
$R^9$ and $R^{10}$ are independently selected from the group consisting of H, $C_{1-5}$alkyl, and CO($C_{1-5}$alkyl); or
$R^9$ and $R^{10}$, taken together with the nitrogen atom to which they are attached, form a 3-, 4-, 5-, 6-, 7-, or 8-membered heterocyclic ring;
wherein a $C_{1-5}$ alkyl moiety, wherever it occurs, can optionally comprise a double bond; and
wherein a $C_{1-5}$ alkyl, 3-, 4-, 5-, 6-, 7-, or 8-membered carbocyclic or heterocyclic moiety, wherever it occurs, can optionally be substituted with from one to three substituents which are not further substituted and which are independently selected from the group consisting of —CN, thio, halo, hydroxy, $C_{6-10}$aryl, $C_{1-5}$alkyl, $C_{2-6}$alkenyl, $C_{3-6}$cycloalkyl, 5- or 6-membered heterocycloalkyl containing 1-3 heteroatoms selected from O, N, and S, $CO_2H$, $CO_2C_{1-6}$alkyl, $C(O)C_{1-6}$alkyl, $CO_2NH_2$, $CO_2NHC_{1-6}$alkyl, and —$CO_2N(C_{1-6}alkyl)_2$.

In some cases, the compound of Formula II is not cysteamine.

In some cases, L is a 3-, 4-, 5-, 6-, 7-, or 8-membered cycloalkyl ring or a 6-membered aryl ring. In some cases, L is $C_{1-5}$alkyl. In some cases, L is substituted with one to four groups selected from halo, $C_{1-5}$alkyl, $C_{3-5}$cycloalkyl, and —$CO_2(C_{1-5}alkyl)$.

In some cases, the capton is a compound having the structure of Formula (III):

(III)

wherein:
A is a 3 to 8 membered heterocyclic ring containing one N atom;
n is 0, 1, 2, or 3; and
wherein a 3-, 4-, 5-, 6-, 7-, or 8-membered heterocyclic moiety, wherever it occurs, can optionally be substituted with from one to three substituents which are not further substituted and which are independently selected from the group consisting of —CN, thio, halo, hydroxy, $C_{6-10}$aryl, $C_{1-5}$alkyl, $C_{2-6}$ alkenyl, $C_{3-6}$cycloalkyl, 5- or 6-membered heterocycloalkyl containing 1-3 heteroatoms selected from O, N, and S, $CO_2H$, $CO_2C_{1-6}$alkyl, $C(O)C_{1-6}$alkyl, $CO_2NH_2$, $CO_2NHC_{1-6}$alkyl, and —$CO_2N(C_{1-6}alkyl)_2$.

In some cases, A is a 3-, 4-, 5-, 6-, 7-, or 8-membered monocyclic heterocycloalkyl ring, a 6-, 7-, or 8-membered bicyclic heterocycloalkyl ring, or a 5- or 6-membered heteroaryl ring.

In some cases, the compound of formula III has a structure IIIa:

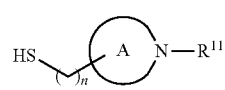
(IIIa)

wherein $R^{11}$ is selected from the group consisting of H and $C_{1-5}$alkyl.

In some cases, A is substituted with one to four groups selected from halo, $C_{1-5}$alkyl, $C_{3-5}$cycloalkyl, and —$CO_2(C_{1-5}alkyl)$.

Figure 2:
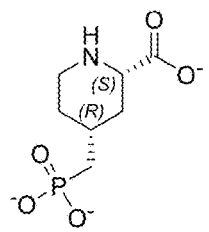
FIG. 2 shows additional capton compounds, including the effect of thiol substitution (of the original oxoanion molecule) on the blood brain barrier (BBB) penetration aptitude (log P and total polar surface area). tPSA >90 signifies an inability to cross the BBB. Typically, the higher the tPSA, the lower brain penetration. Oxidization of thiol-substituted compounds increases tPSA.
Figure 2:
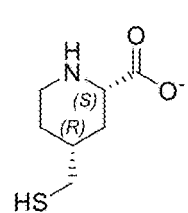
Figure 2:
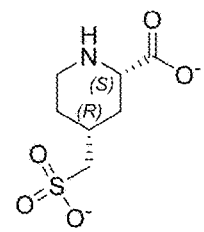
Figure 2:
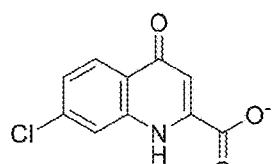
Figure 2:
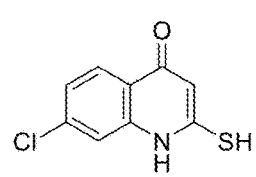
Figure 2:
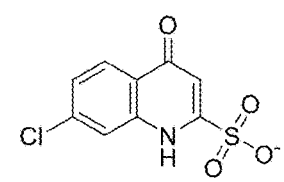
Figure 2:
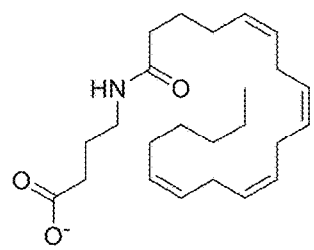
Figure 2:
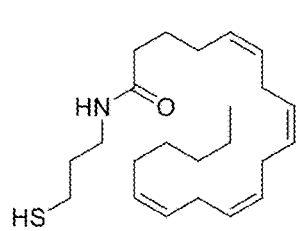
Figure 2:
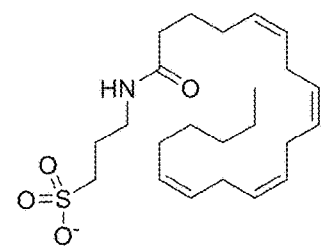
Figure 2:
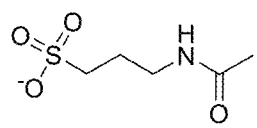
Figure 2:
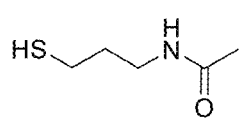
Figure 2:
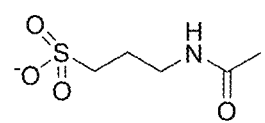
Figure 2:
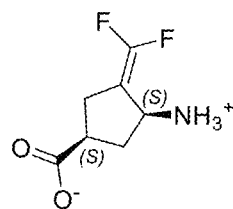
Figure 2:
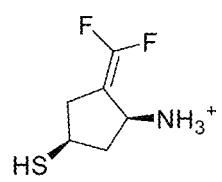
Figure 2:
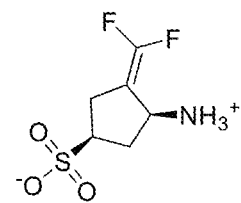
Figure 2:
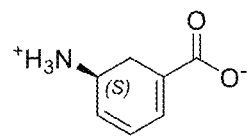
Figure 2:
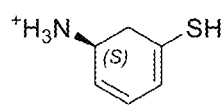
Figure 2:
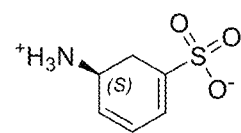
Figure 2:
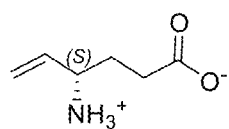
Figure 2:
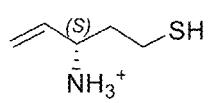
Figure 2:
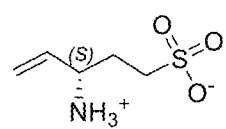
Figure 2:
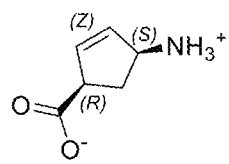
Figure 2:
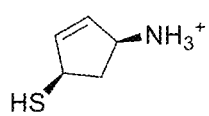
Figure 2:
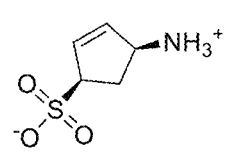
Figure 2:
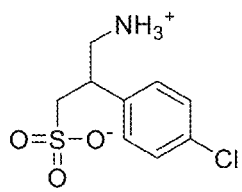
Figure 2:
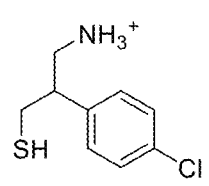
Figure 2:
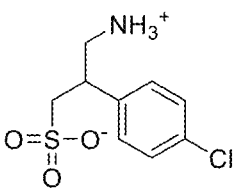

Compounds contemplated herein also include, but are not limited to those set out in FIGS. 1 and 2.

Specific compounds contemplated include compounds in the following Table.

The compound can be a compound as listed in Table A, or a pharmaceutically acceptable salt thereof.

TABLE A

| Compound No. | Structure |
| --- | --- |
| 1 | *(2S)-2-amino-2-[(1R,2S)-2-sulfanylcyclopropyl]acetic acid)* |
| 2 | *(decahydroisoquinoline-3-carboxylic acid derivative with 4-chloro-2-(sulfanylmethyl)benzamide)* |
| 3 | *(cysteine: HS-CH₂-CH(NH₂)-COOH)* |
| 4 | *(4-sulfanyl-1-neopentylpiperidine)* |
| 5 | *(2-fluoro-3-amino-1-propanethiol)* |
| 6 | *(ethyl-substituted tetrahydropyrano-carbazole with CH₂SH and ethyl)* |
| 7 | *(E)-N-(2-sulfanylphenyl)-3-(4-pentylphenyl)acrylamide* |
| 8 | H₂N–(CH₂)₃–NH–(CH₂)₂–SH |
| 9 | HS–CH₂–CH₂–CH(NH₂)–CH₂–SH |
| 10 | HS–CH₂–CH₂–NH₂ |
| 11 | HS–CH₂–CH₂–NH–C(=NH)–NH₂ |

TABLE A-continued

| Compound No. | Structure |
|---|---|
| 12 | 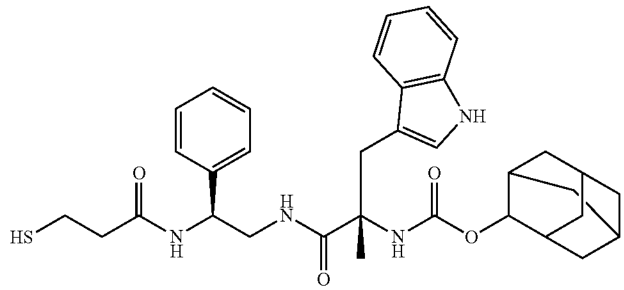 [SMILES: C[C@@](Cc1c[nH]c2ccccc12)(NC(=O)OC1C2CC3CC(C2)CC1C3)C(=O)NC[C@@H](NC(=O)CCS)c1ccccc1] |
| 13 | 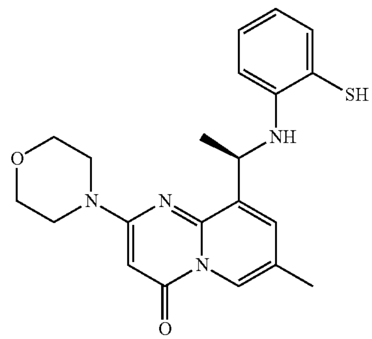 [SMILES: Cc1cc([C@@H](C)Nc2ccccc2S)c2nc(N3CCOCC3)cc(=O)n2c1] |
| 14 | 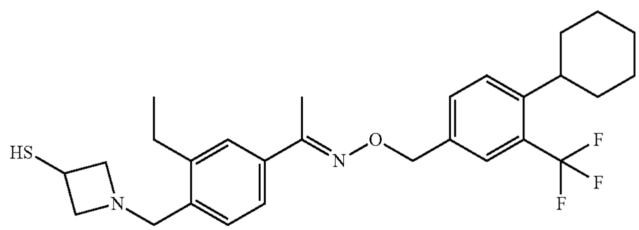 [SMILES: CCc1cc(/C(C)=N/OCc2ccc(C3CCCCC3)c(C(F)(F)F)c2)ccc1CN1CC(S)C1] |
| 15 | 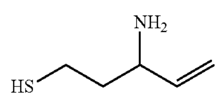 |
| 16 | 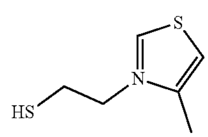 |
| 17 | 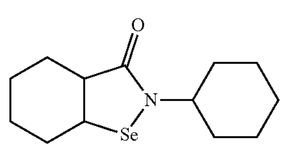 [SMILES: O=C1C2CCCCC2[Se]N1C1CCCCC1] |
| 18 | 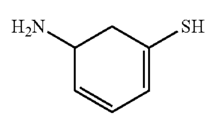 |
| 19 | 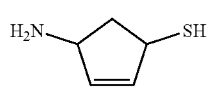 |
| 20 | 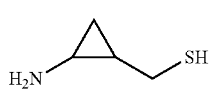 |

TABLE A-continued
| Compound No. | Structure |
|---|---|
| 21 | 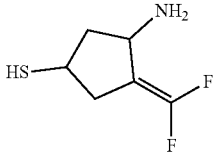 |
| 22 | 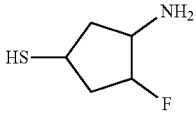 |
| 23 | 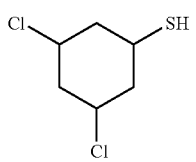 |
| 24 | 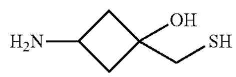 |
| 25 | 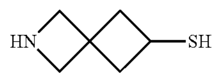 |
| 26 | 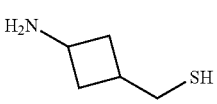 |
| 27 | 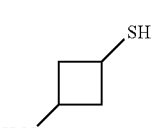 |
| 28 | 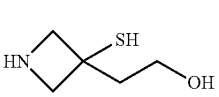 |
| 29 | 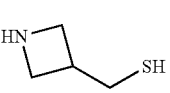 |
| 30 | 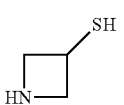 |
| 31 | 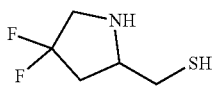 |
| 32 | 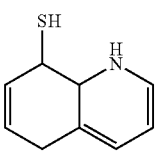 [SMILES: SC1C=CCC2=CC=CNC21] |
| 33 | 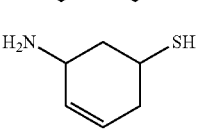 |

TABLE A-continued

| Compound No. | Structure |
|---|---|
| 34 | cyclohexadiene with NH₂ and SH |
| 35 | 2-azabicyclo[2.2.1] with SH |
| 36 | 2-aminocyclopentane-1-thiol |
| 37 | 4-(trifluoromethyl)-2-aminocyclohexane-1-thiol |
| 38 | 1-(aminomethyl)-1-(mercaptomethyl)cyclobutane |
| 39 | 2-cyclobutyl-3-mercaptopropan-1-amine |
| 40 | 2-(aminomethyl)cyclobutane-1-thiol |
| 41 | 2-(mercaptomethyl)cyclobutan-1-amine |
| 42 | 2-aminocyclobutane-1-thiol |
| 43 | 1-amino-5-mercapto-2,3-dihydro-1H-indene-1-carboxylic acid |
| 44 | 3-aminocyclohexane-1-thiol |
| 45 | 3-aminocyclopentane-1-thiol |

TABLE A-continued

| Compound No. | Structure |
|---|---|
| 46 | 4-amino-cyclohexane-1-thiol (H2N and SH trans on cyclohexane) |
| 47 | 3-(hydroxymethyl)piperidine-3-thiol |
| 48 | 2-(piperidin-3-yl)ethane-1-thiol |
| 49 | (piperidin-3-yl)methanethiol |
| 50 | piperidine-3-thiol |
| 51 | (pyrrolidin-2-yl)methanethiol |
| 52 | (1-mercaptocyclopropyl)methanamine |
| 53 | (1-aminocyclopropyl)methanethiol |
| 54 | 1-cyclopropylpiperidine-4-thiol |
| 55 | 8-azabicyclo[3.2.1]octane-3-thiol |
| 56 | 2-(aminomethyl)cyclohexane-1-thiol |
| 57 | 2-(mercaptomethyl)cyclohexan-1-amine |
| 58 | (1S,2S)-2-aminocyclohexane-1-thiol |

TABLE A-continued

| Compound No. | Structure |
| --- | --- |
| 59 | cycloheptane with SH and CH2NH2 substituents on adjacent carbons |
| 60 | cycloheptane with SH and NH2 on adjacent carbons |
| 61 | cyclopentane with geminal CH2NH2 and CH2SH |
| 62 | cyclooctane with SH and NH2 substituents |
| 63 | cyclohexane with geminal CH2NH2 and CH2SH |
| 64 | phenyl-CH(CH2NH2)(CH2SH) |
| 65 | cyclohexanethiol |
| 66 | 4-(pyrrolidin-1-ylmethyl)piperidine-4-thiol |
| 67 | 2-(pyrrolidin-1-yl)ethanethiol |
| 68 | 2-(piperidin-2-yl)ethanethiol |
| 69 | (piperidin-2-yl)methanethiol |
| 70 | azepane-3-thiol |

TABLE A-continued

| Compound No. | Structure |
|---|---|
| 71 | azetidine-N-CH2CH2-SH |
| 72 | quinuclidine with SH at bridgehead |
| 73 | quinuclidin-3-yl-SH |
| 74 | imidazolidine-2-thione |
| 75 | 4-(mercaptomethyl)piperidine-2-carboxylic acid |
| 76 | imidazolidine-2-thiol |
| 77 | (azetidin-2-yl)methanethiol |
| 78 | 4,4-difluoro-3-mercaptopiperidine |
| 79 | 3-mercaptopiperidine-4-carboxylic acid |
| 80 | 3-fluoro-4-mercaptopiperidine |
| 81 | piperidine-4-thiol |
| 82 | 2-(3-fluoropyrrolidin-3-yl)ethane-1-thiol |
| 83 | pyrrolidine-3-thiol |

TABLE A-continued

| Compound No. | Structure |
| --- | --- |
| 84 | 4-(mercaptomethyl)piperidin-4-ol |
| 85 | 2-(piperidin-4-yl)ethane-1-thiol |
| 86 | piperidin-4-ylmethanethiol |
| 87 | piperidine-4-thiol |
| 88 | morpholin-3-ylmethanethiol |
| 89 | thiomorpholine |
| 90 | 5-(2-mercaptoethyl)-1,5,8-triazabicyclo[4.2.0]oct-7-ene-7,8-dione derivative |
| 91 | 1-amino-4-((4-acetamidophenyl)amino)-2-mercaptoanthracene-9,10-dione |
| 92 | N-(3-mercaptopropyl)acetamide |
| 93 | S-(piperidin-4-yl) ethanethioate |
| 94 | S-(2-aminoethyl) ethanethioate |

TABLE A-continued

| Compound No. | Structure |
|---|---|
| 95 | 1-tert-butyl-4-mercaptopiperidine |
| 96 | 1-amino-2-methylpropane-2-thiol |
| 97 | 2-amino-2-methylpropane-1-thiol |
| 98 | (S)-2-((9-isopropyl-6-((3-chloro-4-mercaptophenyl)amino)-9H-purin-2-yl)amino)-3-methylbutan-1-ol |
| 99 | 4-chloro-N-(4-(3-mercapto-6-isopropylazulen-1-yl)butyl)benzenesulfonamide |
| 100 | 2-amino-7-isopropyl-3-mercapto-5H-chromeno[2,3-b]pyridin-5-one |
| 101 | 1-isobutyl-4-mercaptopiperidine |
| 102 | N-(8-(2-mercaptoethyl)-8-azabicyclo[3.2.1]octan-3-yl)-1-isopropyl-2-oxo-1,2-dihydroquinoline-3-carboxamide |
| 103 | 1-isopropyl-4-mercaptopiperidine |

TABLE A-continued

| Compound No. | Structure |
|---|---|
| 104 | 4-mercaptophenyl-2-amino-2-methylacetic acid (HS-C6H4-C(CH3)(NH2)-COOH) |
| 105 | 4-fluoro-3-(1-mercaptoethyl)pyrrolidine |
| 106 | 1-mercapto-2-aminopropane (CH3-CH(NH2)-CH2-SH) |
| 107 | 3-amino-1-methyl-1-mercaptocyclobutane |
| 108 | 3-methyl-3-mercaptopiperidine |
| 109 | 3-methyl-3-mercaptopyrrolidine |
| 110 | 4-methyl-4-mercaptopiperidine |
| 111 | 4-methyl-4-(methylthio)piperidine |
| 112 | 3-methyl-3-mercaptoazetidine |
| 113 | 3,3-dimethyl-4-mercaptopiperidine |
| 114 | 1-({2-mercapto-2-(4-methylphenyl)cyclopropyl}methyl)-4-phenylpiperidin-4-ol |

TABLE A-continued

| Compound No. | Structure |
|---|---|
| 115 | 2,6-dichloro-3-methyl-N-(2-mercaptophenyl)aniline |
| 116 | (1-(aminomethyl)-3,4-dimethylcyclopentyl)methanethiol |
| 117 | 6-methylpiperidine-4-thiol |
| 118 | 6-methylpiperidine-3-thiol |
| 119 | 4-methylpiperidine-3-thiol |
| 120 | 3-methylpiperidine-4-thiol |
| 121 | 2-(methylamino)butane-1-thiol |
| 122 | (1,8-diethyl-1,3,4,9-tetrahydropyrano[3,4-b]indol-1-yl)methanethiol |
| 123 | 2-amino-1-propylcyclohexane-1-thiol |
| 124 | 3-(2-methyloctan-2-yl)-6,6-dimethyl-9-mercapto-6a,7,10,10a-tetrahydro-6H-benzo[c]chromen-1-ol |
| 125 | 1-amino-4-mercaptodecane |

TABLE A-continued
| Compound No. | Structure |
|---|---|
| 126 | 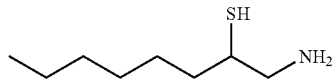 |
| 127 | 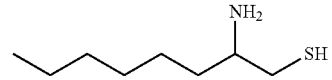 |
| 128 | 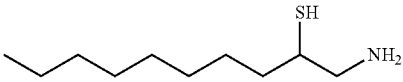 |
| 129 | 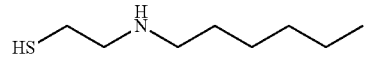 |
| 130 | 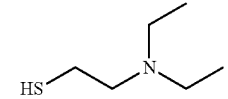 |
| 131 | 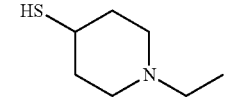 |
| 132 | 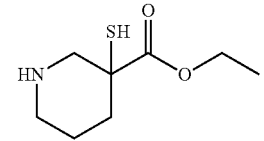 |
| 133 | 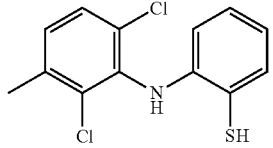 |
| 134 | 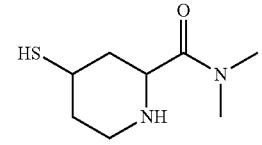 |
| 135 | 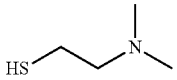 |
| 136 | 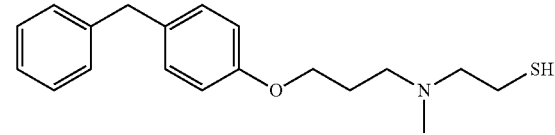 [SMILES: CN(CCS)CCCOc1ccc(Cc2ccccc2)cc1] |
| 137 | 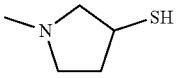 |
| 138 | 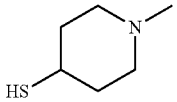 |

TABLE A-continued

| Compound No. | Structure |
|---|---|
| 139 | 1-methylpiperidine-3-thiol |
| 140 | 3-(methylamino)cyclobutane-1-thiol |
| 141 | 1-(3,4-dihydroxyphenyl)-2-(methylamino)ethane-1-thiol |
| 142 | 2-(methylamino)ethane-1-thiol |
| 143 | methyl 5-mercaptopiperidine-3-carboxylate |
| 144 | (3-((6-methoxynaphthalen-2-yl)oxy)methyl)-3-mercaptoazetidin-1-yl)(4-fluorophenyl)methanone |
| 145 | (1-(methylsulfonyl)piperazin-3-yl)methanethiol |
| 146 | 2-(methylthio)ethan-1-amine |
| 147 | 2-((3-(trifluoromethyl)phenyl)amino)benzenethiol |
| 148 | 2-((3-(trifluoromethyl)phenyl)amino)benzenethiol |

TABLE A-continued

| Compound No. | Structure |
| --- | --- |
| 149 | 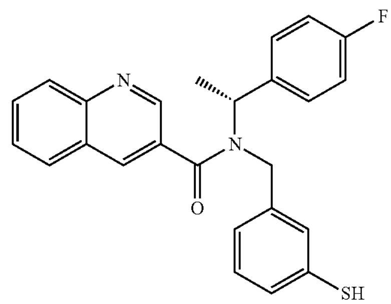 [SMILES: C[C@H](c1ccc(F)cc1)N(Cc1cccc(S)c1)C(=O)c1cnc2ccccc2c1] |
| 150 | 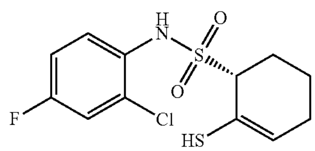 [SMILES: O=S(=O)(Nc1ccc(F)cc1Cl)[C@@H]1CCCC=C1S] |
| 151 | 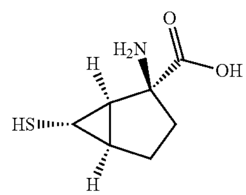 [SMILES: N[C@@]1(C(=O)O)CC[C@H]2[C@H](S)[C@H]21] |
| 152 | 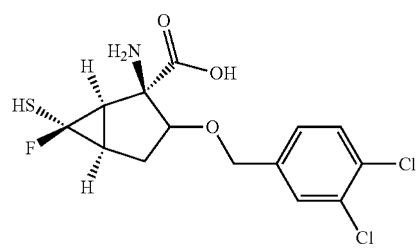 [SMILES: N[C@@]1(C(=O)O)C(OCc2ccc(Cl)c(Cl)c2)C[C@@H]2[C@H]1[C@@]2(F)S] |
| 153 | 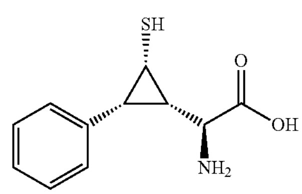 [SMILES: N[C@H](C(=O)O)[C@H]1[C@@H](S)[C@H]1c1ccccc1] |
| 154 | 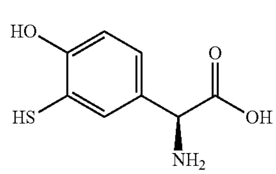 [SMILES: N[C@H](C(=O)O)c1ccc(O)c(S)c1] |
| 155 | 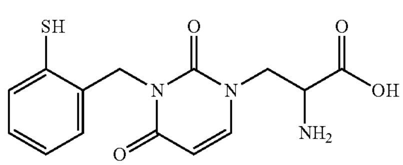 [SMILES: NC(Cn1ccc(=O)n(Cc2ccccc2S)c1=O)C(=O)O] |
| 156 | 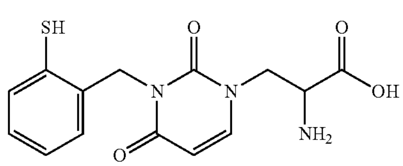 [SMILES: NC(Cn1ccc(=O)n(Cc2ccccc2S)c1=O)C(=O)O] |

TABLE A-continued

| Compound No. | Structure |
| --- | --- |
| 157 | 4-chlorophenyl with CH(CH2NH2)(CH2SH) substituent |
| 158 | bicyclo[3.1.0]hexane with NH2, COOH, and SH substituents |
| 159 | 1-amino-1-carboxy-5-mercapto-indane |
| 160 | 4-chlorophenyl with CH(CH2NH2)(CH2SH) substituent |
| 161 | 2'-chloro-biphenyl with CH2SH and CH2CH(NH2)COOH substituents |
| 162 | 4-(mercaptomethyl)piperidine-2-carboxylic acid |
| 163 | N-[(1R)-1-(4-fluorophenyl)ethyl]-N-(3-mercaptobenzyl)quinoline-3-carboxamide |

TABLE A-continued

| Compound No. | Structure |
| --- | --- |
| 164 | 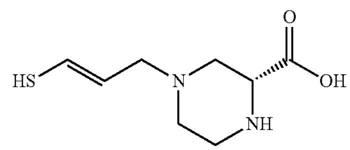 [SMILES: O=C(O)[C@H]1CN(C/C=C/S)CCN1] |
| 165 | 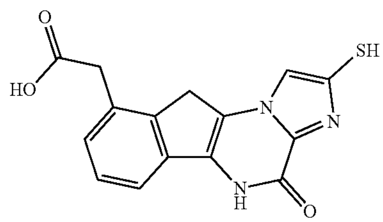 [SMILES: O=C(O)Cc1cccc2c1Cc1c-2[nH]c(=O)c2nc(S)cn12] |
| 166 | 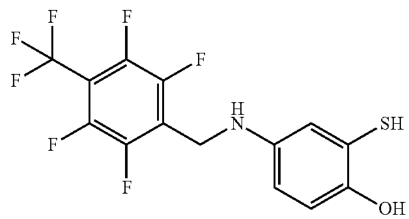 [SMILES: Oc1ccc(NCc2c(F)c(F)c(C(F)(F)F)c(F)c2F)cc1S] |
| 167 | 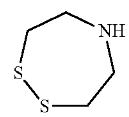 |
| 168 | 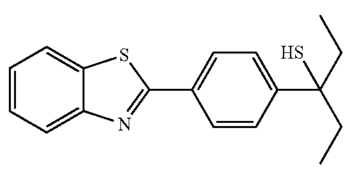 [SMILES: CCC(S)(CC)c1ccc(-c2nc3ccccc3s2)cc1] |
| 169 | 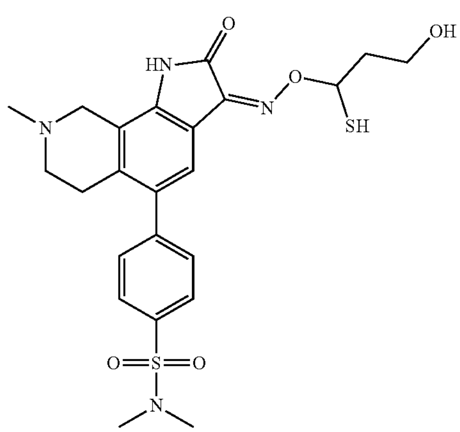 [SMILES: CN1CCc2c(-c3ccc(S(=O)(=O)N(C)C)cc3)cc3c(c2C1)NC(=O)/C3=N\OC(S)CCO] |
| 170 | 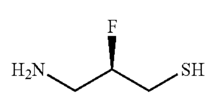 |
| 171 | 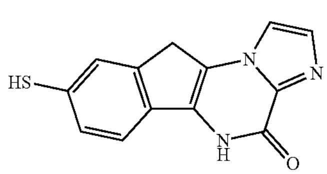 [SMILES: O=c1[nH]c2c(n3ccnc13)Cc1cc(S)ccc1-2] |

TABLE A-continued

| Compound No. | Structure |
|---|---|
| 172 | 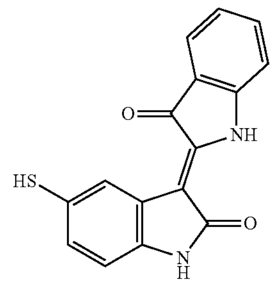 [SMILES: O=C1Nc2ccc(S)cc2/C1=C1/Nc2ccccc2C1=O] |
| 173 | 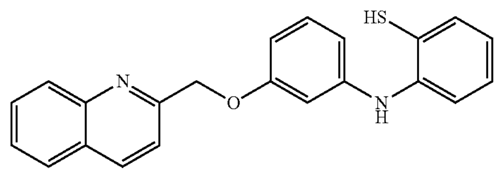 [SMILES: Sc1ccccc1Nc1cccc(OCc2ccc3ccccc3n2)c1] |
| 174 | 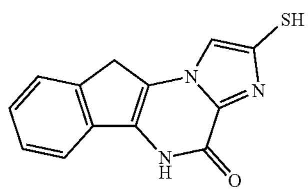 [SMILES: O=c1[nH]c2c(n3cc(S)nc13)Cc1ccccc1-2] |
| 175 | 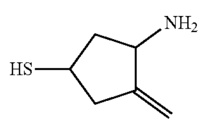 |
| 176 | 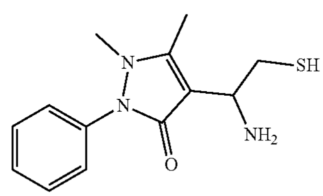 [SMILES: Cc1c(C(N)CS)c(=O)n(-c2ccccc2)n1C] |
| 177 | 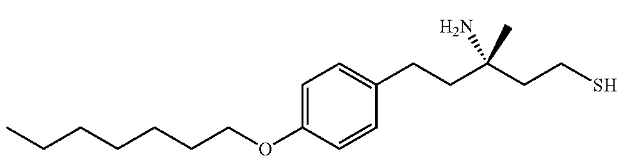 [SMILES: CCCCCCCOc1ccc(CC[C@](C)(N)CCS)cc1] |
| 178 | 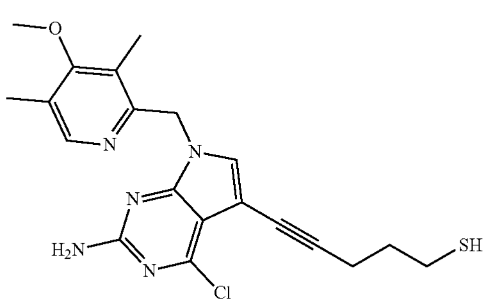 [SMILES: COc1c(C)cnc(Cn2cc(C#CCCCS)c3c(Cl)nc(N)nc32)c1C] |

TABLE A-continued

| Compound No. | Structure |
|---|---|
| 179 | (structure) |
| 181 | (structure) |
| 182 | (structure) |
| 183 | (structure) |
| 184 | (structure) |
| 185 | (structure) |
| 186 | (structure) |

TABLE A-continued

| Compound No. | Structure |
|---|---|
| 187 | 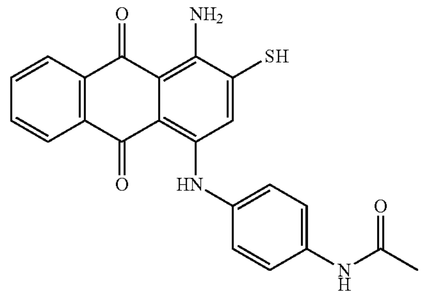 [SMILES: CC(=O)Nc1ccc(Nc2cc(S)c(N)c3c2C(=O)c2ccccc2C3=O)cc1] |
| 188 | 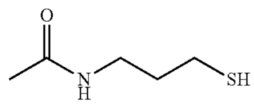 |
| 189 | 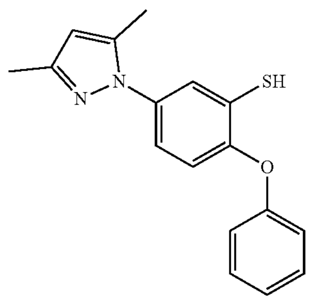 [SMILES: Cc1cc(C)n(-c2ccc(Oc3ccccc3)c(S)c2)n1] |
| 190 | 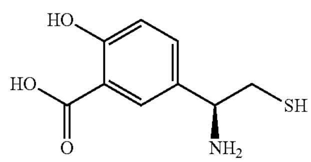 [SMILES: N[C@H](CS)c1ccc(O)c(C(=O)O)c1] |
| 191 | 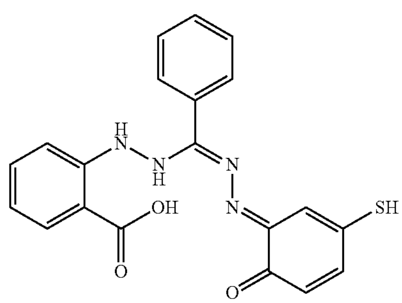 [SMILES: O=C1C=CC(S)=C/C1=N\N=C(/NNc1ccccc1C(=O)O)c1ccccc1] |
| 192 | 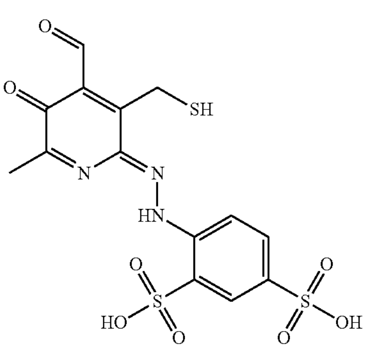 [SMILES: CC1=N/C(=N\Nc2ccc(S(=O)(=O)O)cc2S(=O)(=O)O)C(CS)=C(C=O)C1=O] |

TABLE A-continued

| Compound No. | Structure |
| --- | --- |
| 193 | 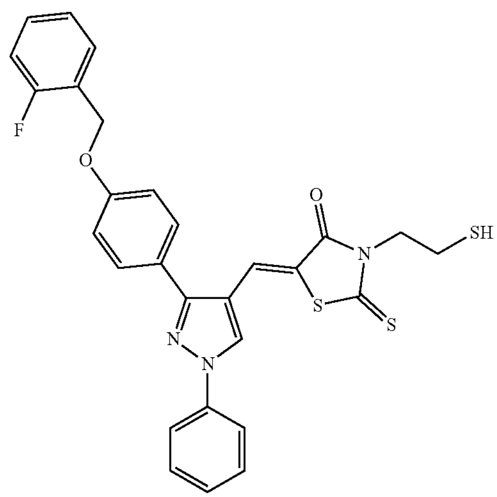 [SMILES: O=C1/C(=C/c2cn(-c3ccccc3)nc2-c2ccc(OCc3ccccc3F)cc2)SC(=S)N1CCS] |
| 194 | 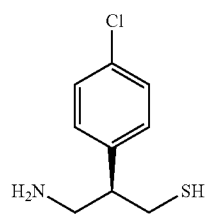 [SMILES: NC[C@H](CS)c1ccc(Cl)cc1] |
| 196 | 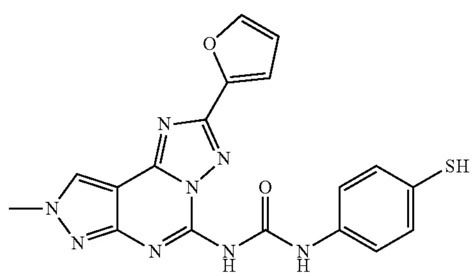 [SMILES: Cn1cc2c(nc(NC(=O)Nc3ccc(S)cc3)n3nc(-c4ccco4)nc23)n1] |
| 197 | 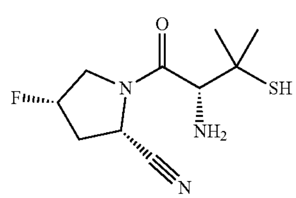 [SMILES: CC(C)(S)[C@H](N)C(=O)N1C[C@@H](F)C[C@H]1C#N] |
| 198 | 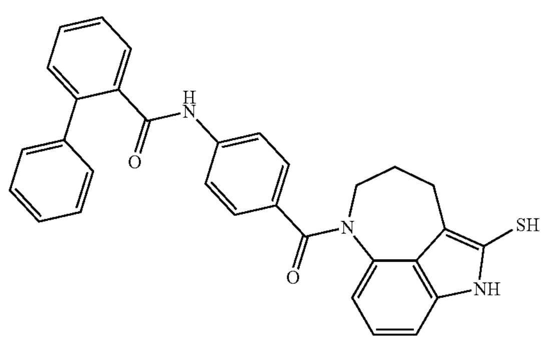 [SMILES: O=C(Nc1ccc(C(=O)N2CCCc3c(S)[nH]c4cccc2c34)cc1)c1ccccc1-c1ccccc1] |

TABLE A-continued

| Compound No. | Structure |
| --- | --- |
| 199 | 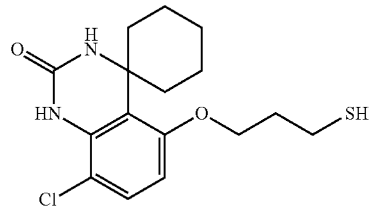 [SMILES: O=C1Nc2c(Cl)ccc(OCCCS)c2C2(CCCCC2)N1] |
| 200 | 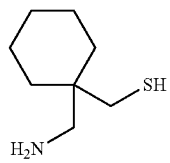 |
| 201 | 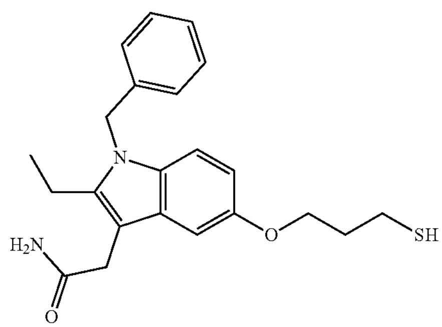 [SMILES: CCc1c(CC(N)=O)c2cc(OCCCS)ccc2n1Cc1ccccc1] |
| 202 | 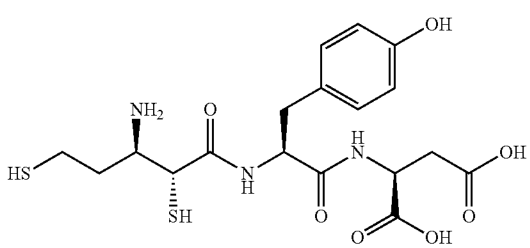 [SMILES: N[C@H](CCS)[C@@H](S)C(=O)N[C@@H](Cc1ccc(O)cc1)C(=O)N[C@@H](CC(=O)O)C(=O)O] |
| 203 | 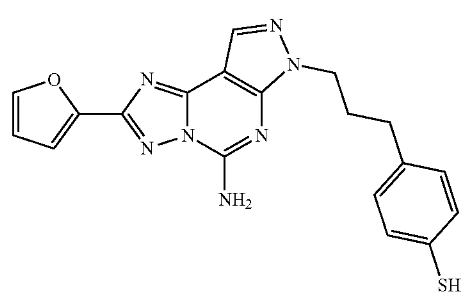 [SMILES: Nc1nc2c(cnn2CCCc2ccc(S)cc2)c2nc(-c3ccco3)nn12] |
| 204 | 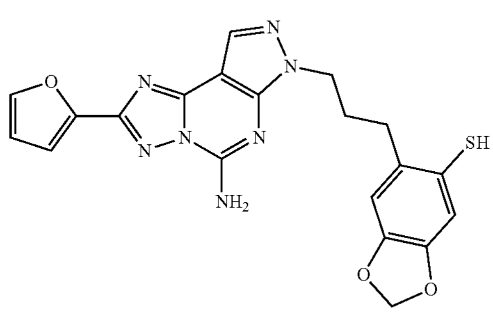 [SMILES: Nc1nc2c(cnn2CCCc2cc3c(cc2S)OCO3)c2nc(-c3ccco3)nn12] |

TABLE A-continued

| Compound No. | Structure |
|---|---|
| 205 | 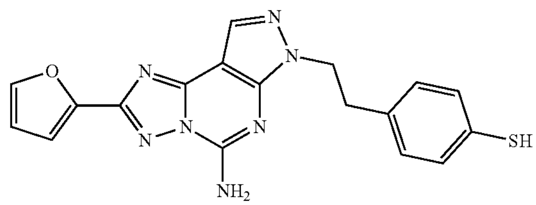 [SMILES: Nc1nc2c(cnn2CCc2ccc(S)cc2)c2nc(-c3ccco3)nn12] |
| 206 | 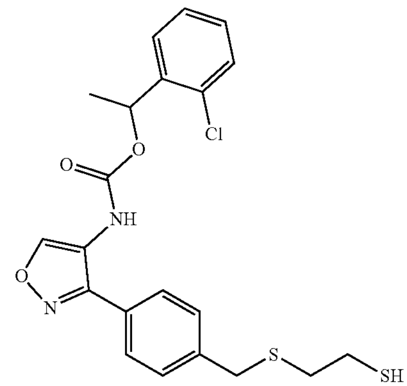 [SMILES: CC(OC(=O)Nc1conc1-c1ccc(CSCCS)cc1)c1ccccc1Cl] |
| 207 | 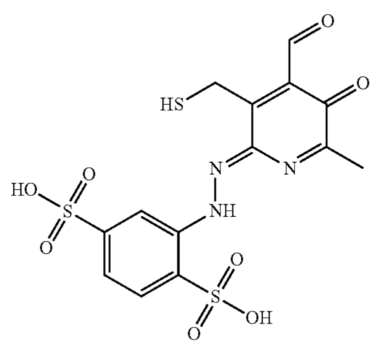 [SMILES: CC1=N/C(=N\Nc2cc(S(=O)(=O)O)ccc2S(=O)(=O)O)C(CS)=C(C=O)C1=O] |
| 208 | 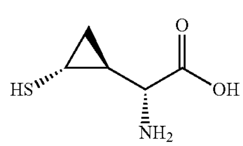 |
| 209 | 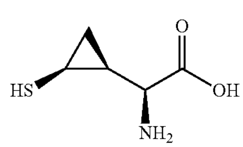 |
| 210 | 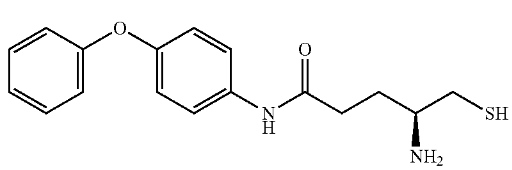 [SMILES: N[C@H](CS)CCC(=O)Nc1ccc(Oc2ccccc2)cc1] |

TABLE A-continued

| Compound No. | Structure |
| --- | --- |
| 211 | 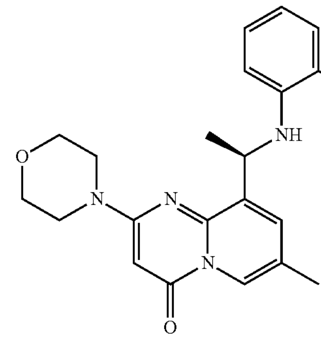 |
| 212 | 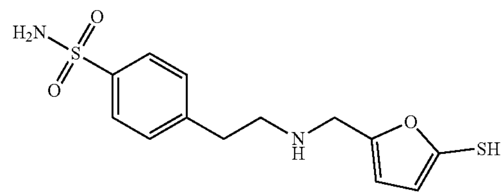 [SMILES: NS(=O)(=O)c1ccc(CCNCc2ccc(S)o2)cc1] |
| 213 | 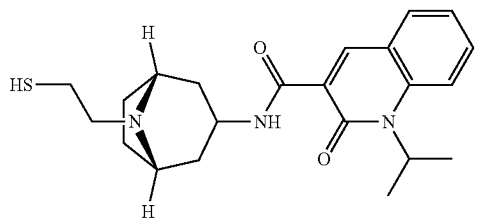 [SMILES: CC(C)n1c(=O)c(C(=O)NC2C[C@H]3CC[C@@H](C2)N3CCS)cc2ccccc21] |
| 214 | 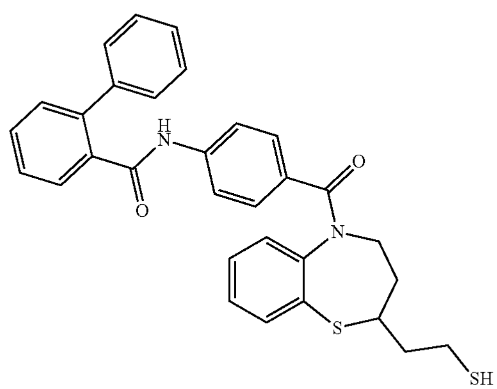 [SMILES: O=C(Nc1ccc(C(=O)N2CCC(CCS)Sc3ccccc32)cc1)c1ccccc1-c1ccccc1] |
| 215 | 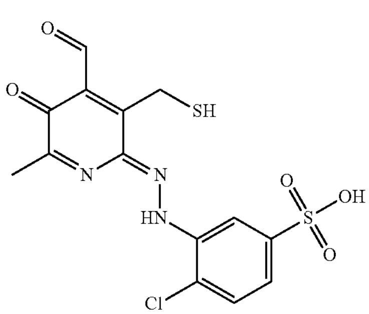 [SMILES: CC1=N/C(=N\Nc2cc(S(=O)(=O)O)ccc2Cl)C(CS)=C(C=O)C1=O] |

TABLE A-continued

| Compound No. | Structure |
| --- | --- |
| 216 | 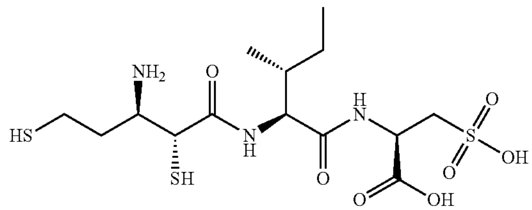 [SMILES: CC[C@@H](C)[C@H](NC(=O)[C@H](S)[C@H](N)CCS)C(=O)N[C@@H](CS(=O)(=O)O)C(=O)O] |
| 217 | 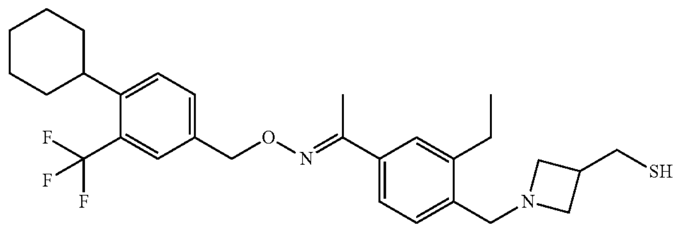 [SMILES: CCc1cc(/C(C)=N/OCc2ccc(C3CCCCC3)c(C(F)(F)F)c2)ccc1CN1CC(CS)C1] |
| 218 | 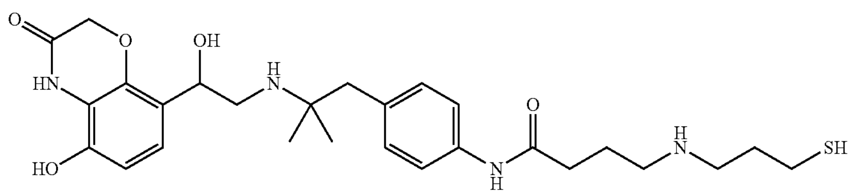 [SMILES: CC(C)(Cc1ccc(NC(=O)CCCNCCCS)cc1)NCC(O)c1ccc(O)c2c1OCC(=O)N2] |
| 219 | 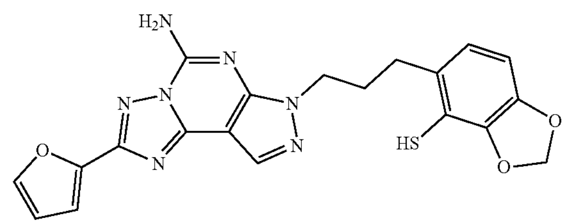 [SMILES: Nc1nc2c(cnn2CCCc2ccc3c(c2S)OCO3)c2nc(-c3ccco3)nn12] |
| 220 | 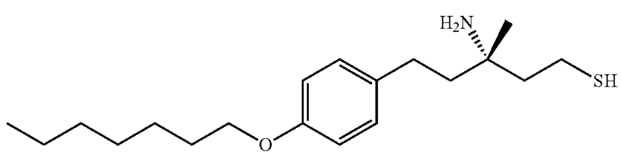 [SMILES: CCCCCCCOc1ccc(CC[C@](C)(N)CCS)cc1] |
| 221 | 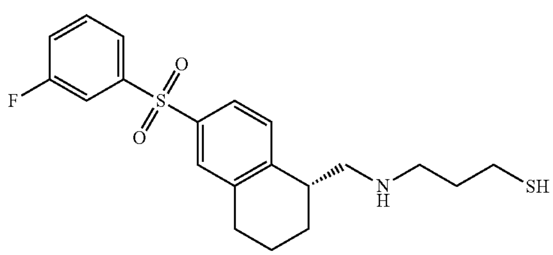 [SMILES: O=S(=O)(c1cccc(F)c1)c1ccc2c(c1)CCC[C@H]2CNCCCS] |
| 222 | 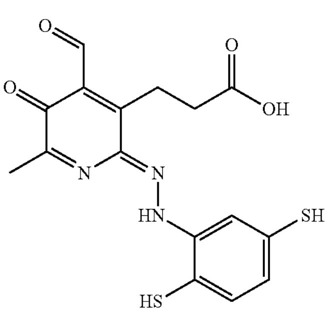 [SMILES: CC1=N/C(=N\Nc2cc(S)ccc2S)C(CCC(=O)O)=C(C=O)C1=O] |

TABLE A-continued

| Compound No. | Structure |
|---|---|
| 223 | 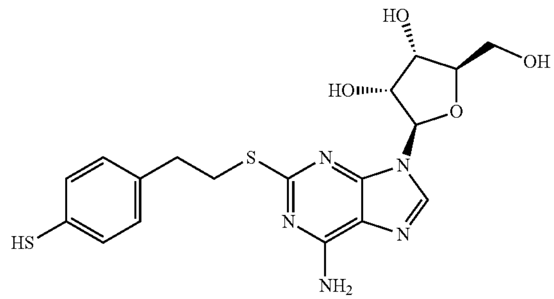 [SMILES: Nc1nc(SCCc2ccc(S)cc2)nc2c1ncn2[C@@H]1O[C@H](CO)[C@@H](O)[C@H]1O] |
| 224 | 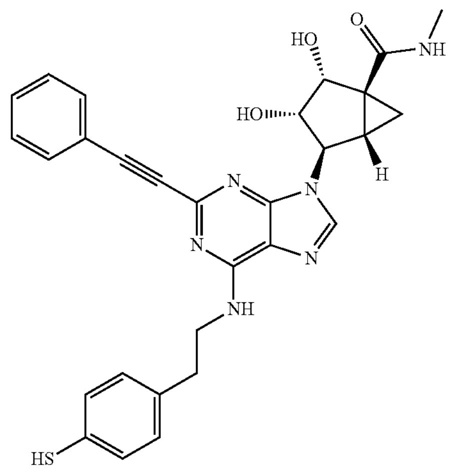 [SMILES: CNC(=O)[C@@]12C[C@@H]1[C@@H](n1cnc3c(NCCc4ccc(S)cc4)nc(C#Cc4ccccc4)nc31)[C@H](O)[C@@H]2O] |
| 225 | 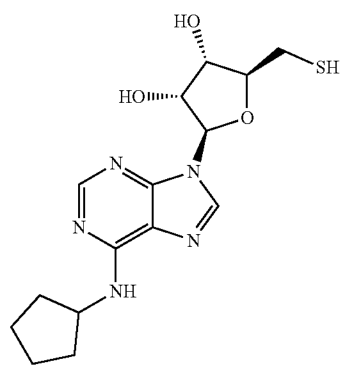 [SMILES: O[C@@H]1[C@H](O)[C@@H](CS)O[C@H]1n1cnc2c(NC3CCCC3)ncnc21] |
| 226 | 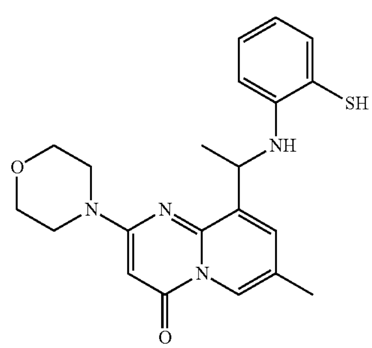 [SMILES: Cc1cc(C(C)Nc2ccccc2S)c2nc(N3CCOCC3)cc(=O)n2c1] |

Methods of Use

It is contemplated herein that captons are useful to counter the effects of ROS in the brain of subjects having a neurodegenerative disease, as well as provide neuroprotection for, or prevent or ameliorate future neurodegeneration mediated by, activity in which trauma to the brain may occur, e.g., as in traumatic brain injury and chronic traumatic encephalopathy.

TBI and CTE

Traumatic brain injury (TBI) is an acute condition, often caused by blunt force trauma to the head. Damage results from longitudinal and shearing forces on neurons and, particularly, long axonal tracts throughout the brain. These forces can lead to gross structural compromise and cell death. Dead neurons release large amounts of glutamate into the extracellular space, along with the rest of their contents. Elevated glutamate causes persistent activation of glutamate receptors with uncontrolled influx of calcium and other cations (90). Systems that reestablish ionic balance are overwhelmed, consuming considerable amounts of ATP in the process. Excess calcium also leads to mitochondrial depolarization, forcing increased flux through the electron-transport chain and its inevitable consequence, reaction-oxygen-species (ROS). Toxic levels of ROS deplete cellular antioxidant systems necessary for survival (117-120). Uncontrolled calcium levels and depolarization of membrane potentials cause organellar dysfunction, most critically the release of mitochondrial cytochrome C and apoptotic cell-death (62,121-124). Capton mechanisms bolster endogenous antioxidant pools, deplete cells of ROS and reduce neuronal sensitivity to glutamate as previously described in this application. Captons may be a useful way to address the acute phase of TBI.

Acute TBI may be followed by a sustained, subacute, but progressive, secondary phase. The slower phase resembles other progressive neurodegenerative conditions, like amyotrophic lateral sclerosis (ALS), Alzheimer's disease and fronto-temporal dementia (FTD). Multiple impacts sustain the secondary phase and result in a condition known as chronic traumatic encephalopathy (CTE). CTE has a high prevalence among professional athletes and combat veterans, who often suffer repetitive, concussive brain trauma (52, 117, 125). Glutamate hyperexcitation, calcium imbalance and elevated ROS, which underlie acute TBI, continue to figure prominently in CTE pathology, with a significant additional contribution from protein aggregation (50,52,126, 127). Intracellular, pathogenic, protein aggregates, observed in most neurodegenerative diseases, are a hallmark of CTE. CTE aggregates are specifically enriched in tau and TDP-43, both proteins that can adopt pathogenic conformations that seed further misfolding and are, consequently, transmissible. Aggregation of tau and TDP-43 require ROS, with inter-protein oxidative disulfide formation a necessary component (44,54,56,128). Captons neutralize ROS and, as stable thiolates, efficiently cleave disulfides. Insoluble TDP-43 has been shown to be solubilized by thiol agents, potentially reversing aggregates (44). Therefore, captons may be potentially useful in the treatment of CTE, the consequence of chronic TBI.

Excitotoxicity Disorders

Excitotoxicity disorders result from excessive glutamate release in the central nervous system resulting in glutamate toxicity to the surrounding cells. Glutathione is a tripeptide made of glutamate-cysteine-glycine and is an important buffer of oxidative stress in the brain. GSH is synthesized from extracellular cystine taken up via the glutamate:cystine exchange transporter $x_c^-$ and converted back to two cysteine molecules within the reductive environment of the cell. The cysteines can then be incorporated into glutathione. The $x_c^-$ transporter, also called the $x_c^-$ antiporter, or xCT, is a $Na^+$-independent cystine-glutamate exchange system that takes up cystine and exports glutamate from the cell in a 1:1 exchange ratio (33).

Glutathione-based antioxidant systems exhibit redundancy with a second system that includes such components as thioredoxin, thioredoxin reductase, TRP14, peroxiredoxin, nicotinamide nucleotide transhydrogenase and reduced nicotinamide adenine dinucleotide cofactors. Sulfur amino acids, incorporated into redox-controlling proteins, are also a key feature of this second anti-oxidant network, which, therefore, also depends on xCT.

Pharmacologically, application of small thiol molecules has been demonstrated to rescue deficits in antioxidant capacity, including complete loss of the GSH-based system. Contemplated herein are methods of treating an excitotoxicity disorder using a compound as disclosed herein. Exemplary excitotoxicity disorders contemplated herein include, but are not limited to, spinal cord injury, stroke or other ischemia, traumatic brain injury, chronic traumatic encephalopathy (CTE), hearing loss, neurodegenerative diseases, multiple sclerosis, Alzheimer's disease, amyotrophic lateral sclerosis (ALS), Parkinson's disease, Huntington's disease, concussion, epilepsy and CNS depressant-withdrawal syndrome.

Huntington's Disease

Huntington's disease (HD) is an adult-onset neurodegenerative disorder for which treatment strategies have helped address certain symptoms of HD, but remain ineffective at truly treating the disease. HD is an autosomal dominant genetic disorder with a prevalence of about 5-10 per 100,000 in the Caucasian population. Clinical symptoms include chorea and behavioral disorders but the most problematic features of the disease are slowly progressive motor dysfunction and impaired cognition (Ha et al., Curr Opin Neurol 25(4):491-8, 2012). The pathology of HD is characterized by the presence of neuritic and intranuclear inclusions in neurons and relatively selective neural loss in the striatum and the deeper layers of the cerebral cortex. HD is caused by a Cytosine-Adenine-Guanine (CAG) triplet repeat expansion in the first exon of the HTT gene leading to an expanded polyglutamine stretch in the huntingtin protein (The Huntington's Disease Collaborative Research Group. A novel gene containing a trinucleotide repeat that is expanded and unstable on Huntington's disease chromosomes. Cell 72(6): 971-83, 1993). HD develops when the polyglutamine expansion exceeds 35, a point that enlarges the polyglutamine stretch past a critical threshold that predisposes to aggregation. There is an inverse correlation between the number of CAG and the age at onset (Andrew et al., Nat Genet 4(4):398-403, 1993). Mutant huntingtin has been implicated in the disruption of many cellular processes, including protein clearance, protein-protein interaction, mitochondrial function, axonal trafficking, N-methyl-D-aspartate receptor activation, gene transcription and post-translational modification (Zuccato et al., Physiol Rev 2010; 90(3):905-81, Labbadia et al., Trends Biochem Sci 2013; 38(8):378-85). Although mutant huntingtin has a widespread distribution in neuronal and non-neuronal tissues, the medium spiny GABAergic neurons of the striatum exhibit the most pronounced vulnerability (Labbadia et al., Trends Biochem Sci 2013; 38(8):378-85).

Huntington's Disease is often defined or characterized by onset of symptoms and progression of decline in motor and neurological function. HD can be broken into five stages:

Patients with early HD (stages 1 and 2) have increasing concerns about cognitive issues, and these concerns remain constant during moderate/intermediate HD (stages 3 and 4). Patients with late-stage or advanced HD (stage 5) have a lack of cognitive ability (Ho et al., Clin Genet. Sep 2011; 80(3):235-239).

Progression of the stages can be observed as follows: Early Stage (stage 1), in which the person is diagnosed as having HD and can function fully both at home and work. Early-Intermediate Stage (stage 2), in which the person remains employable but at diminished capacity and can manage their daily affairs, albeit with some difficulty. Late-Intermediate Stage (stage 3), in which the person can no longer work and/or manage household responsibilities. At this stage, the person may need help to handle daily financial and other affairs. Early-Advanced Stage patients (stage 4) are no longer independent in daily activities but are able to live at home, supported by family or professional caregivers. In the Advanced Stage (stage 5), the person requires complete support in daily activities and professional nursing care. Patients with HD usually die about 15 to 20 years after their symptoms first appear.

In intermediate stages, as the disease progresses, the initial motor symptoms will gradually develop into more obvious involuntary movements such as jerking and twitching of the head, neck, arms and legs. These movements may interfere with walking, speaking and swallowing. People at this stage of Huntington's often look as if they're drunk: they stagger when they walk and their speech is slurred. They have increasing difficulty working or managing a household, but can still deal with most activities of daily living. The advanced stages of HD typically involve fewer involuntary movements and more rigidity. Patients in these stages of HD can no longer manage the activities of daily living. Difficulties with swallowing, communication and weight loss are common in the advanced stage.

Chorea is the most common movement disorder seen in HD. Initially, mild chorea resembles fidgetiness. As the disease progresses, chorea gradually moves towards and is replaced by dystonia and parkinsonian features, such as bradykinesia, rigidity, and postural instability. In advanced disease, patients develop an akinetic-rigid syndrome, with minimal or no chorea, as well as spasticity, clonus, and extensor plantar responses. Dysarthria and dysphagia are common. Abnormal eye movements, tics and myoclonus may be seen in patients with HD. Juvenile HD (Westphal variant), defined as having an age of onset of younger than 20 years, is characterized by parkinsonian features, dystonia, long-tract signs, dementia, epilepsy, and mild or even absent chorea.

Cognitive decline is also characteristic of HD, and the rate of progression can vary among individual patients. Dementia and the psychiatric features of HD are often the earliest of functional impairment. Dementia syndrome associated with HD includes early onset behavioral changes, such as irritability, untidiness, and loss of interest, followed by slowing of cognition, impairment of intellectual function, and memory disturbances. This pattern corresponds well to the syndrome of subcortical dementia, and it has been suggested to reflect dysfunction of frontal-subcortical neuronal circuitry.

Early stages of HD are characterized by deficits in short-term memory, followed by motor dysfunction and a variety of cognitive changes in the intermediate stages of dementia (Loy et al., PLoS Curr. 2013; 5: Cleret de Langavant et al., PLoS One. 2013; 8(4): e61676). These deficits include diminished verbal fluency, problems with attention, executive function, visuospatial processing, and abstract reasoning. Language skills become affected in the final stages of the illness, resulting in marked word-retrieval deficiency.

HD can also manifest in behavioral disorders, including depression, with a small percentage of patients experiencing bouts of mania characteristic of bipolar disorder, an increased rate of suicide, and psychosis, obsessive-compulsive symptoms, sexual and sleep disorders, and changes in personality.

Parkinson's Disease

Parkinson's disease (PD) is a complex neurodegenerative disorder involving the predominant loss of dopaminergic neurons in the substantia nigra pars compacta (SNc), subsequent decay of the nigrostriatal tract and associated movement anomalies such as rigidity, bradykinesia and tremor. Pathological features associated with substantial nigra degeneration include mitochondrial abnormalities, loss of antioxidant enzyme systems and reduced glutathione (GSH) levels (Bharath et al., Biochem Pharmacol. 64:1037-48, 2002).

Stages of a Parkinson's disease patient is described by Hoehn and Yahr in following five distinct stages depending on the symptoms (Hoehn M M, Yahr M D, Parkinsonism: onset, progression and mortality. Neurology 1967, 17:427-42). Stage I: (mild or early disease): symptoms affect only one side of the body. Stage II: both sides of the body are affected, but posture remains normal. Stage Ill: (moderate disease): both sides of the body are affected, and there is mild imbalance during standing or walking, however, the person remains independent. Stage IV: (advanced disease): both sides of the body are affected, and there is disabling instability while standing or walking. The person in this stage requires substantial help. Stage V: severe, fully developed disease is present. The person is restricted to a bed or chair.

Ischemia

Ischemia refers to a condition resulting from a decrease or lack of blood flow and oxygen to a part of the body such as the brain, heart, or other tissue. Ischemic injury refers generally to the damage to a tissue that is distal or otherwise effected by the loss of blood flow and oxygen. Ischemic injury is often a result of the lack of oxygen and fluids, but also includes inflammatory cascades. For example, ischemia and ischemic injury can occur as a result of cardiac, pulmonary or brain injury, organ transplantation or surgical procedure, or a disease or disorder.

Acute ischemia is most often recognized in strokes and cardiac damage. However, there are a number of disorders and injuries that cause ischemic events leading to cell death and tissue damage. Strokes, cerebrovascular events and cardio vascular events are the result of an acute obstruction of cerebral or cardiac blood flow to a region of the brain or heart, respectively. There are approximately 500,000 cases of stroke each year in the United States, of which 30% are fatal, and hence stroke is the third leading cause of death in the United States. Approximately 80% of strokes are "ischemic" and result from an acute occlusion of a cerebral artery with resultant reduction in blood flow. The remainder are "hemorrhagic", which are due to rupture of a cerebral artery with hemorrhage into brain tissue and consequent obstruction of blood flow due to lack of flow in the distal region of the ruptured vessel and local tissue compression, creating ischemia.

Stroke commonly affects individuals older than 65 years. In 1996, the FDA approved the use of tissue plasminogen activator (tPA) as therapy for acute ischemic stroke, based on a limited number of controlled trials. Approximately twenty percent of strokes may involve bleeding within the brain, which damages nearby brain tissue (for example, a hemorrhagic stroke). Hemorrhagic stroke occurs when a blood vessel bursts inside the brain. The brain is sensitive to bleeding and damage can occur rapidly, either because of the presence of the blood itself, or because the fluid increases pressure on the brain and harms it by pressing it against the skull. The surrounding tissues of the brain resist the expansion of the bleeding, which is finally contained by forming a mass (for example, an intracerebral hematoma). Both swelling and hematoma will compress and displace normal brain tissue.

There appears to be a correlation between an early reduction in glutathione levels in ischemia and the activation of lipooxygenases by the inflammatory cascade, which may play a role in ischemia-induced nerve cell loss. In vitro cell culture assays have shown that inhibitors of lipoxygenase 12-LOX block glutamate-induced cell death, and both 5- and 12-LOX inhibitors block ischemic injury in hippocampal slice cultures.

Alzheimer's Disease

Alzheimer's disease (AD) is characterized by chronic, progressive neurodegeneration. Neurodegeneration in AD involves early synaptotoxicity, neurotransmitter disturbances, accumulation of extracellular β-amyloid (Aβ) deposits and intracellular neurofibrils, and gliosis and at later stages loss of neurons and associated brain atrophy (Danysz et al., Br J Pharmacol. 167:324-352, 2012). Early studies indicated Aβ peptides may have the ability to enhance glutamate toxicity in human cerebral cortical cell cultures (Mattson et al., J Neurosci. 12:376-389, 1992; Li et al., J Neurosci. 31(18):6627-38, 2011).

It is contemplated herein that administration of a small thiol composition as described herein in combination with an agent that inhibits the glutamate/cysteine antiporter xv can alleviate or treat one or more symptoms associated with excitotoxicity disease or disorder. Such symptoms, include but are not limited to, one or more motor skills, cognitive function, dystonia, chorea, psychiatric symptoms such as depression, brain and striatal atrophies, and neuronal dysfunction.

It is contemplated that the administration results in a slower progression of total motor score compared to a subject not receiving thiol composition and $x_c^-$ inhibitor. In some embodiments, the slower progression is a result in improvement in one or more motor scores selected from the group consisting of chorea subscore, balance and gait subscore, hand movements subscore, eye movement subscore, maximal dystonia subscore and bradykinesia assessment.

Additional indicia of a slower decline in symptoms of HD are measured using change from baseline in one or more of the following parameters: using standardized tests for (i) functional assessment (e.g., UHDRS Total Functional Capacity, LPAS, Independence Scale); (ii) neuropsychological assessment (e.g., UHDRS Cognitive Assessment, Mattis Dementia Rating Scale, Trail Making Test A and B, Figure Cancellation Test, Hopkins Verbal Learning Test, Articulation Speed Test); (iii) psychiatric assessment (UHDRS Behavioral Assessment, Montgomery and Asberg Depression Rating Scale) and (iv) cognitive assessment (e.g., Dementia Outcomes Measurement Suite (DOMS)).

In certain embodiments, alteration in one or more symptoms in patients receiving small diffusible thiol composition that is oxidized to a sulfinic acid or sulfonic acid after crossing the blood brain barrier is shown to be beneficial by at least 10%, 20%, 25%, 30%, 35%, 40%, 45%, 50%, 55%, 60%, 65%, 70%, 75% or more compared to baseline assessment of the symptom. In certain embodiments, the rate of progression or decline in total motor score is slowed, by at least 20%, 25%, 30%, 35%, 40%, 45%, 50%, 55%, 60%, 65%, 70%, 75% or more. Measurement may be performed using techniques known in the art, e.g., the Unified Huntington Disease Rating Scale (UHDRS), Bradykinesia Ratings Scale, and Lindop Parkinson's Assessment Scale (LPAS).

In certain embodiments, the symptoms are measured at 3 months, 6 months, 12 months, 18 months or 2 years or more after administration.

Provided herein is a method of treating a neurological disease or disorder comprising administering a small thiol compound (e.g., <500 daltons, log P >0.8, TPSA <90) that can be oxidized by reactive-oxygen species after crossing the blood-brain barrier to a sulfinic or sulfonic acid and wherein the oxidized compound possesses GABAergic, calcium channel inhibiting, glutamatergic or other neurologic activity. Also provided is a method of treating an excitotoxicity disorder comprising administering the small thiol compound; a method of treating a neurological disease or disorder characterized by aggregation of TDP-43 comprising administering the small thiol compound; a method of treating a neurological disease or disorder characterized by aggregation of superoxide dismutase 1 (SOD1) protein comprising administering the small thiol compound. In various embodiments, the disease is further characterized by aggregation of tau protein.

Exemplary neurodegenerative or excitotoxicity disorders include amyotrophic lateral sclerosis (ALS), frontotemporal lobar degeneration, traumatic brain injury, chronic traumatic encephalopathy (CTE), Alzheimer's disease, ischemia or epilepsy. Also contemplated is familial or sporadic ALS.

The disclosure also provides a method for slowing the progression of brain and striatal atrophies and/or treating dystonia in a subject suffering from an excitotoxicity disease comprising administering to a subject in need thereof the small thiol composition that is oxidized to a sulfinic acid or sulfonic acid after crossing the blood brain barrier.

Also provided is a method for treating or ameliorating glutamate toxicity in a subject comprising administering an effective amount of a small thiol compound (<500 daltons, log P >0.8, TPSA <90) that can be oxidized by reactive-oxygen species after crossing the blood-brain barrier to a sulfinic or sulfonic acid and where the oxidized compound possesses GABAergic, calcium channel inhibiting, glutamatergic or other neurologic activity. In various embodiments, the administration reduces neuronal glutamate toxicity.

It is contemplated that the small diffusible thiol compound useful in any one of the methods is a capton as described herein. Exemplary captons are set out in FIGS. 1 and 2, in Formulas I, II and III, and described further in the detailed description.

Further provided is a method for slowing the degeneration of neurons in a subject, or a method for treating or ameliorating glutamate toxicity in a subject, comprising administering an effective amount of a compound of Formula I, II or III or a small thiol compound (<500 daltons, log P >0.8, TPSA <90) that can be oxidized by reactive-oxygen species after crossing the blood-brain barrier to a sulfinic or sulfonic acid and where the oxidized compound possesses GABAergic, calcium channel inhibiting, glutamatergic or other neurologic activity.

In various embodiments, the thiol administration improves one or more symptoms of a neurodegenerative disorder or excitotoxicity disorder. Exemplary symptoms include diminished motor function, mobility, cognitive ability, or other symptoms of an excitotoxicity disorder.

The small thiol compound also exhibits neuroprotective effects in a neuronal tissue-culture model of excitotoxicity, oxidative stress, glutamate overstimulation, elevated intracellular calcium, GABA receptor function, mitochondrial stress or the consequences of these phenomena.

In various embodiments, the small thiol compound or its oxidized equivalent improves cell-viability, reduces calcium transport, relieves mitochondrial stress, enhances mitophagy, modulates GABA activity, modulates glutamate activity or inhibits voltage-gated calcium channel activity in a subject.

It is contemplated that the small thiol or capton provides relief in the recited disorders by acting to i) reduce levels of ROS in the CNS; ii) increase intracellular cysteine and the sum of all intracellular low-molecular weight thiols; iii) reduce weak metal-protein interactions through binding of unchaperoned metal-ions; and/or iv) reduce intracellular protein aggregation that is dependent on oxidation of cysteine.

Pharmaceutical Formulations

The disclosure provides for use of small diffusible thiol composition that is oxidized to a sulfinic acid or sulfonic acid after crossing the blood brain barrier in the treatment of neurodegenerative disorders, including excitotoxicity diseases or disorders, such as Huntington's Disease, Parkinson's disease, ischemia, or Alzheimer's disease (e.g., to slow or improve motor skills, cognitive function and promote neuronal regeneration), amyotrophic lateral sclerosis (ALS), familial or sporadic ALS, frontotemporal lobar degeneration, chronic traumatic encephalopathy (CTE), or traumatic brain injury. To administer a small diffusible thiol composition that is oxidized to a sulfinic acid or sulfonic acid after crossing the blood brain barrier to patients or test animals, it is preferable to formulate the therapeutics in a composition comprising one or more pharmaceutically acceptable carriers. Pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any-and-all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The small diffusible thiol composition that is oxidized to a sulfinic acid or sulfonic acid after crossing the blood brain barrier may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Pharmaceutical compositions of the disclosure containing a small diffusible thiol composition that is oxidized to a sulfinic acid or sulfonic acid after crossing the blood brain barrier as an active ingredient may contain pharmaceutically acceptable carriers or additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the disclosure.

Formulation of the pharmaceutical composition will vary according to the route of administration selected (e.g., solution, emulsion). An appropriate composition comprising the small thiol or capton composition to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, the small diffusible thiol composition that is oxidized to a sulfinic acid or sulfonic acid after crossing the blood brain barrier disclosed herein can be lyophilized for storage and reconstituted in a suitable carrier prior to use. Any suitable lyophilization and reconstitution techniques can be employed. It is appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the disclosure provides use of an enterically coated small diffusible thiol composition that is oxidized to a sulfonate upon crossing the blood brain barrier. Enteric coatings prolong release until the product reaches the intestinal tract, typically the small intestine. Because of the enteric coatings, delivery to the small intestine is improved thereby improving uptake of the active ingredient while reducing gastric side effects.

In some embodiments, the coating material is selected such that the therapeutically active agent is released when the dosage form reaches the small intestine or a region in which the pH is greater than pH 4.5. In various embodiments, the formulation releases at a pH of about 4.5 to 6.5, 4.5 to 5.5, 5.5 to 6.5 or about pH 4.5, 5.0, 5.5, 6.0 or 6.5.

The coating may be a pH-sensitive material, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5. For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine. In order to provide predictable dissolution corresponding to the small intestine transit time of about 3 hours (e.g., 2-3 hours) and permit reproducible release therein, the coating should begin to dissolve at the pH range within the small intestine. Therefore, the amount of enteric polymer coating should be sufficient to substantially dissolved during the approximate three-hour transit time within the small intestine, such as the proximal and mid-intestine.

Dosing and Administration

The small diffusible thiol composition that is oxidized to a sulfinic acid or sulfonic acid after crossing the blood brain barrier is administered in a therapeutically effective amount; typically, in unit dosage form. The amount of product administered is, of course, dependent on the age, weight, and general condition of the patient, the severity of the condition being treated, and the judgment of the prescribing-physician. Suitable therapeutic amounts will be known to those skilled in the art and/or are described in the pertinent reference texts and literature. As a comparison, current non-enterically coated doses of cysteamine are about 1.35 g/m$^2$ body surface area and are administered 4-5 times per day (Levtchenko et al., Pediatr Nephrol. 21:110-113, 2006). In one aspect, the dose of therapeutic is administered either one time per day or multiple times per day.

The small diffusible thiol composition may be administered less than four time per day, e.g., one, two or three times per day. In various embodiments, the total daily dose of small thiol composition or a pharmaceutically acceptable salt thereof for treatment of a disease or disorder described herein is between 200 to 1000, 500 to 2000 mg, 750 to 1750 mg, 1000 to 1500 mg, or may range between any two of the foregoing values. In various embodiments, the total daily dose of small diffusible thiol or a pharmaceutically acceptable salt thereof, is 200, 300, 400, 500, 600, 700, 800, 900, 1000, 1100, 1200, 1300, 1400, 1500, 1600, 1700, 1800, 1900 or 2000 mg per day. It is contemplated that any of the foregoing doses is administered twice daily. It is further contemplated that any of the foregoing doses is administered in two equal doses daily. Optionally, the daily dose is administered in three doses.

In some embodiments, an effective dosage of small thiol composition may be within the range of 0.01 mg to 1000 mg per kg (mg/kg) of body weight per day. In some embodiments, the small diffusible thiol composition or pharmaceutically acceptable salt thereof is administered at a daily dose ranging from about 1 to about 50 mg/kg/day, or from about 10 mg/kg to about 250 mg/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg, or from about 15 to about 25 mg/kg, or from about 15 to about 20 mg/kg or from about 10 to about 20 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values.

In some embodiments, the small thiol composition is administered at a total daily dose of from approximately 0.25 g/m$^2$ to 4.0 g/m$^2$ body surface area, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 g/m$^2$ or may range between any two of the foregoing values. In some embodiments, the small thiol composition may be administered at a total daily dose of about 0.5-2.0 g/m$^2$ body surface area, or 1-1.5 g/m$^2$ body surface area, or 1-1.95 g/m$^2$ body surface area, or 0.5-1 g/m$^2$ body surface area, or about 0.7-0.8 g/m$^2$ body surface area, or about 1.35 g/m$^2$ body surface area, or about 1.3 to about 1.95 grams/m2/day, or about 0.5 to about 1.5 grams/m2/day, or about 0.5 to about 1.0 grams/m2/day, preferably at a frequency of fewer than four times per day, e.g. three, two or one times per day. Salts or esters of the same active ingredient may vary in molecular weight depending on the type and weight of the salt or ester moiety. For administration of an enteric dosage form, e.g., a tablet or capsule or other oral dosage form comprising the enterically-coated small diffusible thiol composition, a total weight in the range of approximately 100 mg to 1000 mg is used. In various embodiments, the tablet or capsule comprises 25, 50, 75, 100, 125, 150, 175, 200, 225, 250, 275, 300, 400 or 500 mg active ingredient, and multiple tablets or capsules are administered to reach the desired dosage.

Combination Therapy

Therapeutic compositions described herein can also be administered in combination with adjunct therapy used in treatment of excitotoxicity and neurodegenerative diseases, such as antipsychotics, antidepressants, vesicular monoamine transporter (VMAT)-inhibitors such as tetrabenazine, dopamine inhibitors, laquinimod, CNS-immunomodulators, neuroprotective factors, BDNF and agents that upregulate BDNF, ampakines, positive modulators of AMPA-type glutamate receptors, activators of BDNF receptor TrkB and gene therapy.

Antidepressants include: SSRI antidepressants, such as fluoxetine, citalopram and paroxetine, tricyclic antidepressants, such as amitriptyline, other types of antidepressants, including mirtazapine, duloxetine and venlafaxine.

Antipsychotic medication includes risperidone, olanzapine, aripiprazole, tiapride and quetiapine, benzodiazepines, such as clonazepam and diazepam, and mood stabilizers, such as carbamazepine.

In some embodiments, the methods (or uses) described herein further comprise administering a further therapeutic agent selected from the group consisting of tetrabenazine, laquinimod, BDNF, ampakines, fluoxetine, citalopram, paroxetine, amitriptyline, mirtazapine, duloxetine, venlafaxine, risperidone, olanzapine, aripiprazole, tiapride, quetiapine, clonazepam diazepam and carbamazepine.

The small thiol composition and other drugs/therapies can be administered in combination either simultaneously in a single composition or in separate compositions. Alternatively, the administration is sequential. Simultaneous administration is achieved by administering a single composition or pharmacological protein formulation that includes both the small diffusible thiol composition and other therapeutic agent(s). Alternatively, the other therapeutic agent(s) are taken separately at about the same time as a pharmacological formulation (e.g., tablet, injection or drink) of the small thiol composition.

In various alternatives, administration of the small thiol composition can precede or follow administration of the other therapeutic agent(s) by intervals ranging from minutes to hours. For example, in various embodiments, it is further contemplated that the agents are administered in a separate formulation and administered concurrently, with concurrently referring to agents given within 30 minutes of each other.

In embodiments where the other therapeutic agent(s) and the small thiol composition are administered separately, one would generally ensure that the small thiol composition and the other therapeutic agent(s) are administered within an appropriate time of one another so that both the small thiol composition and the other therapeutic agent(s) can exert, synergistically or additively, a beneficial effect on the patient. For example, in various embodiments the small thiol composition is administered within about 0.5-6 hours (before or after) of the other therapeutic agent(s). In various embodiments, the small thiol composition is administered within about 1 hour (before or after) of the other therapeutic agent(s).

In another aspect, in a method to treat excitotoxicity disorders further comprising administering an agent that inhibits the $x_c^-$ transported, the agent that inhibits $x_c^-$ is administered prior to administration of the small thiol composition. Prior administration refers to administration of the agent that inhibits $x_c^-$ within the range of one week prior to treatment with small thiol composition, up to 30 minutes before administration of small thiol composition. It is further contemplated that the agent that inhibits $x_c^-$ is administered subsequent to administration of the small thiol composition. Subsequent administration is meant to describe administration from 30 minutes after small thiol composition treatment up to one week after small thiol administration.

In various embodiments, the effects of small thiol compositions in combination with an agent that inhibits $x_c^-$ on the symptoms of the excitotoxicity disease or disorder as described herein are measured as improvements in disease symptoms described above, or are measured as a slowing or decrease in the time of progression of a disease symptom, e.g., a slowed progression of total motor score can be considered an improvement in a disease symptom.

Kits

The disclosure also provides kits for carrying out the methods of the disclosure. In various embodiments, the kit contains, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a small thiol-containing composition and/or a composition comprising an inhibitor of $x_c^-$ transporter. The kits can also include dispensing devices, such as aerosol or injection dispensing devices, pen injectors, autoinjectors, needleless injectors, syringes, and/or needles. In various embodiments, the kit also provides an oral dosage form, e.g., a tablet or capsule or other oral formulation described herein, of the small thiol composition for use in the method. The kit also provides instructions for use.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

EXAMPLES

It was recently discovered that culture of neuronal cells in typical cell culture media such as DMEM and Neurobasal media, along with most other tissue culture media used for ex-vivo maintenance of neuronal cells, are inately excitotoxic (Maggioni, et al., Neuroreport 26, 320-324, 2015; Bardy et al., Proc Natl Acad Sci USA 112, E2725-2734, 2015). Survival in such media depends on a cocktail of antioxidant additives, identified empirically, which support the antioxidant defenses of the neurons themselves, but deprive cell-based models of physiological relevancy. Measuring the effect of sulfur amino acid starvation under these conditions is still possible, with the addition of an inhibitor of the cystine/glutamate antiporter ($x_c$), the primary source of cysteine to cells. Previous models were not able to test neuroprotective effects such as 1) glutamate receptor inhibition, 2) GABA receptor activation or inhibition, 3) voltage-gated calcium channel inhibition and 4) protein aggregation inhibition. It is contemplated that additional assays reveal that the captons herein inhibit protein aggregation and inhibit receptor-based mechanisms, including GABA potentiation, glutamate receptor inhibition or voltage-gated calcium channel blockade, by the products of reaction between the present thiols and ROS.

In order to identify molecules that could act therapeutically to effectively treat neurological disease, thiol compounds were screened for the ability to relieve sulfur amino acid starvation using mouse Q111 striatal neurons grown in DMEM with 5-10 mM glutamate. High glutamate prevents cystine import with no significant additional impact resulting from glutamate receptor activation (NMDA, AMPA), which occurs in DMEM on its own. Almost all captons rescue cells under such conditions by cleaving cystine in the extracellular space, permitting import of cysteine directly through alternative transporters (ASCT, aka SLC1A4 and SLC1A5), relieving sulfur amino acid starvation. PCT/US2016/040637 describes the striatal neuron assay and the initial selection criteria for captons. In addition to the above criteria, small thiols having similarities to GABA or taurine are then selected for us in the following assays to determine their neuroprotective effects.

Example 1—Measuring Oxidative Stress and its Prevention by Captons

While the assay with Q111 striatal neurons may measure the ability to rescue sulfur starvation, the previous assay does not measure rescue from excitotoxicity and the effects on neurotransmission and neuroprotection mediated by the small thiol compounds. The ability of test compounds to inhibit glutamate-induced excitotoxicity (neuroprotection) in St-HdhQ111/111 cells is determined by incubating the small thiol compounds with cells for 60 min at 33° C., 95% (v:v) air/5% (v:v) $CO_2$ in BrainPhys complete media (STEMCELL Technologies, Vancouver, British Columbia, Canada). Following this, excitotoxicity is induced by the addition of 0.5 mM L-glutamate for 24 hours. Cell viability is assessed by measuring ATP levels, e.g., using a luminescent-based CellTitre Glo assay (Promega). Compound neuroprotection (% cell survival) is expressed as a % of the effect recorded with 100 μM cysteamine (denoted as 100% cell survival).

It is expected that the tested compounds result in high levels of cell survival (e.g., at least 50% cell survival when expressed as a % of the effect for 100 μM cysteamine), including levels of cell survival highly similar to that provided by cysteamine in this particular system (e.g., at least 80% cell survival when expressed as a % of the effect for 100 μM cysteamine), suggesting that these compounds have similar neuroprotective effects compared to cysteamine.

Example 2—Protein Aggregation and its Prevention by Captons

The ability of test compounds to diminish aggregate formation in cells treated with hydrogen peroxide is determined. Briefly, MyCell SOD1 (G93A) neurons (CDI, Madison, Wisconsin) are cultured in 95% (v:v) air/5% (v:v) $CO_2$ in BrainPhys complete media (STEMCELL Technologies). Excitotoxic stress is induced by the addition of 0.5 mM L-glutamate for 2 hours, with and without capton or controls. Cells are harvested, pelleted and snap frozen. Frozen whole-cell pellets are homogenized in lysis buffer (25 mM Tris, pH 7.8, supplemented with protease inhibitors) at 4° C. by brief sonication and cleared by centrifugation at 18,000× g. Soluble SOD1-containing cleared supernatants are snap frozen for later analysis. Insoluble SOD1 (aggregated) is extracted from the lysed cell pellet. Pellets are re-suspended in 1 mL washing buffer (50 mM Tris HCl pH 7.4, 100 mM NaCl, 10% glycerol (v:v), 1% Triton X-100 (v:v), 0.5% NP-40 (v:v) with protease inhibitors by vortexing and centrifuged (10 min) at 18,000×g at 4° C. 4 times. The washed pellet is re-suspended in solubilization buffer (50 mM Tris HCl pH 7.4, 100 mM NaCl, 10% glycerol, 1% Triton X-100, 250 μM DTT, 1 mM EDTA, 2.5% SDS, with protease inhibitors, by vortexing, heated to 100° C. for 20 min, sonicated for 30 min, and heated again before centrifuging at 18,000×g for 10 min at 25° C. Total protein concentrations in the soluble and insoluble fractions are determined by Bradford assay. Samples are subjected to SDS-PAGE under reducing conditions and blotted to PVDF. Western blot analysis used to measure relative levels of soluble and insoluble SOD1 are probed with an anti-SOD1 antibody (Calbiochem, 574597) and an anti-tubulin antibody to normalize between lanes.

It is expected that treatment of cells with captons will significantly diminish the amount of insoluble SOD1 compared to soluble SOD1. Similar assays can be performed for TDP-43 aggregation or tau aggregation in appropriate cell-culture models.

Example 3—Reduction of Glutamate-Induced Excitotoxic Stress and Modulation of GABA Pathways by Oxidized Captons (o-Captons)

MyCell SOD1 (G93A) neurons (CDI, Madison, Wisconsin) are plated at a density of 20,000 cells/well in 384-well format in BrainPhys medium (STEMCELL Technologies, Vancouver, British Columbia, Canada) with antioxidants, 1 μg/mL laminin and neuronal growth factor supplements. Pre-coated poly-D-lysine (PDL) plates are coated with matrigel as a matrix according to standard protocol. Half the medium is changed every 3 days for 3 weeks. Cells are treated with either glutamate receptor antagonists, GABA receptor agonists, GABA receptor antagonists, or VGCC blockers in the presence or absence of either captons or o-captons for 30 min. Cells are then dosed with glutamate at 500 μM. At various timepoints, cells are assayed for viability using CellTiter-Glo 2.0 or calcium content using a total intracellular calcium kit or ROS using appropriate, commercially-available test kits. Cells are on other occasions assayed for mitochondrial stress or mitophagy also using appropriate test kits. To measure the ability and mechanism of capton-rescue from glutamate excitotoxicity, cells are pre-treated with a fixed concentration of glutamate (e.g., 5-10 mM) for an hour and then different concentrations of captons or o-captons are applied to the cells for an additional 24 hours. Harvested cells are then tested as described above.

It is contemplated that captons and o-captons improve cell-viability, reduce intracellular calcium concentrations, relieve mitochondrial stress and enhance mitophagy in cells under glutamate stress. GABAergic agents, transaminase inhibitors and reuptake inhibitors are hypothesized to be of no additional benefit over o-captons with similar activities.

It is hypothesized that calcium channel blockers will be of no additional advantage over gabapentinoid-like o-captons.

Example 4—Measurement of Mitigation of Seizure Activity and Oxidative Stress by Captons in a Kainic Acid-Induced Model of Temporal Lobe Epilepsy Male, Sprague-Dawley rats, (aged 9-11 weeks) are used in the study. Controls, test articles and kainic acid (KA, 15 mg/kg body weight; 10 mg/ml in normal saline) are administered subcutaneously (sc) to all groups. KA (15 mg/kg body weight) triggers hyperexcitation and excitotoxic damage within 2 hours. Group 1, pretreated with saline, no KA; Group 2, pretreated with saline followed an hour later with KA; Group 3, pretreated with capton test article followed an hour later with KA; Group 4, pretreated with topiramate (positive control) then KA an hour later; Group 5, no pretreatment, saline and KA co-administered; Group 6, no pretreatment, capton and KA co-administered. Following KA administration, animals are monitored for 4 hours and the time-to-onset of seizures noted. Diazepam (10 mg/kg body weight) is administered intraperitoneally 90 min after the first seizure. Behavioral change is observed using an open field test (OFT) to assess locomotor activity in 15 minutes in an unobstructed space. Activity is recorded using a video-tracking system. Subjects are euthanized by deep anesthesia with ketamine/xylazine, followed by brief perfusion with cold saline and decapitation. Cortices are removed, weighed and washed with cold saline. One half of each cortex is homogenized in ice-cold PBS and clarified by centrifugation. Homogenate is assayed for lipid peroxidation and anti-oxidant status. The intact cortical hemisphere is immediately fixed, embedded, sectioned and stained for automated neuron counting and immunohistochemical assessment of damage.

Example 5—In Vitro Oxidation Assay

In order, 4 µL of water or an appropriate aqueous metal solution (1 µM Cu(I)Cl or 5 µM Fe(II)SO$_4$) was combined with 92 µL hydrogen peroxide (200 µM, freshly diluted from 30%) in bicarbonate buffer (1.25%, pH 7.8-8.2) and 4 µL of the capton (thiol) being assayed (0-100 µM) or thiol standard. The reactions were allowed to proceed from 1 minute to 24 hours, and were then quenched with 4 µL of 10 mM TCEP and shaken for 5 minutes to destroy peroxide and reduce disulfides. A 10 µL aliquot of the TCEP-quenched reaction was removed, and it was added to 90 µL ABD-F solution (1 mM in 20 mM HEPES pH 7). Fluorescence was measured at 513 nm after excitation at 389 nm after 30 minutes.

Figure 3:
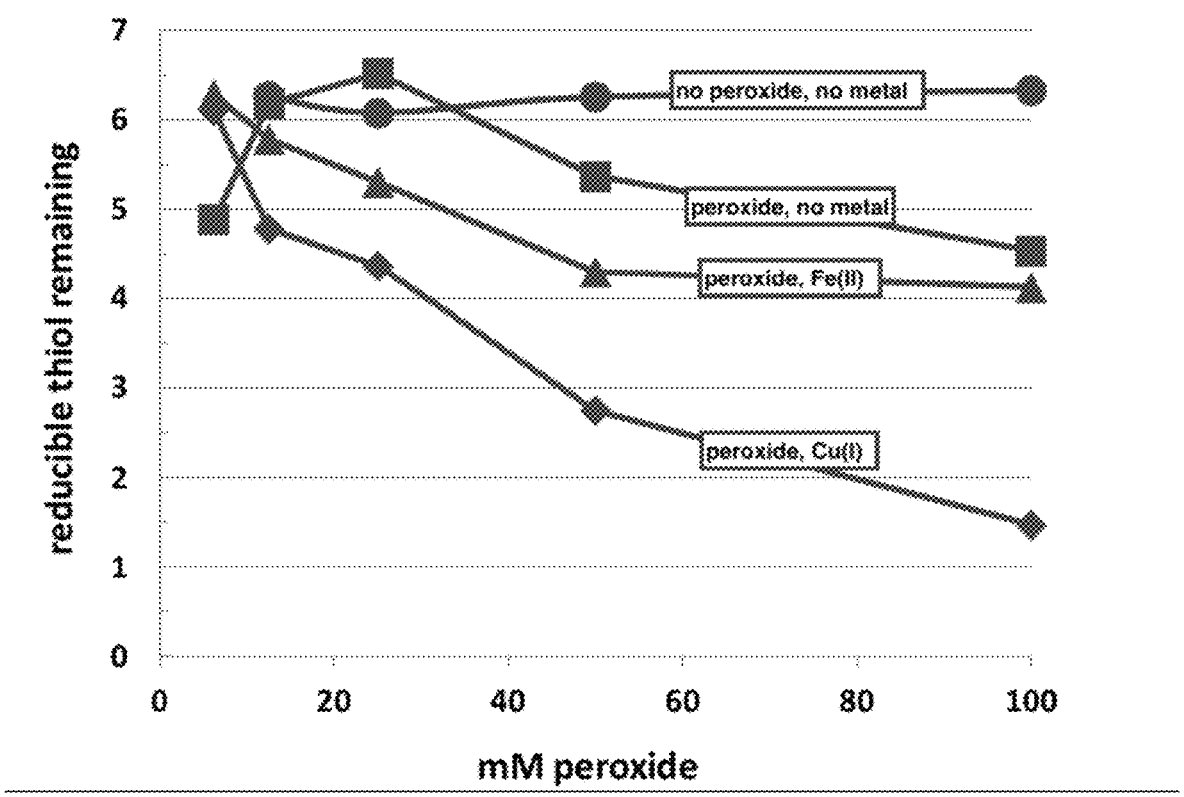
FIG. 3 shows the oxidation of 2-aminocyclohexanethiol by peroxide alone, or in the presence of Fe(II) or Cu(I).
Figure 4:
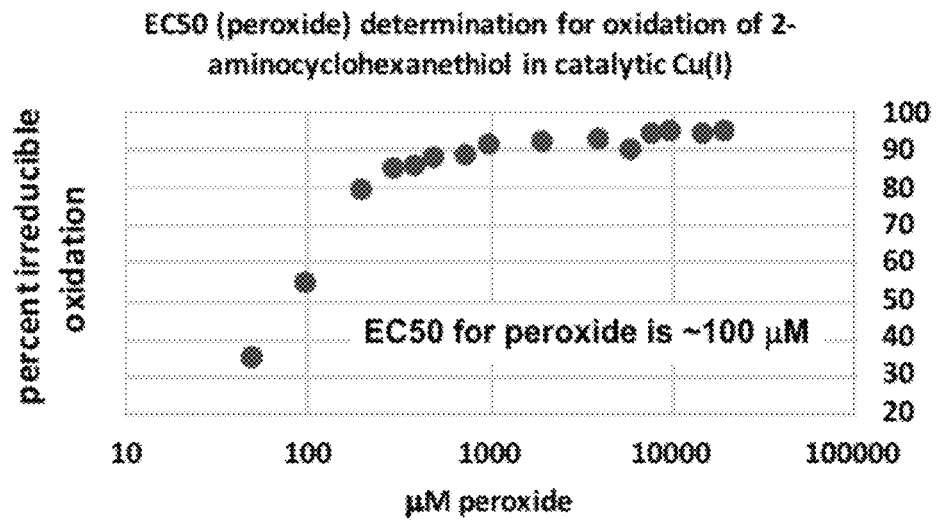
FIG. 4 shows the $EC_{50}$ determination for oxidation of 2-aminocyclohexanethiol by peroxide in the presence of catalytic Cu(I).
Figure 5:
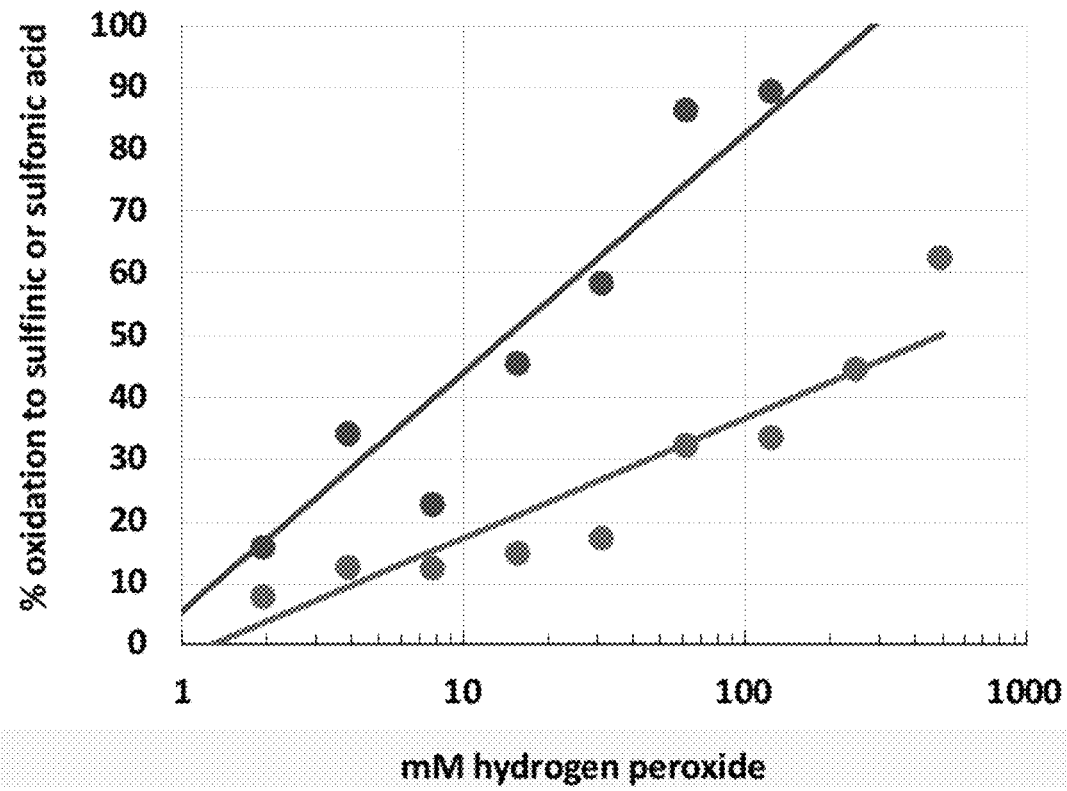
FIG. 5 shows the in vitro oxidation of 2-aminocyclohexanethiol (capton-004) and piperidine-3-thiol (capton-003) by hydrogen peroxide in the absence of metals.
Figure 6:
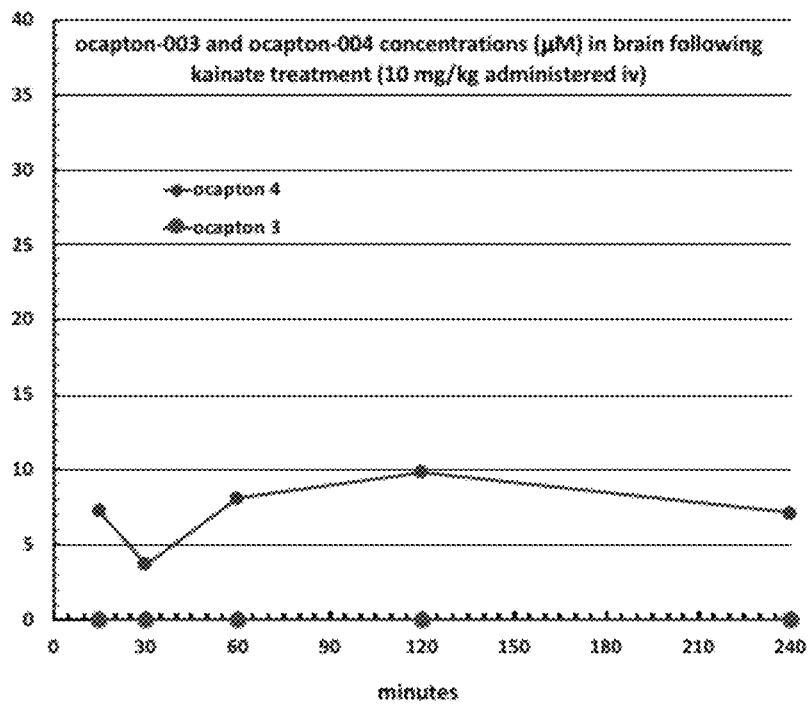
FIG. 6 shows the concentrations of ocapton-003 and ocapton-004 in a rat brain model following treatment with kainate.
Figure 7:
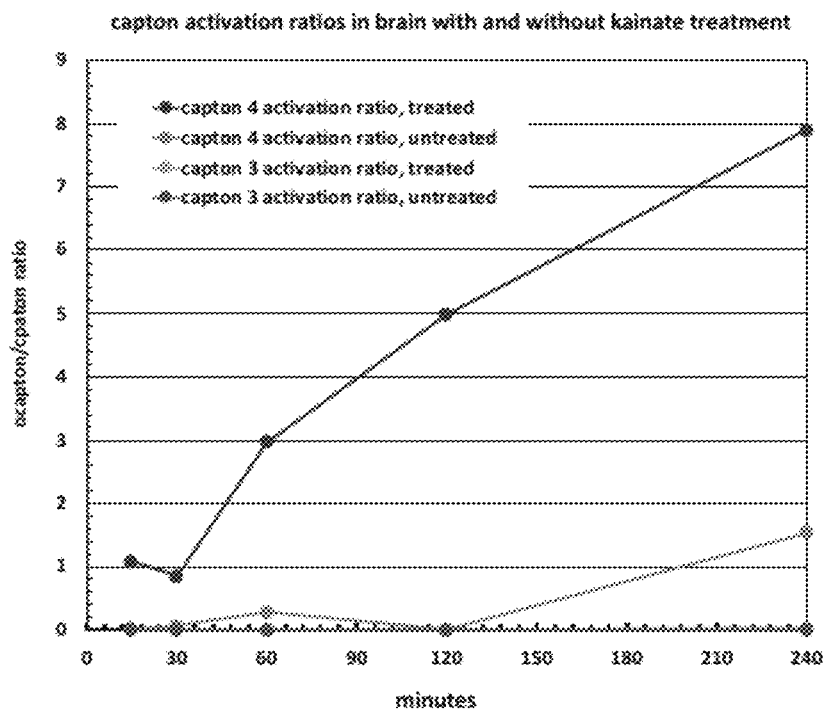
FIG. 7 shows the ratio of ocapton to capton for captons 003 and 004 in a rat brain model with and without treatment with kainate.
Figure 8:
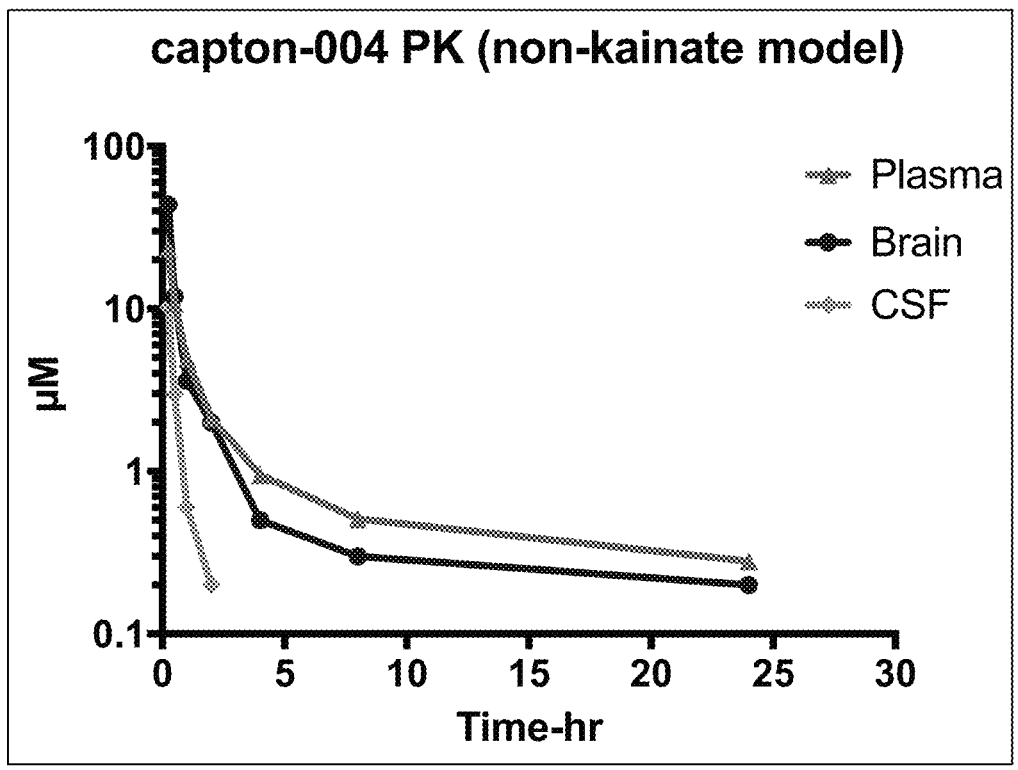
FIG. 8 shows pharmacokinetic profiles for capton-004 in a non kainate-treated rat model.
Figure 9:
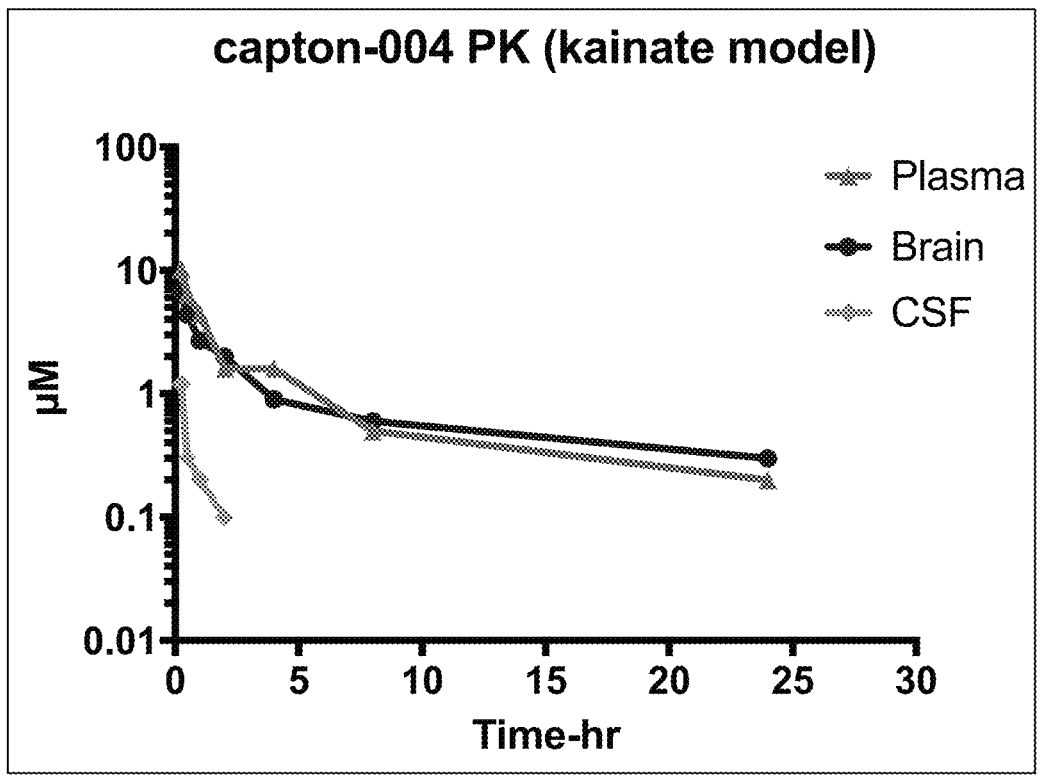
FIG. 9 shows pharmacokinetic profiles for capton-004 in a kainate-treated rat model.

Results are presented in FIGS. 3, 4, and 5.

Example 6—Pharmacokinetics and ADME of Captons in Normal and Kainic Acid-Treated CD Rats The objective of the study was to investigate the pharmacokinetics and ADME of two capton molecules, capton-003 and capton-004, after a single intravenous injection into healthy CD rats, as well as CD rats treated with the CNS excitotoxin, kainic acid. In particular, half-life, clearance, and area under the pharmacokinetic curve were determined on the basis of capton tissue levels and those of an oxidized metabolite (ocapton).

Experiments were performed as specified on the license authorized by the National Animal Experiment Board of Finland (Eläinkoelautakunta, ELLA) and according to the National Institutes of Health (Bethesda, MD, USA) guidelines for the care and use of laboratory animals. In total, 111 CD rats (250-275 grams) were used for the study. Animals were housed at a standard temperature (22±1° C.), in a light-controlled environment (dark from 8 pm-7 am) with ad libitum access to food and water.

Animals were grouped as follows, with a summary presented in Table B, below:

Group 1: control, 6 rats injected intravenously (i.v.) under light isoflurane anesthesia with vehicle for capton derivatives (2 mL/kg) and sampled 1 hour after vehicle injection (N=6).

Group 2: 21 rats, 10 mg/kg capton-003, sampled 15 min (N=3); 30 min (N=3); 1 hour (N=3); 2 hours (N=3); 4 hours (N=3); 8 hours (N=3) and 24 hours (N=3) after injection.

Group 3: 21 rats, capton-004.

TABLE B

| Group ID | Treatment | Group size (N) | Route | Dose (mg/kg) | Dosing Vol. (mL/kg) |
|---|---|---|---|---|---|
| 1 | vehicle | 6 | i.v. | 10 | 2 |
| 2 | capton-003 | 21 | i.v. | 10 | 2 |
| 3 | capton-004 | 21 | i.v. | 10 | 2 |

Powdered capton materials were weighed and dissolved in enough phosphate-buffered saline to afford the desired concentrations for injection. Rats were assigned to treatment groups and tail-marked accordingly with a Sharpie. Body weight, treatment group and treatment times were recorded. A single intravenous injection of the vehicle or test article (capton-003 or capton-004) were given to the rats at a dose of 10 mg/kg, with a dosing volume of 2 mL/kg.

Rats were deeply anesthetized with pentobarbital and blood samples collected by cardiac puncture. Blood (500 µL) was initially collected into K2-EDTA microtubes. Samples were centrifuged (2500×g for 10 min at 4° C.). Plasma supernatant fractions were isolated (~200 µL), frozen on dry ice, and stored at −80° C. until shipment on dry ice for subsequent detection of capton and ocapton. Prior to analysis for captons, plasma samples were thawed on ice, followed by immediate TCEP (tris(2-carboxyethyl)phosphine) addition (ice-cold) to a final concentration of 5 mM. Treated samples were then deproteinized using acetonitrile with formic acid (also ice-cold) and supernatants kept cold and at low pH prior to LC-MS analysis. After blood collection, CSF was collected from the cisterna magna. CSF clarity was recorded and characterized as clear, slightly-tinged, tinged, pink, or bloody. If scoring indicated tinged, pink or bloody, samples were clarified by centrifugation. Sample tubes were tared and CSF added. The CSF sample weight was then determined and recorded. CSF samples were frozen on dry ice and stored at −80° C. until shipment on dry ice for subsequent detection of capton and ocapton. Prior to analysis, CSF samples were thawed on ice and treated as previously described for plasma. After CSF collection, the rats were perfused by cardiac puncture with saline and decapitated. The top of the skull was removed, along with pial vessels, and the entire brain of each animal extracted. Brain tissue was frozen on dry ice and stored at −80° C. Prior to capton analysis, brain tissues were thawed on ice, followed by immediate addition of extraction buffer (20 mM ammonium formate, 5 mM TCEP, pH 3.5; pH adjusted with formic acid) and tissue extraction achieved by sonication. Disulfide bonds in tissue homogenates were reduced by incubation at 37° C. for 30 min. After the reduction step, PCA (perchloric acid) was added to the homogenate to a final concentration of 100 mM and tissue homogenates centrifuged (30 min, 4° C., 13,000 rpm). Supernatants were stored as tissue extracts at −80° C. until analysis.

Sample analysis was performed using liquid chromatography (LC) and tandem mass spectrometry (MS) analysis. Prior to the analysis of study compounds in plasma, CSF, and brain tissue samples, method development was performed to ensure that robust and reliable quantification was possible. All compounds were first tuned individually by direct infusion (MS-only) in ESi+ mode on an API-4000 or API-5000 triple-quadrupole mass-spectrometer equipped with a Turbo Ion Spray interface (Sciex). Sample resolution by HPLC (HILIC amide or $C_{18}$ reversed-phase) was performed prior to MS analysis. For HILIC, an eluent of 70% acetonitrile in 2 mM ammonium formate, 3.6 mM formic acid was employed; for $C_{18}$, a gradient of acetonitrile in ultra-purified water, 0.1% formic acid was tested. Chromatographic properties, such as retention time (stability), peak shape, response, separation from isomers, and stability (initially in solvent, later in matrix), were evaluated using known standards. Compound standards were spiked into the biological matrices of interest and bioanalytical parameters captured (e.g., matrix interference, matrix background). Lowest-limit-of-quantitation (LLOQ) for each analyte was determined after achieving 1) adequate signal-to-noise ratios, 2) adequate discrimination from background peaks exceeding noise (if present), 3) calculated accuracy. Quality during the analysis of the unknown study samples was ensured through the use of known standards at three concentration levels, with blanks. For stability determination during analysis, processed samples from the different matrices were kept in the instrument's autosampler under acidic conditions at 4° C. Acidic conditions during LC-MS analysis (with 0.1% formic acid or formic acid in combination with ammonium formate) were maintained for stability.

Example 7—Effects of Kainic Acid on Capton Pharmacokinetics and ADME in CD Rats

The objective of the study was to investigate the pharmacokinetics of capton-003 and capton-004 after intravenous injection into CD rats pre-treated with kainic acid, an excitotoxin known to increase levels of brain reactive-oxygen species (ROS). In particular, half-life, clearance, and area under the pharmacokinetic curve were determined on the basis of the levels of capton and an oxidized metabolite, ocapton (capton sulfonate), in the brain, CSF and blood plasma 1.25-25 h after administration of the test articles, except that rats were additionally injected with kainic acid (15 mg/kg, intraperitoneal) an hour after each capton.

All animal experiments were performed as specified in the license authorized by the national Animal Experiment Board of Finland (Eläinkoelautakunta, ELLA) and according to the National Institutes of Health (Bethesda, MD, USA) guidelines for the care and use of laboratory animals. In total, 210 CD rats (250-275 g) were used for the study. Animals were housed at a standard temperature (22±1° C.) and in a light-controlled environment (on from 7 am to 8 pm) with ad libitum access to food and water.

Animals were grouped as follows, with a summary presented in Table C, below:

Group 1 (control): 35 rats were injected intravenously (i.v.) under light isoflurane anesthesia with capton vehicle (2 mL/kg) and then, an hour later, with 15 mg/kg kainic acid intraperitoneally (i.p.). Rats were sampled 15 min after kainate injection (N=5); 30 min (N=5); 1 h (N=5); 2 h (N=5); 4 h (N=5); 8 h (N=5) and 24 h (N=5).

Group 2 (capton-003): 35 rats were injected i.v. under light isoflurane anesthesia with 10 mg/kg capton-003 and then, an hour later, with 15 mg/kg kainic acid intraperitoneally (i.p.). Rats were sampled 15 min after kainate injection (N=5); 30 min (N=5); 1 h (N=5); 2 h (N=5); 4 h (N=5); 8 h (N=5) and 24 h (N=5).

Group 3 (capton-004): 35 rats were injected i.v. under light isoflurane anesthesia with 10 mg/kg capton-004 and then, an hour later, with 15 mg/kg kainic acid intraperitoneally (i.p.). Rats were sampled 15 min after kainate injection (N=5); 30 min (N=5); 1 h (N=5); 2 h (N=5); 4 h (N=5); 8 h (N=5) and 24 h (N=5).

TABLE C

| Group ID | Treatment | Group size (n) | Route of Admin. | Dose (mg/kg) | Dosing Vol. (mL/kg) |
|---|---|---|---|---|---|
| 1 | capton vehicle | 35 | i.v. | 10 | 2 |
| 1 | kainate | 35 | i.p. | 15 | 2 |
| 2 | capton-003 | 35 | i.v. | 10 | 2 |
| 2 | kainate | 35 | i.p. | 15 | 2 |
| 3 | capton-004 | 35 | i.v. | 10 | 2 |
| 3 | kainate | 35 | i.p. | 15 | 2 |

Rats were given a single i.v. injection of one of the two tested capton derivatives at a concentration of 10 mg/kg (Groups 2 and 3) or capton vehicle (Group 1). An hour later, all rats received a single intraperitoneal injection of 15 mg/kg kainic acid. Rats were then sacrificed at 15 min, 30 min, 1 h, 2 h, 4 h, 8 h or 24 h post-kainic acid. Samples of the cerebrospinal fluid (CSF), blood plasma and brain were then obtained for subsequent bioanalytical detection of capton and ocapton.

The rats were assigned to the treatment groups and tail-marked accordingly with a permanent marker. Records were made about body weight, treatment groups and treatment times.

A single intravenous administration of the vehicle or each of the studied capton derivatives (capton-002, -003, -004, and -007) at a dose of 10 mg/kg was given to the rats. Kainate was dissolved in saline and administered at a dose of 15 mg/kg i.p. in 1 h after capton/vehicle injection. Dosing volumes in both cases was 2 mL/kg.

Results from the studies of Examples 6 and 7 are presented in FIGS. 6, 7, 8, 9, and 10.

Example 8—Effects of Captons on Seizure Scoring in CD Rats

During the last 2 min prior to the dissection in Examples 6 and 7, rats were observed for the presence of convulsant activity and its manifestations were scored according to the following scale: 0, normal; 1, immmobilization, occasional "wet-dog shakes"; 2, head nodding, unilateral forelimb clonus, frequent "wet dog shakes"; 3, rearing, salivation, bilateral forelimb clonus; 4, generalized limbic seizures with falling, running and salivation; 5, continuous generalized seizures with tonic limbic extension, death.

Numerous modifications and variations in the invention as set forth in the above illustrative examples are expected to occur to those skilled in the art. Consequently, only such limitations as appear in the appended claims should be placed on the invention.

REFERENCES

1. Jurkowska, H., Stipanuk, M. H., Hirschberger, L. L., and Roman, H. B. (2015) Propargylglycine inhibits hypotaurine/taurine synthesis and elevates cystathionine and homocysteine concentrations in primary mouse hepatocytes. Amino Acids 47, 1215-1223
2. Mishanina, T. V., Libiad, M., and Banerjee, R. (2015) Biogenesis of reactive sulfur species for signaling by hydrogen sulfide oxidation pathways. Nat Chem Biol 11, 457-464
3. Shen, W., McGath, M. K., Evande, R., and Berkowitz, D. B. (2005) A continuous spectrophotometric assay for human cystathionine beta-synthase. Anal Biochem 342, 103-110
4. Thorson, M. K., Majtan, T., Kraus, J. P., and Barrios, A. M. (2013) Identification of cystathionine beta-synthase inhibitors using a hydrogen sulfide selective probe. Angew Chem Int Ed Engl 52, 4641-4644
5. Chen, X., Jhee, K. H., and Kruger, W. D. (2004) Production of the neuromodulator H2S by cystathionine beta-synthase via the condensation of cysteine and homocysteine. J Biol Chem 279, 52082-52086
6. Asimakopoulou, A., Panopoulos, P., Chasapis, C. T., Coletta, C., Zhou, Z., Cirino, G., Giannis, A., Szabo, C., Spyroulias, G. A., and Papapetropoulos, A. (2013) Selectivity of commonly used pharmacological inhibitors for cystathionine beta synthase (CBS) and cystathionine gamma lyase (CSE). Br J Pharmacol 169, 922-932
7. Froestl, W. (2010) Chemistry and pharmacology of GABAB receptor ligands. Adv Pharmacol 58, 19-62
8. Caddick, S. J., Stanford, I. M., and Chad, J. E. (1995) 2-Hydroxy-saclofen causes a phaclofen-reversible reduction in population spike amplitude in the rat hippocampal slice. Eur J Pharmacol 274, 41-46
9. Yudkoff, M., Foreman, J. W., and Segal, S. (1981) Effects of cysteamine therapy in nephropathic cystinosis. The New England journal of medicine 304, 141-145
10. Issels, R. D., Nagele, A., Eckert, K. G., and Wilmanns, W. (1988) Promotion of cystine uptake and its utilization for glutathione biosynthesis induced by cysteamine and N-acetylcysteine. Biochem Pharmacol 37, 881-888
11. Wilmer, M. J., Kluijtmans, L. A., van der Velden, T. J., Willems, P. H., Scheffer, P. G., Masereeuw, R., Monnens, L. A., van den Heuvel, L. P., and Levtchenko, E. N. (2011) Cysteamine restores glutathione redox status in cultured cystinotic proximal tubular epithelial cells. Biochim Biophys Acta 1812, 643-651
12. Lewerenz, J., and Maher, P. (2009) Basal levels of eIF2alpha phosphorylation determine cellular antioxidant status by regulating ATF4 and xCT expression. J Biol Chem 284, 1106-1115
13. Massie, A., Boillee, S., Hewett, S., Knackstedt, L., and Lewerenz, J. (2015) Main path and byways: non-vesicular glutamate release by system xc(-) as an important modifier of glutamatergic neurotransmission. J Neurochem 135, 1062-1079
14. Patel, S. A., Warren, B. A., Rhoderick, J. F., and Bridges, R. J. (2004) Differentiation of substrate and non-substrate inhibitors of transport system xc(-): an obligate exchanger of L-glutamate and L-cystine. Neuropharmacology 46, 273-284
15. Lewerenz, J., Klein, M., and Methner, A. (2006) Cooperative action of glutamate transporters and cystine/glutamate antiporter system Xc- protects from oxidative glutamate toxicity. J Neurochem 98, 916-925
16. Bridges, R. J., Natale, N. R., and Patel, S. A. (2012) System xc(-) cystine/glutamate antiporter: an update on molecular pharmacology and roles within the CNS. Br J Pharmacol 165, 20-34
17. Chung, M. C., Malatesta, P., Bosquesi, P. L., Yamasaki, P. R., Santos, J. L., and Vizioli, E. O. (2012) Advances in drug design based on the amino Acid approach: taurine analogues for the treatment of CNS diseases. Pharmaceuticals (Basel) 5, 1128-1146
18. Albano, R., Raddatz, N. J., Hjelmhaug, J., Baker, D. A., and Lobner, D. (2015) Regulation of System xc(-) by Pharmacological Manipulation of Cellular Thiols. Oxid Med Cell Longev 2015, 269371
19. Krall, J., Balle, T., Krogsgaard-Larsen, N., Sorensen, T. E., Krogsgaard-Larsen, P., Kristiansen, U., and Frolund, B. (2015) GABAA receptor partial agonists and antagonists: structure, binding mode, and pharmacology. Adv Pharmacol 72, 201-227
20. Frederick, N. M., Bertho, J., Patel, K. K., Petr, G. T., Bakradze, E., Smith, S. B., and Rosenberg, P. A. (2014) Dysregulation of system xc(-) expression induced by mutant huntingtin in a striatal neuronal cell line and in $R^{6/2}$ mice. Neurochem Int 76, 59-69
21. Salat, K., and Kulig, K. (2011) GABA transporters as targets for new drugs. Future medicinal chemistry 3, 211-222
22. Albrecht, P., Lewerenz, J., Dittmer, S., Noack, R., Maher, P., and Methner, A. (2010) Mechanisms of oxidative glutamate toxicity: the glutamate/cystine antiporter system xc- as a neuroprotective drug target. CNS & neurological disorders drug targets 9, 373-382
23. Kigerl, K. A., Ankeny, D. P., Garg, S. K., Wei, P., Guan, Z., Lai, W., McTigue, D. M., Banerjee, R., and Popovich, P. G. (2012) System x(c)(-) regulates microglia and macrophage glutamate excitotoxicity in vivo. Exp Neurol 233, 333-341
24. Bridges, R., Lutgen, V., Lobner, D., and Baker, D. A. (2012) Thinking outside the cleft to understand synaptic activity: contribution of the cystine-glutamate antiporter (System xc-) to normal and pathological glutamatergic signaling. Pharmacol Rev 64, 780-802
25. Maher, P., Lewerenz, J., Lozano, C., and Torres, J. L. (2008) A novel approach to enhancing cellular glutathione levels. J Neurochem 107, 690-700
26. Yin, J., Ren, W., Yang, G., Duan, J., Huang, X., Fang, R., Li, C., Li, T., Yin, Y., Hou, Y., Kim, S. W., and Wu, G. (2016) L-Cysteine metabolism and its nutritional implications. Mol Nutr Food Res 60, 134-146
27. Bak, D. W., and Weerapana, E. (2015) Cysteine-mediated redox signalling in the mitochondria. Mol Biosyst 11, 678-697
28. Poole, L. B. (2015) The basics of thiols and cysteines in redox biology and chemistry. Free Radic Biol Med 80, 148-157
29. Cacciatore, I., Cornacchia, C., Pinnen, F., Mollica, A., and Di Stefano, A. (2010) Prodrug approach for increasing cellular glutathione levels. Molecules 15, 1242-1264
30. Francelle, L., Galvan, L., and Brouillet, E. (2014) Possible involvement of self-defense mechanisms in the preferential vulnerability of the striatum in Huntington's disease. Front Cell Neurosci 8, 295

31. McBean, G. J., Aslan, M., Griffiths, H. R., and Torrao, R. C. (2015) Thiol redox homeostasis in neurodegenerative disease. Redox Biol 5, 186-194
32. Patel, M. (2016) Targeting Oxidative Stress in Central Nervous System Disorders. Trends Pharmacol Sci 37, 768-778
33. Shih, A. Y., Erb, H., Sun, X., Toda, S., Kalivas, P. W., and Murphy, T. H. (2006) Cystine/glutamate exchange modulates glutathione supply for neuroprotection from oxidative stress and cell proliferation. J Neurosci 26, 10514-10523
34. Cramer, S. L., Saha, A., Liu, J., Tadi, S., Tiziani, S., Yan, W., Triplett, K., Lamb, C., Alters, S. E., Rowlinson, S., Zhang, Y. J., Keating, M. J., Huang, P., DiGiovanni, J., Georgiou, G., and Stone, E. (2017) Systemic depletion of L-cyst(e)ine with cyst(e)inase increases reactive oxygen species and suppresses tumor growth. Nat Med 23, 120-127
35. Zheng, W., and Monnot, A. D. (2012) Regulation of brain iron and copper homeostasis by brain barrier systems: implication in neurodegenerative diseases. Pharmacol Ther 133, 177-188
36. Tokuda, E., and Furukawa, Y. (2016) Copper Homeostasis as a Therapeutic Target in Amyotrophic Lateral Sclerosis with SOD1 Mutations. Int J Mol Sci 17
37. Ben-Shachar, D., and Youdim, M. B. (1991) Intranigral iron injection induces behavioral and biochemical "parkinsonism" in rats. J Neurochem 57, 2133-2135
38. Lin, A. M. (2001) Coexistence of zinc and iron augmented oxidative injuries in the nigrostriatal dopaminergic system of SD rats. Free Radic Biol Med 30, 225-231
39. Peters, D. G., Connor, J. R., and Meadowcroft, M. D. (2015) The relationship between iron dyshomeostasis and amyloidogenesis in Alzheimer's disease: Two sides of the same coin. Neurobiol Dis 81, 49-65
40. Biaglow, J. E., Issels, R. W., Gerweck, L. E., Varnes, M. E., Jacobson, B., Mitchell, J. B., and Russo, A. (1984) Factors influencing the oxidation of cysteamine and other thiols: implications for hyperthermic sensitization and radiation protection. Radiat Res 100, 298-312
41. Golko-Perez, S., Amit, T., Bar-Am, O., Youdim, M. B., and Weinreb, O. (2017) A Novel Iron Chelator-Radical Scavenger Ameliorates Motor Dysfunction and Improves Life Span and Mitochondrial Biogenesis in SOD1G93A ALS Mice. Neurotox Res 31, 230-244
42. Lee, S., and Kim, H. J. (2015) Prion-like Mechanism in Amyotrophic Lateral Sclerosis: are Protein Aggregates the Key? Exp Neurobiol 24, 1-7
43. Alvarez-Zaldiernas, C., Lu, J., Zheng, Y., Yang, H., Blasi, J., Solsona, C., and Holmgren, A. (2016) Cellular Redox Systems Impact the Aggregation of Cu,Zn Superoxide Dismutase Linked to Familial Amyotrophic Lateral Sclerosis. J Biol Chem 291, 17197-17208
44. Cohen, T. J., Hwang, A. W., Unger, T., Trojanowski, J. Q., and Lee, V. M. (2012) Redox signalling directly regulates TDP-43 via cysteine oxidation and disulphide cross-linking. EMBO J 31, 1241-1252
45. Chen, X., Shang, H., Qiu, X., Fujiwara, N., Cui, L., Li, X. M., Gao, T. M., and Kong, J. (2012) Oxidative modification of cysteine 111 promotes disulfide bond-independent aggregation of SOD1. Neurochem Res 37, 835-845
46. Bosco, D. A., Morfini, G., Karabacak, N. M., Song, Y., Gros-Louis, F., Pasinelli, P., Goolsby, H., Fontaine, B. A., Lemay, N., McKenna-Yasek, D., Frosch, M. P., Agar, J. N., Julien, J. P., Brady, S. T., and Brown, R. H., Jr. (2010) Wild-type and mutant SOD1 share an aberrant conformation and a common pathogenic pathway in ALS. Nat Neurosci 13, 1396-1403
47. Yuyu Songa, M. N., Weiming Nic, Navneet K. Tyagic, Wayne A. Fentonc, Francesc López-Gireldeze, John D. Overtone, Arthur L. Horwich and Scott T. Brady. (2013) Molecular chaperone Hsp110 rescues a vesicle transport defect produced by an ALS-associated mutant SOD1 protein in squid axoplasm. Proc Natl Acad Sci USA 110, 5428-5433
48. Hackett, M. J., Smith, S. E., Caine, S., Nichol, H., George, G. N., Pickering, I. J., and Paterson, P. G. (2015) Novel bio-spectroscopic imaging reveals disturbed protein homeostasis and thiol redox with protein aggregation prior to hippocampal CA1 pyramidal neuron death induced by global brain ischemia in the rat. Free Radic Biol Med 89, 806-818
49. Martineau, E., de Guzman, J. M., Rodionova, L., Kong, X., Mayer, P. M., and Aman, A. M. (2010) Investigation of the noncovalent interactions between anti-amyloid agents and amyloid beta peptides by ESI-MS. J Am Soc Mass Spectrom 21, 1506-1514
50. McKee, A. C., Gavett, B. E., Stern, R. A., Nowinski, C. J., Cantu, R. C., Kowall, N. W., Perl, D. P., Hedley-Whyte, E. T., Price, B., Sullivan, C., Morin, P., Lee, H. S., Kubilus, C. A., Daneshvar, D. H., Wulff, M., and Budson, A. E. (2010) TDP-43 proteinopathy and motor neuron disease in chronic traumatic encephalopathy. J Neuropathol Exp Neurol 69, 918-929
51. Smethurst, P., Newcombe, J., Troakes, C., Simone, R., Chen, Y. R., Patani, R., and Sidle, K. (2016) In vitro prion-like behaviour of TDP-43 in ALS. Neurobiol Dis 96, 236-247
52. Omalu, B. (2014) Chronic traumatic encephalopathy. Prog Neurol Surg 28, 38-49
53. Jucker, M., and Walker, L. C. (2013) Self-propagation of pathogenic protein aggregates in neurodegenerative diseases. Nature 501, 45-51
54. Nonaka, T., and Hasegawa, M. (2017) TDP-43 Prions. Cold Spring Harb Perspect Med
55. Giacomelli, C., Daniele, S., and Martini, C. (2017) Potential biomarkers and novel pharmacological targets in protein aggregation-related neurodegenerative diseases. Biochem Pharmacol 131, 1-15
56. Kim, D., Lim, S., Haque, M. M., Ryoo, N., Hong, H. S., Rhim, H., Lee, D. E., Chang, Y. T., Lee, J. S., Cheong, E., Kim, D. J., and Kim, Y. K. (2015) Identification of disulfide cross-linked tau dimer responsible for tau propagation. Sci Rep 5, 15231
57. Xie, W., Wan, O. W., and Chung, K. K. (2010) New insights into the role of mitochondrial dysfunction and protein aggregation in Parkinson's disease. *Biochim Biophys* Acta 1802, 935-941
58. Karpuj, M. V., Garren, H., Slunt, H., Price, D. L., Gusella, J., Becher, M. W., and Steinman, L. (1999) Transglutaminase aggregates huntingtin into nonamyloidogenic polymers, and its enzymatic activity increases in Huntington's disease brain nuclei. *Proc Natl Acad Sci USA* 96, 7388-7393
59. Choi, J., Rees, H. D., Weintraub, S. T., Levey, A. I., Chin, L. S., and Li, L. (2005) Oxidative modifications and aggregation of Cu,Zn-superoxide dismutase associated with Alzheimer and Parkinson diseases. *J Biol Chem* 280, 11648-11655
60. Novoselov, S. S., Mustill, W. J., Gray, A. L., Dick, J. R., Kanuga, N., Kalmar, B., Greensmith, L., and Cheetham, M. E. (2013) Molecular chaperone mediated late-stage neuroprotection in the SOD1(G93A) mouse model of amyotrophic lateral sclerosis. *PLoS One* 8, e73944
61. Nagano, S., Takahashi, Y., Yamamoto, K., Masutani, H., Fujiwara, N., Urushitani, M., and Araki, T. (2015) A cysteine residue affects the conformational state and neuronal toxicity of mutant SOD1 in mice: relevance to the pathogenesis of ALS. *Hum Mol Genet* 24, 3427-3439
62. Parone, P. A., Da Cruz, S., Han, J. S., McAlonis-Downes, M., Vetto, A. P., Lee, S. K., Tseng, E., and Cleveland, D. W. (2013) Enhancing mitochondrial calcium buffering capacity reduces aggregation of misfolded SOD1 and motor neuron cell death without extending survival in mouse models of inherited amyotrophic lateral sclerosis. *J Neurosci* 33, 4657-4671
63. Chang, K. L., Pee, H. N., Yang, S., and Ho, P. C. (2015) Influence of drug transporters and stereoselectivity on the brain penetration of pioglitazone as a potential medicine against Alzheimer's disease. *Sci Rep* 5, 9000
64. Zarei, S., Carr, K., Reiley, L., Diaz, K., Guerra, O., Altamirano, P. F., Pagani, W., Lodin, D., Orozco, G., and Chinea, A. (2015) A comprehensive review of amyotrophic lateral sclerosis. *Surg Neurol Int* 6, 171
65. Krumova, K., and Cosa, G. (2016) Chapter 1. Overview of Reactive Oxygen Species. 1, 1-21
66. Freinbichler, W., Colivicchi, M. A., Stefanini, C., Bianchi, L., Ballini, C., Misini, B., Weinberger, P., Linert, W., Vareslija, D., Tipton, K. F., and Della Corte, L. (2011) Highly reactive oxygen species: detection, formation, and possible functions. *Cell Mol Life Sci* 68, 2067-2079
67. Kim, H. J., Ha, S., Lee, H. Y., and Lee, K. J. (2015) ROSics: chemistry and proteomics of cysteine modifications in redox biology. *Mass Spectrom Rev* 34, 184-208
68. Schieber, M., and Chandel, N. S. (2014) ROS function in redox signaling and oxidative stress. *Curr Biol* 24, R453-462
69. Fine, J. M., Forsberg, A. C., Renner, D. B., Faltesek, K. A., Mohan, K. G., Wong, J. C., Arneson, L. C., Crow, J. M., Frey, W. H., 2nd, and Hanson, L. R. (2014) Intranasally-administered deferoxamine mitigates toxicity of 6-OHDA in a rat model of Parkinsons disease. *Brain Res* 1574, 96-104
70. Kosmidis, S., Botella, J. A., Mandilaras, K., Schneuwly, S., Skoulakis, E. M., Rouault, T. A., and Missirlis, F. (2011) Ferritin overexpression in *Drosophila glia* leads to iron deposition in the optic lobes and late-onset behavioral defects. *Neurobiol Dis* 43, 213-219
71. van Bergen, L. A., Roos, G., and De Proft, F. (2014) From thiol to sulfonic acid: modeling the oxidation pathway of protein thiols by hydrogen peroxide. *J Phys Chem A* 118, 6078-6084
72. *Limon*-Pacheco, J., and Gonsebatt, M. E. (2009) The role of antioxidants and antioxidant-related enzymes in protective responses to environmentally induced oxidative stress. *Mutat Res* 674, 137-147
73. Ferrer-Sueta, G., Manta, B., Botti, H., Radi, R., Trujillo, M., and Denicola, A. (2011) Factors affecting protein thiol reactivity and specificity in peroxide reduction. *Chem Res Toxicol* 24, 434-450
74. Gungor, N., Ozyurek, M., Guclu, K., Cekic, S. D., and Apak, R. (2011) Comparative evaluation of antioxidant capacities of thiol-based antioxidants measured by different in vitro methods. *Talanta* 83, 1650-1658
75. McBean, G. J., Lopez, M. G., and Wallner, F. K. (2016) Redox-based therapeutics in neurodegenerative disease. *Br J Pharmacol*
76. Trujillo, M., Alvarez, B., and Radi, R. (2016) One- and two-electron oxidation of thiols: mechanisms, kinetics and biological fates. *Free Radic Res* 50, 150-171
77. Sies, H. (2017) Hydrogen peroxide as a central redox signaling molecule in physiological oxidative stress: Oxidative eustress. *Redox Biol* 11, 613-619
78. Sriram, K., Shankar, S. K., Boyd, M. R., and Ravindranath, V. (1998) Thiol oxidation and loss of mitochondrial complex I precede excitatory amino acid-mediated neurodegeneration. *J Neurosci* 18, 10287-10296
79. Luo, D., Smith, S. W., and Anderson, B. D. (2005) Kinetics and mechanism of the reaction of cysteine and hydrogen peroxide in aqueous solution. *J Pharm Sci* 94, 304-316
80. Hackett, M. J., Paterson, P. G., Pickering, I. J., and George, G. N. (2016) Imaging Taurine in the Central Nervous System Using Chemically Specific X-ray Fluorescence Imaging at the Sulfur K-Edge. *Anal Chem* 88, 10916-10924
81. Davies, M. J. (2016) Protein oxidation and peroxidation. *Biochem J* 473, 805-825
82. Mansuy, D., and Dansette, P. M. (2011) Sulfenic acids as reactive intermediates in xenobiotic metabolism. *Arch Biochem Biophys* 507, 174-185
83. Heppner, D. E., Janssen-Heininger, Y. M., and van der Vliet, A. (2017) The role of sulfenic acids in cellular redox signaling: Reconciling chemical kinetics and molecular detection strategies. *Arch Biochem Biophys* 616, 40-46
84. Nagy, P. (2013) Kinetics and mechanisms of thiol-disulfide exchange covering direct substitution and thiol oxidation-mediated pathways. *Antioxid Redox Signal* 18, 1623-1641
85. Ashby, M. T., and Nagy, P. (2006) On the kinetics and mechanism of the reaction of cysteine and hydrogen peroxide in aqueous solution. *J Pharm Sci* 95, 15-18
86. Nicholls, D. G. (2017) Brain mitochondrial calcium transport: Origins of the set-point concept and its application to physiology and pathology. *Neurochem Int*
87. Lewerenz, J., and Maher, P. (2015) Chronic Glutamate Toxicity in Neurodegenerative Diseases-What is the Evidence? *Front Neurosci* 9, 469
88. G. D. Zeevalk, L. P. B., C. Sinha, J. Ehrhart, W. J. Nicklas. (1998) Excitotoxicity and Oxidative Stress during Inhibition of Energy Metabolism. *Developmental Neuroscience* 20, 444-453
89. Van Den Bosch, L., Van Damme, P., Bogaert, E., and Robberecht, W. (2006) The role of excitotoxicity in the pathogenesis of amyotrophic lateral sclerosis. *Biochim Biophys Acta* 1762, 1068-1082
90. Stout, A. K., Raphael, H. M., Kanterewicz, B. I., Klann, E., and Reynolds, I. J. (1998) Glutamate-induced neuron death requires mitochondrial calcium uptake. *Nat Neurosci* 1, 366-373
91. Schwarz, J. B., Gibbons, S. E., Graham, S. R., Colbry, N. L., Guzzo, P. R., Le, V. D., Vartanian, M. G., Kinsora, J. J., Lotarski, S. M., Li, Z., Dickerson, M. R., Su, T. Z., Weber, M. L., El-Kattan, A., Thorpe, A. J., Donevan, S. D., Taylor, C. P., and Wustrow, D. J. (2005) Novel cyclopropyl beta-amino acid analogues of pregabalin and gabapentin that target the alpha2-delta protein. *J Med Chem* 48, 3026-3035
92. Ricci, L., Frosini, M., Gaggelli, N., Valensin, G., Machetti, F., Sgaragli, G., and Valoti, M. (2006) Inhibition of rabbit brain 4-aminobutyrate transaminase by some taurine analogues: a kinetic analysis. *Biochem Pharmacol* 71, 1510-1519

93. Graham Johnson, J. T. D., Peter A. Boxer and Robert F. Bruns. (1992) Beta-Proline Analogues as Agonists at the Strychnine-Sensitive Glycine Receptor. *J Med Chem* 35, 233-241

94. Allan, R. D., Curtis, D. R., Headley, P. M., Johnston, G. A., Kennedy, S. M., Lodge, D., and Twitchin, B. (1980) Cyclobutane analogs of GABA. *Neurochem Res* 5, 393-400

95. Zhao, X., Hoesl, C. E., Hoefner, G. C., and Wanner, K. T. (2005) Synthesis and biological evaluation of new GABA-uptake inhibitors derived from proline and from pyrrolidine-2-acetic acid. *Eur J Med Chem* 40, 231-247

96. Liebowitz, S. M., Lombardini, J. B., and Salva, P. S. (1987) Cyclic taurine analogs. Synthesis and effects on ATP-dependent Ca2+ uptake in rat retina. *Biochem Pharmacol* 36, 2109-2114

97. P. KROGSGAARD-LARSEN, H. H., D. R. CURTIS, D. LODGE, and JOHNSTON, a. G. A. R. (1979) Dihydromuscimol, thiomuscimol and related heterocyclic compounds as GABA analogues. *J Neurochem* 32, 1717-1724

98. Ricci, L., Valoti, M., Sgaragli, G., and Frosini, M. (2012) Taurine-like GABA aminotransferase inhibitors prevent rabbit brain slices against oxygen-glucose deprivation-induced damage. *Amino Acids* 42, 2139-2147

99. Della Corte, L., Crichton, R. R., Duburs, G., Nolan, K., Tipton, K. F., Tirzitis, G., and Ward, R. J. (2002) The use of taurine analogues to investigate taurine functions and their potential therapeutic applications. *Amino Acids* 23, 367-379

100. Lombardini, J. B., and Liebowitz, S. M. (2009) Taurine analogues as modifiers of the accumulation of 45calcium ions in a rat retinal membrane preparation. *Current Eye Research* 9, 1147-1156

101. Silverman, R. B. (2012) The 2011 E. B. Hershberg award for important discoveries in medicinally active substances: (1S,3S)-3-amino-4-difluoromethylenyl-1-cyclopentanoic acid (CPP-115), a GABA aminotransferase inactivator and new treatment for drug addiction and infantile spasms. *J Med Chem* 55, 567-575

102. Gupta, R. C., Win, T., and Bittner, S. (2005) Taurine analogues; a new class of therapeutics: retrospect and prospects. *Curr Med Chem* 12, 2021-2039

103. Krogsgaard-Larsen, P., Falch, E., and Hjeds, H. (1985) Heterocyclic analogues of GABA: chemistry, molecular pharmacology and therapeutic aspects. *Progress in medicinal chemistry* 22, 67-120

104. Yogeeswari, P., Ragavendran, J. V., and Sriram, D. (2006) An update on GABA analogs for CNS drug discovery. *Recent patents on CNS drug discovery* 1, 113-118

105. Ebert, B., Mortensen, M., Thompson, S. A., Kehler, J., Wafford, K. A., and Krogsgaard-Larsen, P. (2001) Bioisosteric determinants for subtype selectivity of ligands for heteromeric GABA(A) receptors. *Bioorg Med Chem Lett* 11, 1573-1577

106. Fink, K., Meder, W., Dooley, D. J., and Gothert, M. (2000) Inhibition of neuronal Ca(2+) influx by gabapentin and subsequent reduction of neurotransmitter release from rat neocortical slices. *Br J Pharmacol* 130, 900-906

107. Frosini, M., Sesti, C., Dragoni, S., Valoti, M., *Palmi*, M., Dixon, H. B., Machetti, F., and Sgaragli, G. (2003) Interactions of taurine and structurally related analogues with the GABAergic system and taurine binding sites of rabbit brain. *Br J Pharmacol* 138, 1163-1171

108. Krogsgaard-Larsen, P., Frolund, B., and Frydenvang, K. (2000) GABA uptake inhibitors. Design, molecular pharmacology and therapeutic aspects. *Current pharmaceutical design* 6, 1193-1209

109. Liebowitz, S. M., Lombardini, J. B., and Allen, C. I. (1988) Effects of aminocycloalkanesulfonic acid analogs of taurine on ATP-dependent calcium ion uptake and protein phosphorylation. *Biochem Pharmacol* 37, 1303-1309

110. Liebowitz, S. M., Lombardini, J. B., and Allen, C. I. (1989) Sulfone analogues of taurine as modifiers of calcium uptake and protein phosphorylation in rat retina. *Biochem Pharmacol* 38, 399-406

111. Nielsen, L., Brehm, L., and Krogsgaard-Larsen, P. (1990) GABA agonists and uptake inhibitors. Synthesis, absolute stereochemistry, and enantioselectivity of (R)—(-)- and (S)—(+)-homo-beta-proline. *J Med Chem* 33, 71-77

112. Qiu, J., Pingsterhaus, J. M., and Silverman, R. B. (1999) Inhibition and substrate activity of conformationally rigid vigabatrin analogues with gamma-aminobutyric acid aminotransferase. *J Med Chem* 42, 4725-4728

113. Gupta, R. C. (2006) Taurine analogues and taurine transport: therapeutic advantages. *Adv Exp Med Biol* 583, 449-467

114. Levandovskiy, I. A., Sharapa, D. I., Shamota, T. V., Rodionov, V. N., and Shubina, T. E. (2011) Conformationally restricted GABA analogs: from rigid carbocycles to cage hydrocarbons. *Future medicinal chemistry* 3, 223-241

115. Guerriero, R. M., Giza, C. C., and Rotenberg, A. (2015) Glutamate and GABA imbalance following traumatic brain injury. *Curr Neurol Neurosci Rep* 15, 27

116. Foerster, B. R., Pomper, M. G., Callaghan, B. C., Petrou, M., Edden, R. A., Mohamed, M. A., Welsh, R. C., Carlos, R. C., Barker, P. B., and Feldman, E. L. (2013) An imbalance between excitatory and inhibitory neurotransmitters in amyotrophic lateral sclerosis revealed by use of 3-T proton magnetic resonance spectroscopy. *JAMA Neurol* 70, 1009-1016

117. Fehily, B., and Fitzgerald, M. (2016) Repeated mild traumatic brain injury: potential mechanisms of damage. *Cell Transplant*

118. Manevich, Y., Hutchens, S., Halushka, P. V., Tew, K. D., Townsend, D. M., Jauch, E. C., and Borg, K. (2014) Peroxiredoxin VI oxidation in cerebrospinal fluid correlates with traumatic brain injury outcome. *Free Radic Biol Med* 72, 210-221

119. Margulies, S., Hicks, R., and Combination Therapies for Traumatic Brain Injury Workshop, L. (2009) Combination therapies for traumatic brain injury: prospective considerations. *J Neurotrauma* 26, 925-939

120. Bading, H. (2017) Therapeutic targeting of the pathological triad of extrasynaptic NMDA receptor signaling in neurodegenerations. *J Exp Med* 214, 569-578

121. White, R. J., and Reynolds, I. J. (1995) Mitochondria and Na+/Ca2+ exchange buffer glutamate-induced calcium loads in cultured cortical neurons. *J Neurosci* 15, 1318-1328

122. Mironov, S. L., Ivannikov, M. V., and Johansson, M. (2005) [Ca2+]i signaling between mitochondria and endoplasmic reticulum in neurons is regulated by microtubules. From mitochondrial permeability transition pore to Ca2+-induced Ca2+ release. *J Biol Chem* 280, 715-721

123. Patterson, M., Sneyd, J., and Friel, D. D. (2007) Depolarization-induced calcium responses in sympathetic neurons: relative contributions from Ca2+ entry, extrusion, ER/mitochondrial Ca2+ uptake and release, and Ca2+ buffering. *J Gen Physiol* 129, 29-56

124. Baumgartner, H. K., Gerasimenko, J. V., Thorne, C., Ferdek, P., Pozzan, T., Tepikin, A. V., Petersen, O. H., Sutton, R., Watson, A. J., and Gerasimenko, O. V. (2009) Calcium elevation in mitochondria is the main Ca2+ requirement for mitochondrial permeability transition pore (mPTP) opening. *J Biol Chem* 284, 20796-20803

125. Galgano, M. A., Cantu, R., and Chin, L. S. (2016) Chronic Traumatic Encephalopathy: The Impact on Athletes. *Cureus* 8, e532

126. Angoa-Perez, M., Kane, M. J., Briggs, D. I., Herrera-Mundo, N., Viano, D. C., and Kuhn, D. M. (2014) Animal models of sports-related head injury: bridging the gap between pre-clinical research and clinical reality. *J Neurochem* 129, 916-931

127. Blaylock, R. L., and Maroon, J. (2011) Immunoexcitotoxicity as a central mechanism in chronic traumatic encephalopathy-A unifying hypothesis. *Surg Neurol Int* 2, 107

128. Hackett, M. J., Smith, S. E., Paterson, P. G., Nichol, H., Pickering, I. J., and George, G. N. (2012) X-ray absorption spectroscopy at the sulfur K-edge: a new tool to investigate the biochemical mechanisms of neurodegeneration. *ACS Chem Neurosci* 3, 178-185

What is claimed:

1. A method of treating acute traumatic brain injury in a subject, comprising administering to the subject a small thiol compound having the structure of Formula Ib:

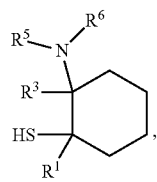

(Ib)

wherein
$R^1$ is H or $C_{1-5}$ alkyl;
$R^3$ is H or $C_{1-5}$ alkyl; and
$R^5$ and $R^6$ are independently selected from the group consisting of H and $C_{1-5}$ alkyl;

wherein a $C_{1-5}$ alkyl moiety, wherever it occurs, can optionally comprise a double bond; and wherein a $C_{1-5}$ alkyl, wherever it occurs, can optionally be substituted with from one to three substituents which are not further substituted and which are independently selected from the group consisting of —CN, thio, halo, hydroxy, $C_{6-10}$ aryl, $C_{1-6}$ alkyl, $C_{2-6}$ alkenyl, $C_{3-6}$ cycloalkyl, 5- or 6-membered heterocycloalkyl containing 1-3 heteroatoms selected from O, N, and S, $CO_2H$, $CO_2C_{1-6}$ alkyl, $C(O)C_{1-6}$ alkyl, $CO_2NH_2$, $CO_2NHC_{1-6}$ alkyl, and —$CO_2N(C_{1-6}$ alkyl$)_2$.

2. The method of claim 1, wherein the compound is selected from compound 58 and 123:

| Compound No. | Structure |
|---|---|
| 58 | 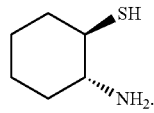 |
| 123 | ![](NH2, SH structure with propyl) |

3. The method of claim 2, wherein the compound is compound 58:

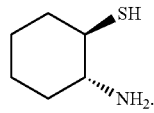

(58)

* * * * *